US012735415B2

(12) United States Patent
Platzek et al.

(10) Patent No.: US 12,735,415 B2
(45) Date of Patent: Sep. 15, 2026

(54) PROCESS FOR THE PREPARATION OF 2-CYANOETHYL (4S)-4-(4-CYANO-2-METHOXY-PHENYL)-5-ETHOXY-2,8-DIMETHYL-1,4-DIHYDRO-1,6-NAPHTHYRIDINE-3-CARBOXYLATE BY RESOLUTION OF RACEMATES BY MEANS OF DIASTEREOMERIC TARTARIC ACID ESTERS

(71) Applicant: Bayer Aktiengesellschaft, Leverkusen (DE)

(72) Inventors: Johannes Platzek, Berlin (DE); Kai Lovis, Düsseldorf (DE)

(73) Assignee: Bayer Aktiengesellschaft, Leverkusen (DE)

( * ) Notice: Subject to any disclaimer, the term of this patent is extended or adjusted under 35 U.S.C. 154(b) by 1079 days.

(21) Appl. No.: 17/769,263

(22) PCT Filed: Oct. 12, 2020

(86) PCT No.: PCT/EP2020/078613

§ 371 (c)(1),
(2) Date: Apr. 14, 2022

(87) PCT Pub. No.: WO2021/074078

PCT Pub. Date: Apr. 22, 2021

(65) Prior Publication Data

US 2024/0199599 A1 Jun. 20, 2024

(30) Foreign Application Priority Data

Oct. 17, 2019 (EP) .................................... 19203825

(51) Int. Cl.

*C07D 471/04* (2006.01)
*C07C 68/00* (2020.01)
*C07C 69/78* (2006.01)

(52) U.S. Cl.

CPC ............ *C07D 471/04* (2013.01); *C07C 68/00* (2013.01); *C07C 69/78* (2013.01); *C07B 2200/07* (2013.01)

(58) Field of Classification Search

CPC .................................................... C07D 471/04
See application file for complete search history.

(56) References Cited

U.S. PATENT DOCUMENTS

| | | | |
|---|---|---|---|
| 5,037,987 | A | 8/1991 | Herrmann et al. |
| 8,436,180 | B2 | 5/2013 | Barfacker et al. |
| 9,051,316 | B2 | 6/2015 | Barfacker et al. |
| 10,059,707 | B2 | 8/2018 | Platzek et al. |
| 12,054,481 | B2 | 8/2024 | Platzek et al. |
| 12,089,086 | B2 | 9/2024 | Sha et al. |
| 2021/0163474 | A1 | 6/2021 | Platzek et al. |

FOREIGN PATENT DOCUMENTS

| | | | |
|---|---|---|---|
| CA | 2679232 | C | 7/2016 |
| CN | 106432199 | A | 2/2017 |
| JP | 2275879 | A | 11/1990 |
| JP | 2010-519232 | A | 6/2010 |
| JP | 2022-522984 | B2 | 12/2022 |
| WO | 2008104306 | A2 | 9/2008 |
| WO | 2016016287 | A1 | 2/2016 |
| WO | 2019206909 | A1 | 10/2019 |

OTHER PUBLICATIONS

Zhonge, et al., "A parallel approach to direct resolution of albuterol", Chinese Science Bulletin, 55(25): 2814-2816, Sep. 2010.
Bärfacker, L. et al., "Discovery of BAY 94-8862: A Nonsteroidal Antagonist of the Mineralocorticoid Receptor for the Treatment of Cardiorenal Diseases," ChemMedChem 2012, 7, pp. 1385-1403.
Chen, J. et al., "The Comparison in Enantioseparation Ability of the Chiral Stationary Phases with Single and Mixed Selector—The Selectors Derived from Two D-Tartrates," Chirality 2011, 23, pp. 228-236.
Furuta, K. et al., "Chiral (Acyloxy)Borane Complex-Catalyzed Asymmetric Diels-Alder Reaction: (1R)-1,3,4-Trimethyl-3-Cyclohexene-1-Carboxaldehyde," Organic Syntheses 1995, vol. 72, pp. 86-94.
Furuta, K. et al., "Chiral (Acyloxy)Borane Complex-Catalyzed Asymmetric Diels-Alder Reaction: (1R)-1,3,4-Trimethyl-3-Cyclohexene-1-Carboxaldehyde," Organic Syntheses 1998, Coll. vol. 9, p. 722 (6 pages).
International Search Report of PCT/EP2020/078613 (filed on Oct. 12, 2020 by Bayer Aktiengesellschaft). International search completed on Nov. 9, 2020 and mailed on Nov. 24, 2020 by the European Patent Office, 15 pages.
Paredes, G. et al., "Optimization of stimulated moving bed and column chromatography for a plasmid DNA purification step and for a chiral separation," J. Chromatogr. A, 2007, 1142, pp. 56-68.
Stahl, P.H. et al.(eds.), "Salt Formation—Is It Necessary, Is It Feasible?," Handbook of Pharmaceutical Salts: Properties, Selection, and Use. Weinheim: VHCA, 2002. Print, pp. 164-167.

(Continued)

*Primary Examiner* — John S Kenyon
(74) *Attorney, Agent, or Firm* — Quarles & Brady LLP

(57) ABSTRACT

The present invention relates to the diastereomeric salts (Va), (Vb), (Vc) and/or (Vd), to a process for preparing the diastereomeric salts (Va), (Vb), (Vc) and/or (Vd) using a chiral substituted tartaric ester of the formula (IIIa) or (IIIb), to a process for preparing the compound of formula (IVa) using the diastereomeric salts (Va), (Vb), (Vc) and/or (Vd), to a process for preparing the compound of the formula (VIIa) using the diastereomeric salts (Va), (Vb), (Vc) and/or (Vd), to a process for preparing the compound of the formula (Ia) using the diastereomeric salts (Va), (Vb), (Vc) and/or (Vd), to the use of the diastereomeric salts (Va), (Vb), (Vc) and/or (Vd) for preparation of one of the compounds of formula (IVa), (VIIa) and/or (Ia), to the use of a chiral substituted tartaric esters of the formula (IIIa) or (IIIb) for preparation of the diastereomeric salts (Va), (Vb), (Vc) and/or (Vd), and to the use of a chiral substituted tartaric ester of the formula (IIIa) or (IIIb) for preparation of one of the compounds of formula (IVa), (VIIa) and/or (Ia).

16 Claims, No Drawings

(56) References Cited

OTHER PUBLICATIONS

Subramani, H.J. et al., "Optimization of reactive SMB and Varicol systems," Computers and Chemical Engineering, 2003, 27, pp. 1883-1901.
Dingqiang, L. et al., "Progress in chiral resolution and asymmetric synthesis of 1, 4-dihydropyridine derivatives," Chemical Industry and Engineering Progress, 2010, 29(12), pp. 2351-2361, 2378.
Synoradzki, L. et al., " Tartaric Acid and Its O-Acyl Derivatives. Part 2. Application of Tartaric Acid and of O-Acyl Tartaric Acids and Anhydrides. Resolution of Racemates," Organic Preparations and Procedures Int., 2008, 40(2), pp. 163-200.
International Search Report and Written Opinion of PCT/EP2020/078600 (filed on Oct. 12, 2020 by Bayer Aktiengesellschaft). International search completed on Nov. 9, 2020 and mailed on Nov. 18, 2020 by the European Patent Office, 11 pages.

PROCESS FOR THE PREPARATION OF 2-CYANOETHYL (4S)-4-(4-CYANO-2-METHOXY-PHENYL)-5-ETHOXY-2,8-DIMETHYL-1,4-DIHYDRO-1,6-NAPHTHYRIDINE-3-CARBOXYLATE BY RESOLUTION OF RACEMATES BY MEANS OF DIASTEREOMERIC TARTARIC ACID ESTERS

The present invention relates to the diastereomeric salts (Va), (Vb), (Vc) and/or (Vd), to a process for preparing the diastereomeric salts (Va), (Vb), (Vc) and/or (Vd) using a chiral substituted tartaric esters of the formula (IIIa) or (IIIb), to a process for preparing the compound of formula (IVa) using the diastereomeric salts (Va), (Vb), (Vc) and/or (Vd), to a process for preparing the compound of the formula (VIIa) using the diastereomeric salts (Va), (Vb), (Vc) and/or (Vd), to a process for preparing the compound of the formula (Ia) using the diastereomeric salts (Va), (Vb), (Vc) and/or (Vd), to the use of the diastereomeric salts (Va), (Vb), (Vc) and/or (Vd) for preparation of one of the compounds of formula (IVa), (VIIa) and/or (Ia), to the use of a chiral substituted tartaric ester of the formula (IIIa) or (IIIb) for preparation of the diastereomeric salts (Va), (Vb), (Vc) and/or (Vd), and to the use of a chiral substituted tartaric ester of the formula (IIIa) or (IIIb) for preparation of one of the compounds of formula (IVa), (VIIa) and/or (Ia).

The abovementioned compounds are intermediates or precursors in the synthesis of finerenone (formula (Ia)). The term "finerenone" relates to the compound (4S)-4-(4-cyano-2-methoxyphenyl)-5-ethoxy-2,8-dimethyl-1,4-dihydro-1,6-naphthyridine-3-carboxamide or to the compound of formula (Ia)

(Ia)

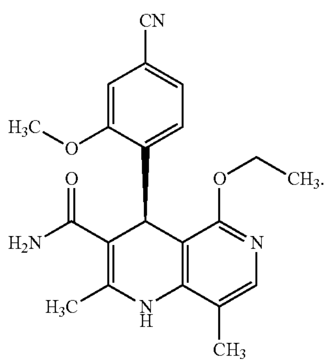

The compound of the formula (I)

(I)

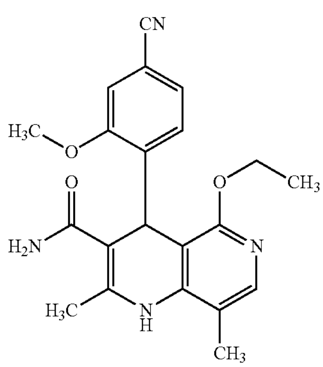

is the racemate of finerenone.

The expression "antipodes of finerenone" or "antipodes of the compound of formula (I)" concerns the compounds of formulae (Ia) and (Ib)

(Ia)

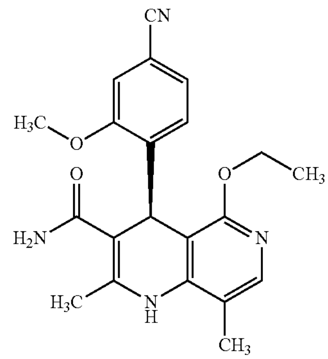

(Ib)

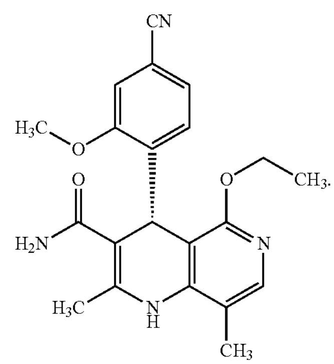

Finerenone (Ia) acts as a nonsteroidal antagonist of the mineralocorticoid receptor and can be used as an agent for prophylaxis and/or treatment of cardiovascular and renal disorders such as heart failure and diabetic nephropathy.

The compound of the formula (I) or (Ia) and the preparation process therefor are described in WO 2008/104306 and ChemMedChem 2012, 7, 1385, and also in WO 2016/016287 A1. In order to arrive at the compound of the formula (I), the racemic mixture of the amides (I)

(I)

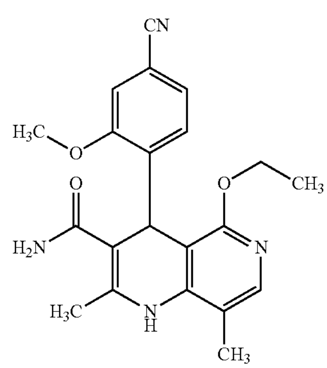

has to be separated into the antipodes (Ia) and (Ib)

(Ia)

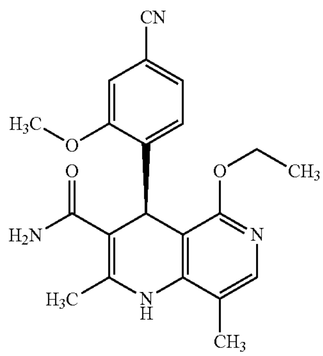

(Ib)

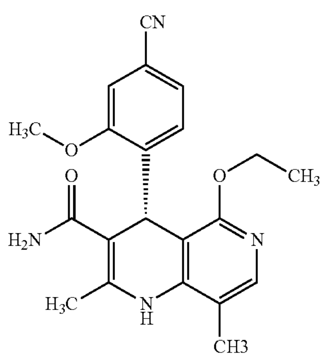

since only the antipode of the formula (Ia)

(Ia)

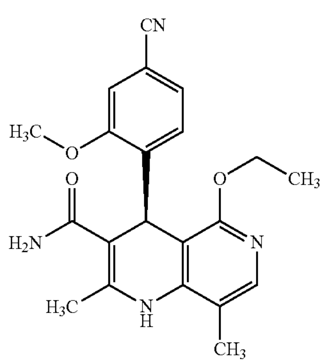

is active.

In the published research scale synthesis (WO 2008/104306 A1), a specifically synthesized chiral phase was used for this purpose (prepared in-house), which contained N-(dicyclopropylmethyl)-$N^2$-methacryloyl-D-leucinamide as chiral selector. It has been found that the separation can also be performed on a readily commercially available phase. This is the Chiralpak AS-V phase, 20 μm. The eluent used was a mixture of methanol/acetonitrile 60:40. In this case, the chromatography can be conducted on a conventional chromatography column, but preference is given to using the techniques known to those skilled in the art such as SMB (simulated moving bed; G. Paredes, M. Mazotti, Journal of Chromatography A, 1142 (2007): 56-68) or Varicol (Computers and Chemical Engineering 27 (2003) 1883-1901).

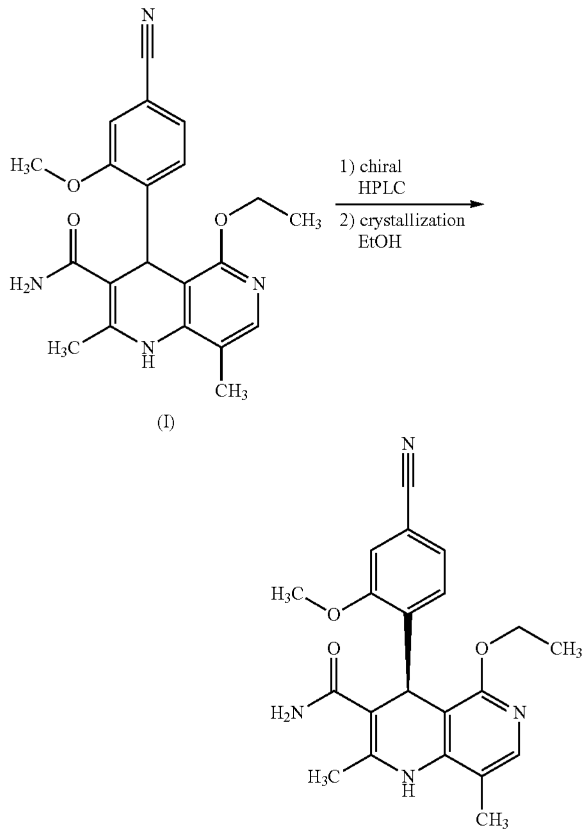

(I)

(Ia)

Although SMB separation affords a relatively good yield and optical purity, the procurement costs and the operation of such a facility under GMP conditions poses a great challenge and is associated with high costs. The respective chiral phase employed, too, is very expensive and has only a limited life span and has to be frequently replaced during continuous production. For reasons of production engineering, this is not optimal unless there is a second plant to ensure continuous operation, which is associated with additional costs. Furthermore, especially in the case of products produced on a ton scale, solvent recovery is the time-limiting step and requires the procurement of huge falling-film evaporators and is associated with the consumption of enormous amounts of energy.

The problem addressed was therefore to look for an alternative synthetic route to enantiomerically pure finerenone (I) that is significantly less costly and can be performed with conventional pilot plant equipment (stirred tanks/isolation apparatuses). Such facilities are traditionally standard equipment of pharmaceutical production plants and do not require additional investments. Moreover, qualification and validation of batch processes is considerably easier than that of chromatographic processes, which is an additional advantage.

In the novel process of the invention, rather than the discussed complex SMB separation of the racemic mixture of the amides (I)

(I)

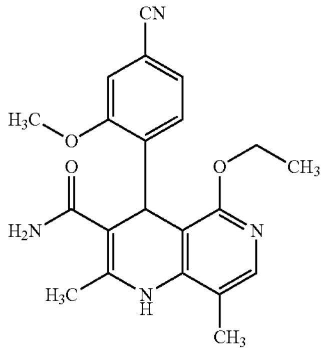

into the antipodes of the formulae (Ia) and (Ib), an enzymatic optical resolution is undertaken on a synthesis precursor, the racemic unit (IV)

(IV)

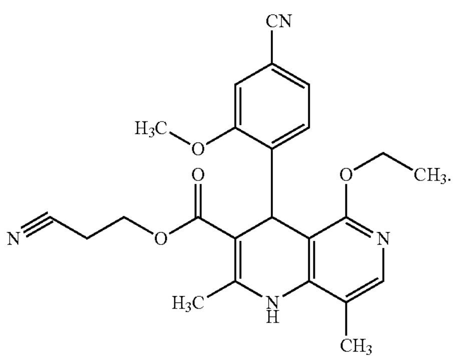

The synthesis of the racemic cyanoethanol ester of formula (IV) is described in WO 2016/016287 A1 (cf. example 5 in WO 2016/016287 A1; this is the compound of formula (XI)).

Numerous attempts were made, using the customary conventional methods, to develop an optical resolution of the racemate (IV) to the antipodes (IVa) and (IVb)

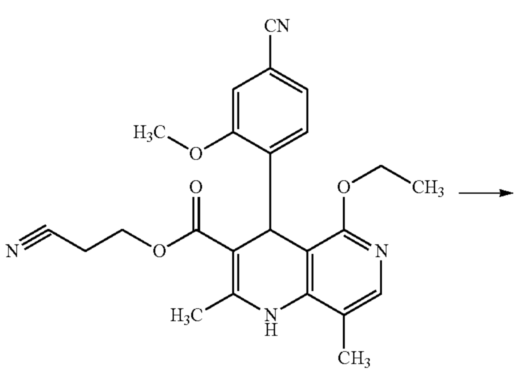

(IV)

-continued

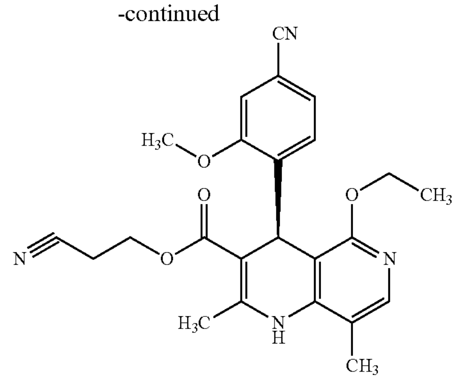

(IVa)

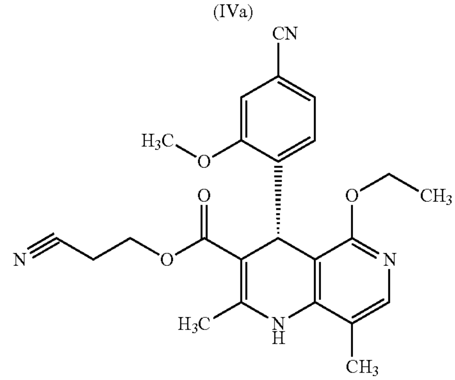

(IVb)

(variation of chiral organic acid and solvent), as shown in Table 1:

TABLE 1

| Acid |
|---|
| (S)-(+)-1,1-binaphthyl-2,2-diyl hydrogenphosphate |
| (−)-quinic acid |
| (−)-O,O'-diacetyl-L-tartaric acid |
| (−)-O,O'-dipivaloyl-L-tartaric acid |
| (+)-3-bromocamphor-10-sulfonic acid |
| (+)-4-chlorotartranilic acid |
| (+)-4'-nitrotartranilic acid |
| (+)-camphoric acid |
| (+)-O-acetyl-L-mandelic acid |
| (1R)-(−)-camphor-10-sulfonic acid |
| (1S)-(−)-camphanic acid |
| (2R,3R)-(+)-tartaric acid |
| (R)-(+)-alpha-methoxy-alpha-trifluoromethylphenylacetic acid |
| (S)-(−)-2-bromopropionic acid |
| (S)-(−)-2-chloropropionic acid |
| (S)-(+)-citramalic acid |
| (S)-(+)-mandelic acid |
| Ac-acid triple mix |
| malic acid |
| D-(+)-HPP monoacid |
| L-glutamic acid |
| L-lactic acid |
| menthoxyacetic acid |
| N-(3,5-dinitrobenzoyl)-(R)-(−)-2-phenylglycine |
| N-acetyl-L-leucine |
| N-acetyl-L-phenylalanine |
| N-Ac-proline-OH |
| naproxen |

Table 1 lists the acids used for optical resolution. These were reacted with the racemate (IV) in various organic solvents, for example in pure alcohols (methanol, ethanol, 1-propanol, 2-propanol, butanol), and mixtures thereof with water, and also THF, acetone, ethyl acetate, dichloromethane, and a further number of other solvents, and analysed for diastereomeric salt formation.

Also among the experiments conducted were experiments with the classic resolving agent (+)-tartaric acid.

However, salt formation was not observed in any of the cases; all that happens instead is that the racemate precipitates out of the solution without forming a salt. This corresponds essentially to the expectations of the person skilled in the art, since it could have been inferred from the pKa of the racemic molecule (IV) that conventional optical resolution by diastereomer salt formation with organic acids should not be possible since the measured pKa (for the base) is at 4.3 and hence virtually rules out salt formation. According to the literature, for example "Handbook of Pharmaceutical Salts—Properties, Selection and Use; by P. Heinrich Stahl, Camille G. Wermuth (Eds.); Wiley-VCH, p. 166", the pK difference should be at least 3 pK units to allow stable salt formation.

All efforts to obtain diastereomeric salts and then to bring the enantiomeric excess in the direction of >99% e.e. by subsequent synthesis steps were unproductive; therefore, further alternatives were sought.

No salt formation was observed in reactions with alkyl-substituted tartaric acid derivatives such as (−)-O,O'-dipivaloyl-L-tartaric acid or (−)-O,O'-diacetyl-L-tartaric acid.

However, it was found that, surprisingly, aromatically or heteroaromatic substituted derivatives of tartaric acid (IIIa+IIIb) are of excellent suitability to obtain diastereomeric salts and to achieve the enantiomeric excess required.

In summary, the invention relates to the following subject-matter:

(1) Diastereomeric salts (Va), (Vb), (Vc) and/or (Vd)

(Va)

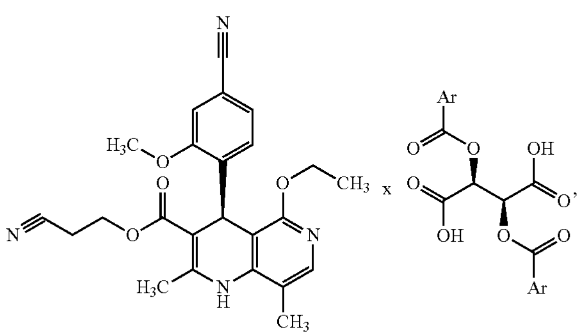

-continued (Vb)

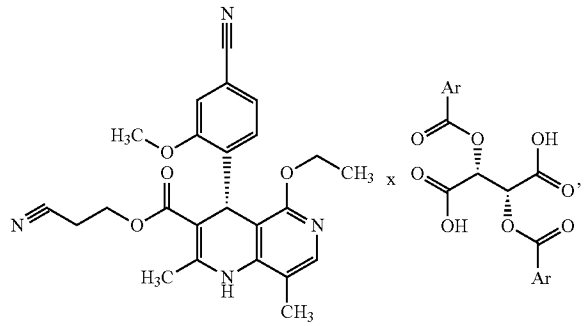

(Vc)

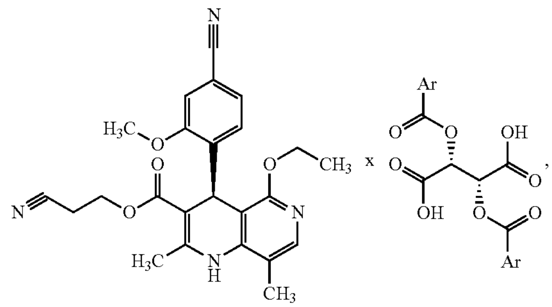

or (Vd)

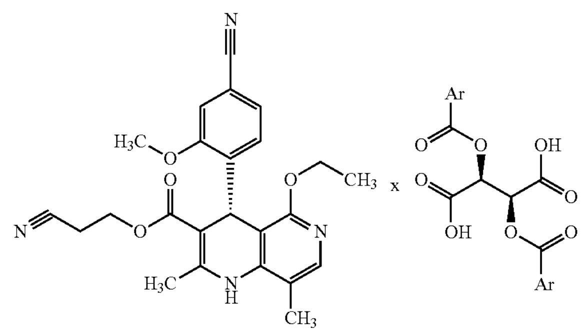

(2) Process for preparing the diastereomeric salts (Va), (Vb), (Vc) and/or (Vd) using a chiral substituted tartaric ester of the formula (IIIa) or (IIIb)

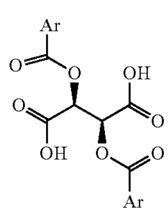

(III)a or

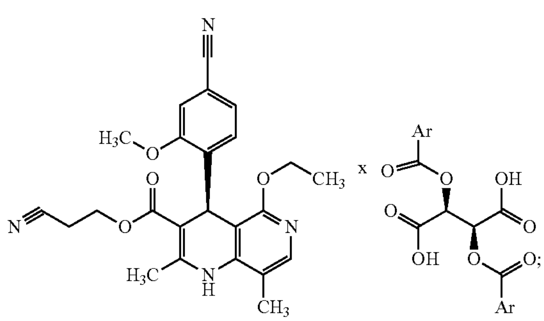

(Va)

-continued
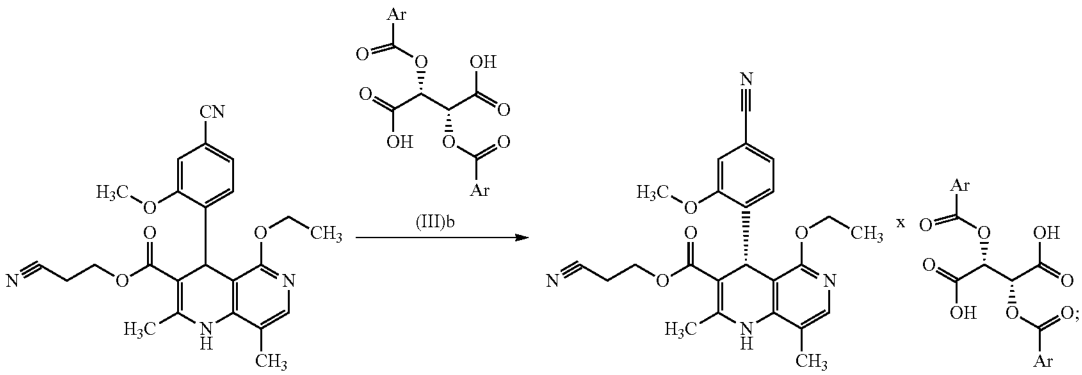
(IV) (Vb)
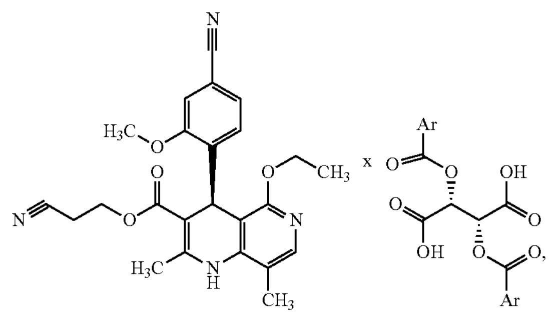
(Vc)
or
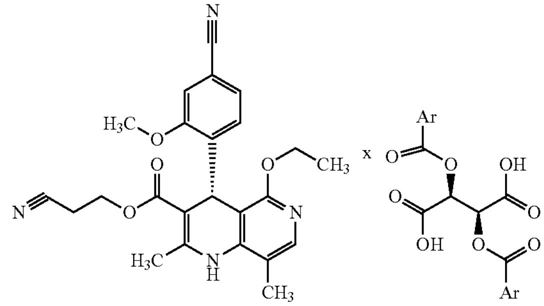
(Vd)

(3) Process for preparing the compound of formula (IVa) using the diastereomeric salts (Va), (Vb), (Vc) and/or (Vd)
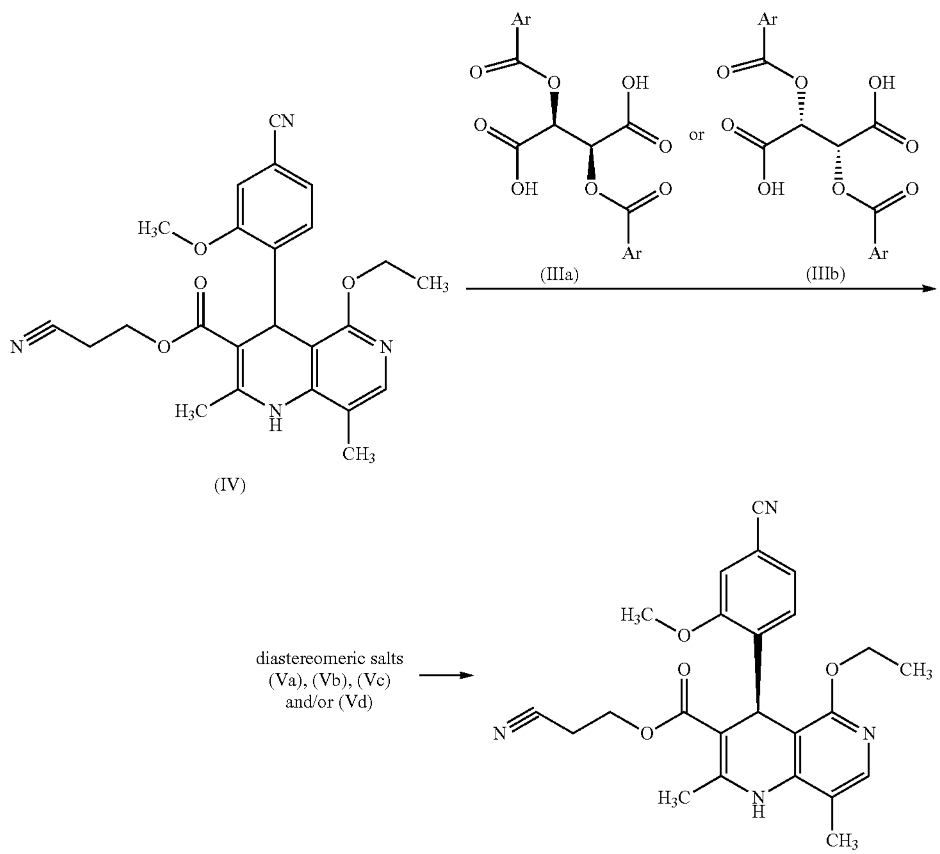
(IV)
(IIIa) or (IIIb)
(IVa)
(4) Process for preparing the compound of formula (VIIa) using the diastereomeric salts (Va), (Vb), (Vc) and/or (Vd)
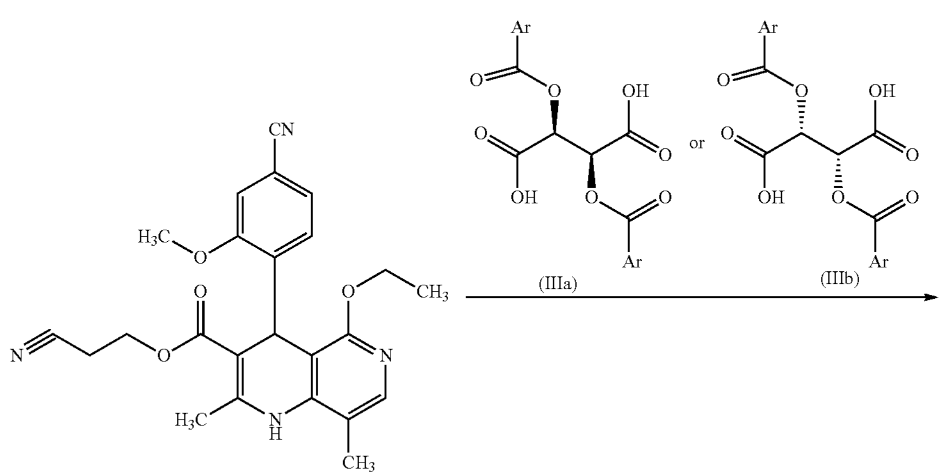
(IV)
(IIIa) or (IIIb)

-continued
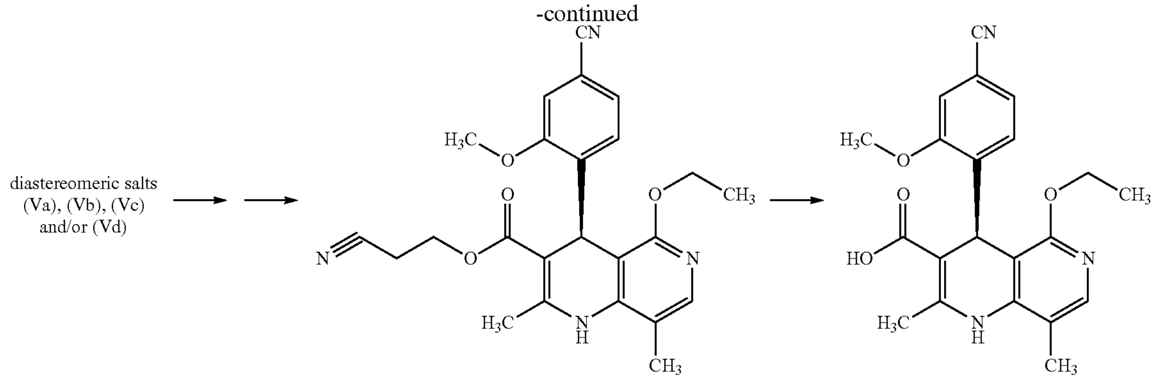
(IVa) (VIIa)
(5) Process for preparing the compound of formula (Ia) using the diastereomeric salts (Va), (Vb), (Vc) and/or (Vd)
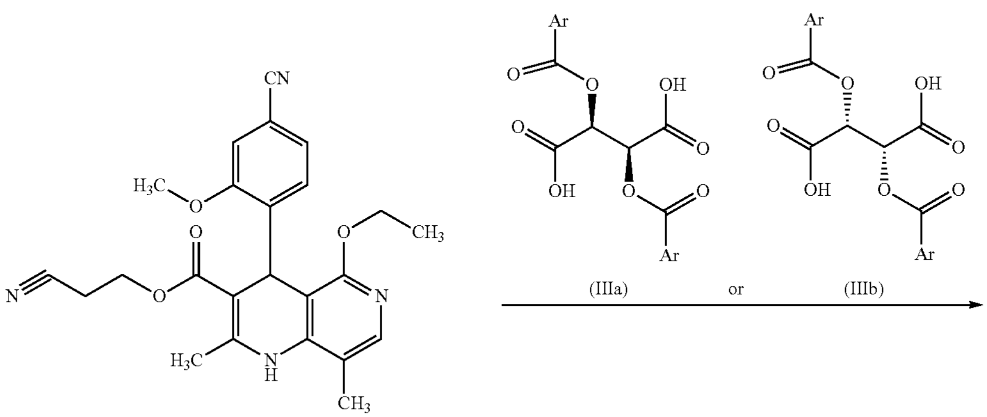
(IIIa) or (IIIb)
(IV)
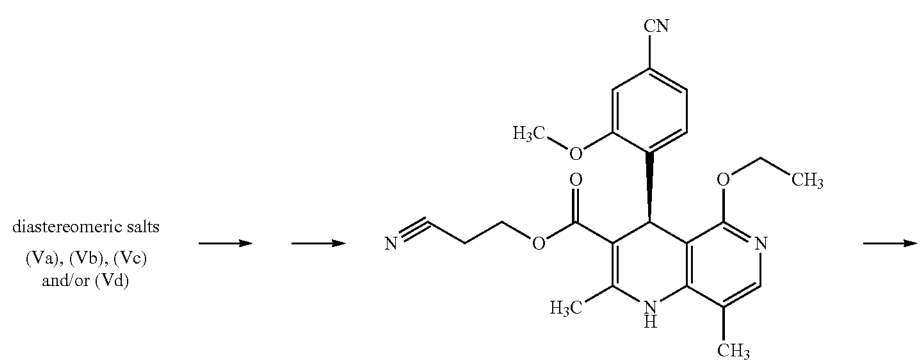
(IVa)

-continued

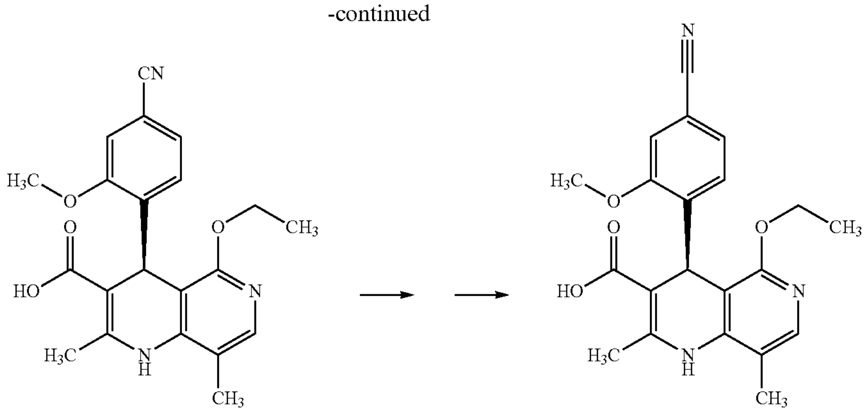

(VIIa) (Ia)

(6) Use of the diastereomeric salts (Va), (Vb), (Vc) and/or (Vd) for preparation of one of the compounds of formula (IVa), (VIIa) and/or (Ia);

(7) Use of a chiral substituted tartaric ester of the formula (IIIa) or (IIIb) for preparation of one of the diastereomeric salts (Va), (Vb), (Vc) and/or (Vd); and (8) Use of a chiral substituted tartaric ester of the formula (IIIa) or (IIIb) for preparation of one of the compounds of formula (IVa), (VIIa) and/or (Ia).

The technical effects of the invention can be summarized as follows:

The novel processes of the invention are employable in many less expensive processes or plants by comparison with the prior art described above;

The novel processes of the invention can be performed with conventional pilot plant equipment (stirred tanks/insulation apparatus)—such plants are traditionally part of the standard equipment in pharmaceutical production facilities and do not require any additional capital costs.

The novel processes of the invention can be effected on an industrial scale;

By the processes of the invention, it is possible to prepare diastereomeric salts having an enantiomeric excess of the diastereomeric salts in the range from 65% to 80% e.e.

The diastereomeric salts obtained by processes of the invention are notable for a high enantiomeric excess, generally >95% e.e., which is sufficient to prepare finerenone in >>99% e.e.

The diastereomeric salts need not necessarily be dried, but may also be used moist in the next process stage. This also enables one-pot processes;

It has been found that, in a conversion of the acid (VIIa or VIIb) in tetrahydrofuran (THF), the amide of formula (I) or (Ia) crystallizes directly out of the solution and can be obtained in high yield and purity;

In the synthesis of the invention, it is possible to avoid further intermediate steps, and hence the synthesis can be conducted in a time- and cost-efficient manner;

Examples of such intermediate steps are, for example, further purifications and/or cost-/energy-intensive recovery of individual constituents, recovery or removal of solvents.

The present application therefore provides a process for preparing 2-cyanoethyl (4S)-4-(4-cyano-2-methoxyphenyl)-5-ethoxy-2,8-dimethyl-1,4-dihydro-1,6-naphthyridine-3-carboxylate of the formula (IVa)

(IVa)

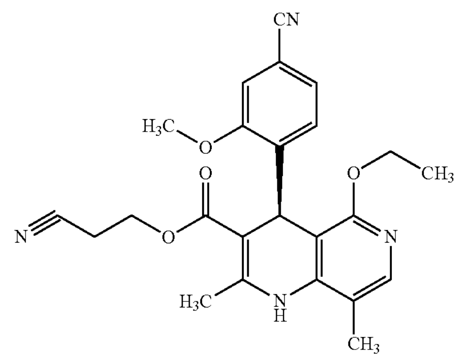

by optical resolution of the racemate (IV)

(IV)

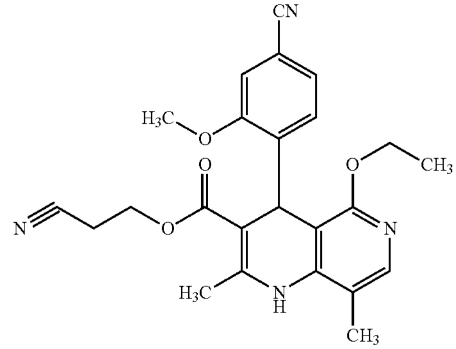

using a chiral substituted tartaric ester of the formula (IIIa)

(IIIa)

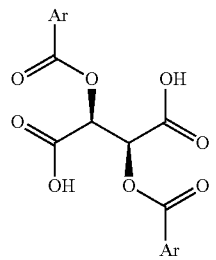

where Ar is unsubstituted or substituted aryl or heteroaryl.

The term "substituted" means that one or more hydrogen atoms on the atom or group in question has/have been replaced by a selection from the group specified, with the proviso that the normal valency of the atom in question is not exceeded under the particular circumstances. Combinations of substituents and/or variables are permissible.

The term "unsubstituted" means that none of the hydrogen atoms have been replaced.

The heteroaryl group may be a 5-membered heteroaryl group, for example thienyl, furanyl, pyrrolyl, oxazolyl, thiazolyl, imidazolyl, pyrazolyl, isoxazolyl, isothiazolyl, oxadiazolyl, triazolyl, thiadiazolyl or tetrazolyl; or a 6-membered heteroaryl group, for example pyridinyl, pyridazinyl, pyrimidinyl, pyrazinyl or triazinyl; or a tricyclic heteroaryl group, for example carbazolyl, acridinyl or phenazinyl; or a 9-membered heteroaryl group, for example benzofuranyl, benzothienyl, benzoxazolyl, benzisoxazolyl, benzimidazolyl, benzothiazolyl, benzotriazolyl, indazolyl, indolyl, isoindolyl, indolizinyl or purinyl; or a 10-membered heteroaryl group, for example quinolinyl, quinazolinyl, isoquinolinyl, cinnolinyl, phthalazinyl, quinoxalinyl or pteridinyl.

The heteroaryl group is in particular a pyridinyl, pyrazinyl, pyrrolyl, pyrazolyl or pyrimidinyl group.

For the purposes of the present application, an aryl group is in particular a phenyl group. Substituents in the context of the present invention are halogen, $C_1$-$C_6$-alkyl, $C_1$-$C_6$-alkoxy, nitrile, nitro, cyano, $CF_3$, an amide group, for example —NHCOR in which R is methyl, ethyl or phenyl, an —NRCOR group in which R has the definition given above, a —CONHR group in which R has the definition given above, CONRR' in which R may be methyl, ethyl or phenyl and R' may be methyl, ethyl or phenyl, or cyclic amides such as 3-oxomorpholin-4-yl, 2-oxopiperidin-1-yl, which may in turn be substituted.

The term "halogen" refers to a fluorine, chlorine, bromine or iodine atom, preferably a fluorine, chlorine or bromine atom.

The term "$C_1$-$C_6$-alkyl" denotes a straight-chain or branched saturated monovalent hydrocarbon group having 1, 2, 3, 4, 5 or 6 carbon atoms, for example a methyl, ethyl, propyl, isopropyl, butyl, sec-butyl, isobutyl, tert-butyl, pentyl, isopentyl, 2-methylbutyl, 1-methylbutyl, 1-ethylpropyl, 1,2-dimethylpropyl, neopentyl, 1,1-dimethylpropyl, hexyl, 1-methylpentyl, 2-methylpentyl, 3-methylpentyl, 4-methylpentyl, 1-ethylbutyl, 2-ethylbutyl, 1,1-dimethylbutyl, 2,2-dimethylbutyl, 3,3-dimethylbutyl, 2,3-dimethylbutyl, 1,2-dimethylbutyl or 1,3-dimethylbutyl group or an isomer thereof. The group especially has 1, 2, 3 or 4 carbon atoms ("$C_1$-$C_4$-alkyl"), for example a methyl, ethyl, propyl, isopropyl, butyl, sec-butyl, isobutyl or tert-butyl group, especially 1, 2 or 3 carbon atoms ("$C_1$-$C_3$-alkyl"), for example a methyl, ethyl, n-propyl or isopropyl group.

The term "$C_1$-$C_6$-alkoxy" denotes a straight-chain or branched saturated monovalent group of the formula ($C_1$-$C_6$-alkyl)-O— in which the term "$C_1$-$C_6$-alkyl" is as defined above, for example a methoxy, ethoxy, n-propoxy, isopropoxy, n-butoxy, sec-butoxy, isobutoxy, tert-butoxy, pentyloxy, isopentyloxy or n-hexyloxy group or an isomer thereof.

Ar is preferably:

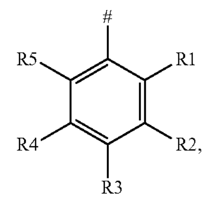

where #represents the site of attachment, where R1, R2, R3, R4, R5 are each a hydrogen atom or an alkyl radical, for example methyl, ethyl, propyl, or a halogen atom, for example fluorine, chlorine, bromine or iodine, or an ether group, for example O-methyl, O-ethyl, O-phenyl, or a nitro group, or a cyano group, or a CF3 group, or an amide group, for example —NHCOR in which R may be methyl, ethyl or phenyl, or —NRCOR in which R has the meaning given above or CONHR— in which R has the meaning given above or CONRR' in which R may be methyl, ethyl or phenyl and R' may be methyl, ethyl or phenyl, or cyclic amides such as 3-oxomorpholin-4-yl, 2-oxopiperidin-1-yl, which may in turn be substituted. The substitution patterns may differ widely; for instance, up to 5 different substituents are theoretically possible, but preference is generally given to the monosubstituted Ar radicals. Ar may alternatively be a substituted heteroaromatic radical such as, preferably, pyridine or pyrazine. Ar may alternatively be a polycyclic aromatic hydrocarbon, for example a substituted naphthalene, anthracene or quinoline.

More preferably, Ar is one of the formulae

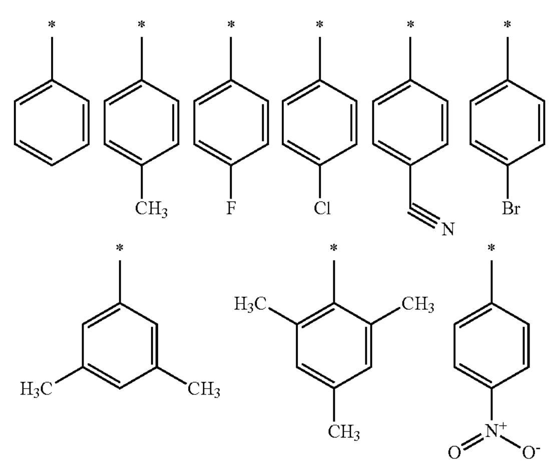

-continued

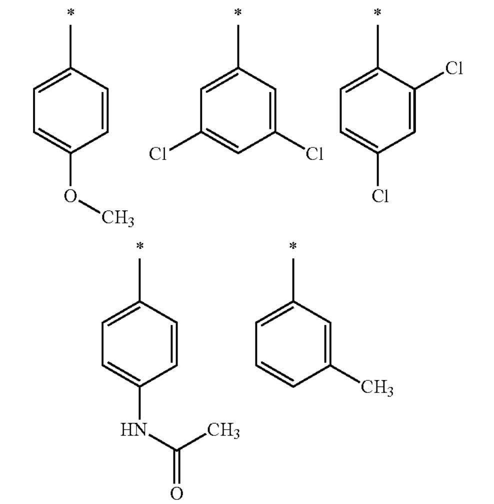

in which * represents the site of attachment.

Especially preferably, Ar is one of the formulae

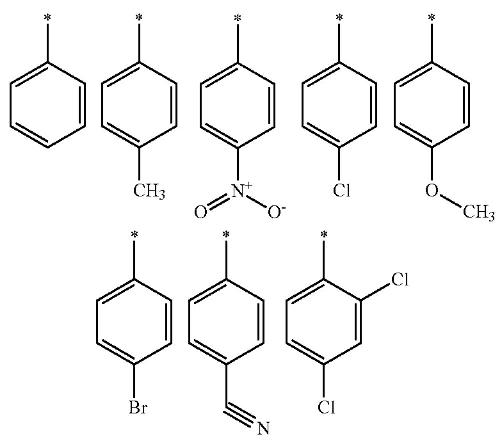

in which * represents the site of attachment.

Very particularly preferred Ar radicals are:

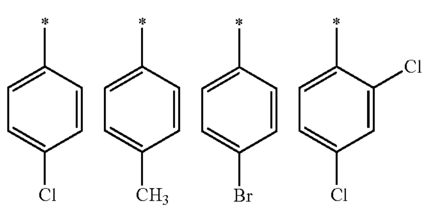

in which * represents the site of attachment.

Of which the p-tolyl radical and the 4-chlorophenyl radical are particularly preferred.

The p-tolyl radical is very particularly preferred.

The preparation of the tartaric esters is known from the literature, as described, for example, in Organic Synthesis, Coll. Vol. 9, p. 722 (1998); vol. 72, p. 86 (1995), and in Chirality 2011 (23), 3, p. 228.

A further subject of the invention relates to diastereomeric salts (Va to Vd) of the formulae (Va)

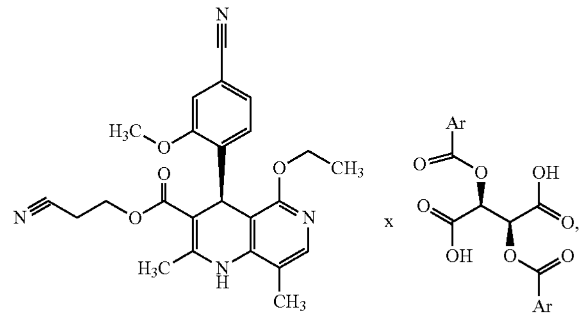

(Vb)

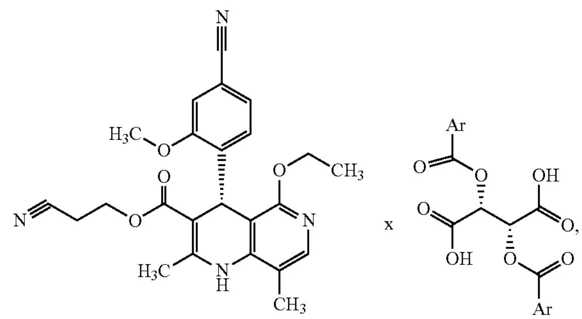

(Vc)

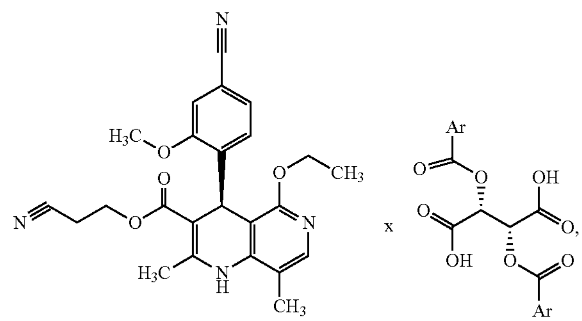

or (Vd)

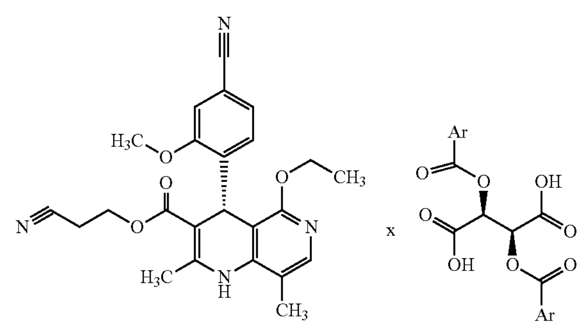

in which Ar is an unsubstituted or substituted aromatic or heteroaromatic radical and has the meaning given above.

Particular preference is given to diastereomeric salts in which Ar is p-tolyl.

Whether (Va) to (Vd) are truly conventional diastereomeric salts or 1:1 molecule complexes stabilized via hydrogen bond formation is not predictable with certainty. What is clear is that these molecular 1:1 aggregates are very stable and behave like conventional diastereomeric salts and can be isolated, and so we will use the term diastereomeric salts hereinafter. For the preparation of the diastereomeric salts, tartaric acid derivatives of the general formulae (IIIa) and (IIIb) are used:

(IIIa)

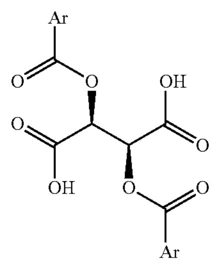

(IIIb)

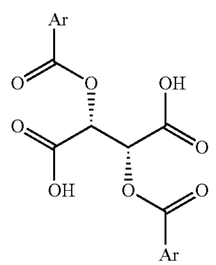

in which Ar is a substituted or unsubstituted aromatic or heteroaromatic radical and has the meaning given above.

The preparation of the diastereomeric salts (Va to Vd) is conducted as follows:

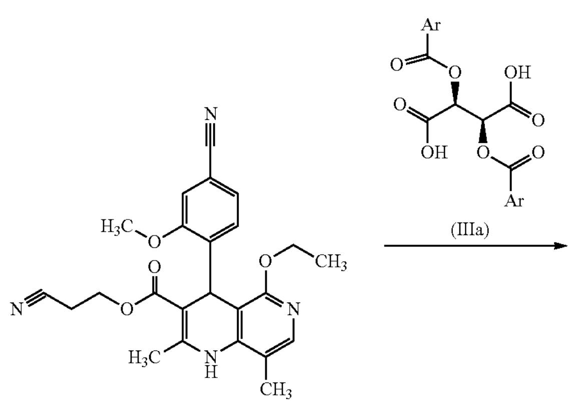

racemic
(IV)

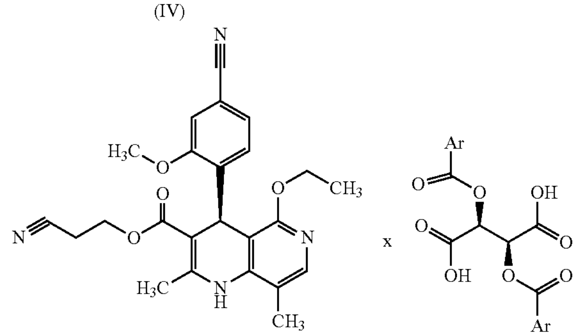

(Va)

-continued

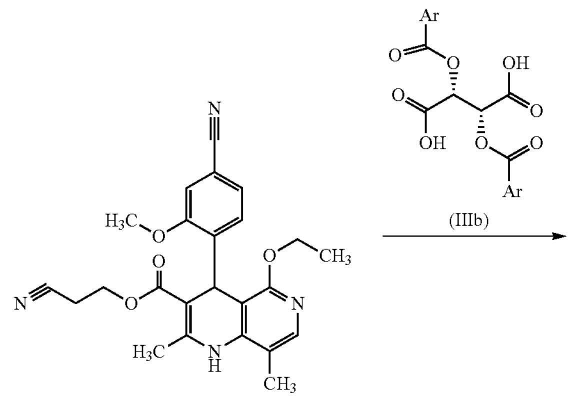

racemic
(IV)

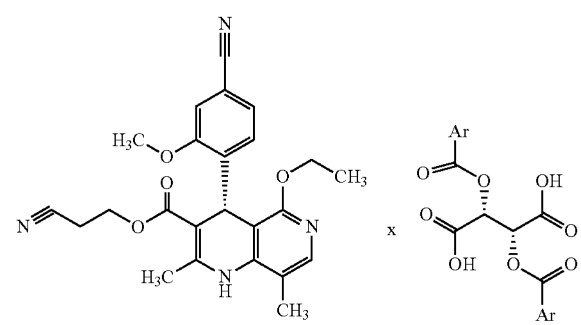

(Vb)

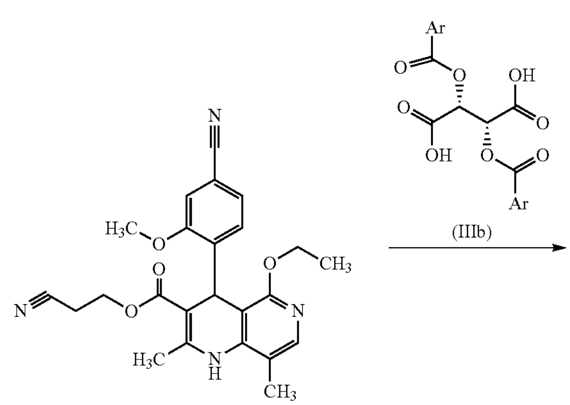

racemic
(IV)

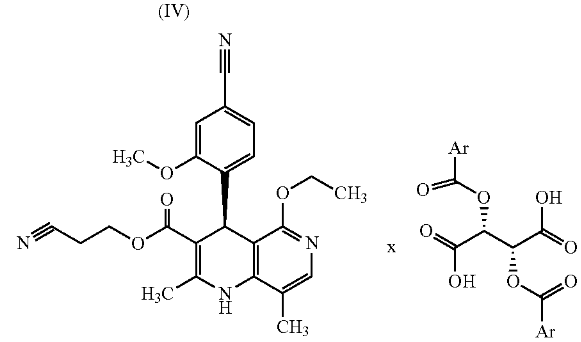

(Vc)

-continued

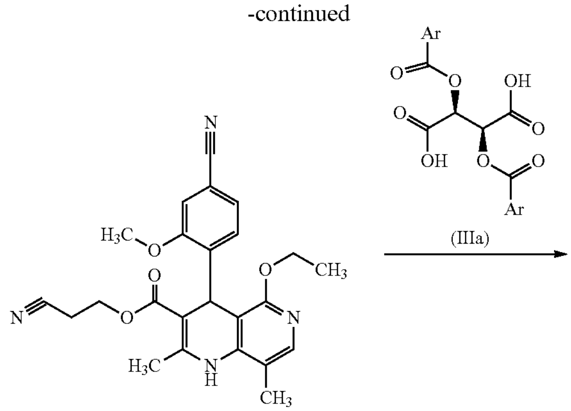

racemic
(IV)

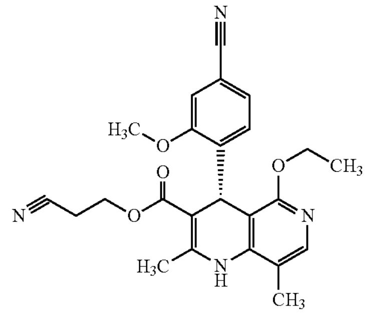

x

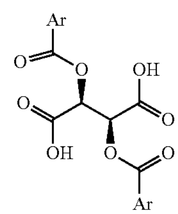

(Vd)

The reaction of the racemic mixture (IV) with a tartaric acid derivative of the general formula (IIIa) or (IIIb) results in 4 options for diastereomeric salt formation (V a-d). Surprisingly, a preference is observed such that if rac-(IV), for example, is reacted with a tartaric acid derivative of the general formula (IIIa), what is obtained is the diastereomeric salt of the general formula (Va), with the antipode of S configuration preferentially entering into salt formation. The diastereomeric salt (Va) precipitates virtually quantitatively out of the solution, from which it can then be isolated, for example by filtration, with the antipode having R configuration remaining in solution. In a very similarly surprising manner, the mirror-image salt of the general formula (Vb) is prepared by reacting the racemate (II) with the tartaric acid derivative of the general formula (IIIb), with the antipode of R configuration preferentially entering into salt formation. The precipitated diastereomeric salts can be separated off nearly quantitatively, and here the S-enantiomer remains in solution.

The stoichiometric ratio of (IV) to (IIIa)/(IIIb) and the selection of solvent can be used to optimize yield and enantiomeric purity.

Finerenone (I) has S configuration. Either S,S-configured or R,R-configured tartaric esters (according to substitution type) can form diastereomeric salts with the 4S-configured enantiomer of the racemate IV.

0.5 to 2.0 equivalents of tartaric ester (IIIa) or (IIIb) are used for the optical resolution, but preferably 0.7 to 1.5 equivalents, but more preferably 0.7 to 1.4 equivalents, but most preferably 0.70-1.2 equivalents. Diastereomeric salts are formed in organic solvents or solvent mixtures consisting of water and water-miscible organic solvents.

Examples of suitable organic solvents in the context of the application include ethanol, methanol, isopropanol, 1-propanol, ethyl acetate, isobutanol, dichloromethane, 1-pentanol or acetone, but preference is given to using ethanol. The solvents may also be used in the commercial denatured form, such as the denaturing agents used in the case of ethanol, for example toluene, methyl ethyl ketone, thiophene, hexane, which also brings great advantages for reasons of cost; therefore, spirits are suitable, especially for industrial scale use, which, in the context of the application, consist of ethanol that may optionally have been denatured with toluene or methyl ethyl ketone. Thus, where reference is made to "spirits", this means denatured ethanol. The term "spirits" is known to those skilled in the art. In addition, the following solvents were also used: ethyl acetate/methanol 90:10; methanol/water 80:20; ethanol/water 90:10; ethanol/water 85:15; ethanol/water 80:20; ethanol/water 75:25; ethanol/water 70:30; dichloromethane; 1-propanol/water 80:20; 1-pentanol; 1-pentanol/water 90:10; isopropanol; isopropanol/water 80:20; isobutanol/water 90:10; isobutanol/water 80:20; cyclohexanol/water 90:10; benzyl alcohol/water 90:10; ethylene glycol; ethylene glycol/water 80:20. In the figures for the solvent ratios, the ratio means volume to volume (v/v). A solvent mixture consisting of, for example, methanol/water 80:20 contains 80 ml of ethanol and 20 ml of water. The volume is thus based on the total volume of the solvent.

Preference is given to conducting the optical resolution in ethanol/water, where the mixing ratio (v/v) is in the range of ethanol:water=1:1 to 6:1. But preference is given to using a mixture of ethanol:water=6:1 to 3:1. Particular preference is given to a mixture of ethanol:water=3:1. The mixture can be prepared beforehand, or else be produced in situ, after a pot has been charged with all the components. The solvent mixture may be used in a 10- to 60-fold excess, based on the racemate (IV), i.e. 10 l to 40 l of solvent mixture is used per 1 kg of racemate. Preference is given to a 10- to 50-fold excess.

The optical resolution is typically effected by first initially charging all the components in the solvent mixture at room temperature, then heating to 10 to 60° C., but preferably to 20-50° C., and continuing to stir at 20-50° C. for 1 to 10 hours, preferably 1 to 4 hours, and then cooling down to room temperature (about 20-23° C.) within 3 to 24 hours, preferably 5 to 16 hours. Thereafter, stirring is continued at room temperature for 2 to 24 hours, preferably 5-18 hours, very preferably 12-16 hours. Optical resolution is preferably effected at a temperature of 20° C.-50° C.

This is followed by the isolation of the precipitated diastereomeric salt (Va), (Vb), (Vc) and/or (Vd).

The isolation is carried out by methods known to the person skilled in the art, for example by filtration or using a centrifuge. The filter cake obtained in this manner can be washed once or several times with a solvent or solvent mixture. This is followed by drying under reduced pressure, preferably <100 mbar, at elevated temperature (50-80° C., preferably 50° C.). In some cases, the use of a carrier gas has been found to be advantageous.

By the procedure outlined above, it is possible to prepare diastereomeric salts having an enantiomeric excess of the diastereomeric salts in the range from 65% to 80% e.e.

For further purification to increase the enantiomeric excess, extractive stirring from a solvent or solvent-water mixture is repeated.

The diastereomeric salts need not necessarily be dried, but may also be used moist in the next process stage.

Examples of suitable organic solvents in the context of the application include ethanol, methanol, isopropanol, 1-propanol, ethyl acetate, isobutanol, dichloromethane, 1-pentanol or acetone, but preference is given to using ethanol. The solvents may also be used in the commercially available denatured form, such as the denaturing agents used for ethanol, for example toluene, methyl ethyl ketone, thiophene, hexane, which brings great advantages for reasons of cost. Therefore, especially for use on an industrial scale, spirits is suitable, which, in the context of the application, consists of ethanol that may optionally be denatured with toluene or methyl ethyl ketone. In addition, the following solvents were also used: ethyl acetate/methanol 90:10; methanol/water 80:20; ethanol/water 90:10; ethanol/water 85:15; ethanol/water 80:20; ethanol/water 75:25; ethanol/water 70:30; dichloromethane; 1-propanol 30/water 80:20; 1-pentanol; 1-pentanol/water 90:10; isopropanol; isopropanol/water 80:20; isobutanol/water 90:10; isobutanol/water 80:20; cyclohexanol/water 90:10; benzyl alcohol/water 90:10; ethylene glycol; ethylene glycol/water 80:20. In the figures for the solvent ratios or mixing ratios, the ratio means volume to volume (v/v). A solvent mixture consisting of, for example, methanol/water 80:20 contains 80 ml of ethanol and 20 ml of water.

Preference is given to conducting the optical resolution in ethanol/water, where the mixing ratio (v/v) is in the range of ethanol:water=1:1 to 6:1. But preference is given to using a mixture of ethanol:water=6:1 to 3:1. Particular preference is given to a mixture of ethanol:water=3:1. The mixture may have been prepared beforehand, or else produced in situ after a pot has been charged with all the components. The solvent mixture may be used in a 10- to 60-fold excess, based on the racemate (IV), i.e. 10 l to 40 l of solvent mixture is used per 1 kg of racemate. Preference is given to a 10- to 50-fold excess.

The extractive stirring is typically effected by first initially charging all the components in the solvent mixture at room temperature, then heating to 10 to 60° C., but preferably to 20-50° C., and continuing to stir at 20-50° C. for 1 to 10 hours, preferably 1 to 4 hours, and then cooling down to room temperature (about 20-23° C.) within 3 to 24 hours, preferably 5 to 16 hours. Thereafter, stirring is continued at room temperature for 2 to 24 hours, preferably 5-18 hours, very preferably 12-16 hours.

This is followed by the isolation of the precipitated diastereomeric salt (Va) or (Vb) or (Vc) and/or (Vd).

The isolation is carried out by methods known to the person skilled in the art, for example by filtration or using a centrifuge. The filter cake obtained in this manner can be washed once or several times with a solvent or solvent mixture. This is followed by drying under reduced pressure, preferably <100 mbar, at elevated temperature (50° C.-80° C., preferably 50° C.). In some cases, the use of a carrier gas has been found to be advantageous. The diastereomeric salts thus obtained are notable for a high enantiomeric excess, generally >95% e.e., which is sufficient to prepare finerenone in >>99% e.e.

The diastereomeric salts need not necessarily be dried, but may also be used moist in the next process stage.

In addition to the customary procedure mentioned above, the process steps may also be combined or their sequence may be changed, as shown in Table 2 below:

TABLE 2

| 1. Step | 2. Step | 3. Step | 4. Step | 5. Step |
|---|---|---|---|---|
| initial charging of racemate (IV) and diaryltartaric acid (IIIa or b) | addition of ethanol | addition of water | heating | |
| initial charging of racemate (IV) | addition of ethanol | addition of diaryltartaric acid (IIIa or b) | addition of water | heating |
| initial charging of racemate (IV) | addition of water | addition of diaryltartaric acid (IIIa or b) | addition of ethanol | heating |
| initial charging of diaryltartaric acid (IIIa or b) | addition of ethanol | addition of racemate (IV) | addition of water | heating |
| initial charging of diaryltartaric acid (IIIa or b) | addition of water | addition of racemate (IV) | addition of ethanol | heating |
| initial charging of racemate (IV) and diaryltartaric acid (IIIa or b) | addition of the ethanol/water mixture | heating | | |
| initial charging of racemate (IV) | addition of the ethanol/water mixture | addition of diaryltartaric acid (IIIa or b) | addition of ethanol | heating |
| initial charging of diaryltartaric acid (IIIa or b) | addition of the ethanol/water mixture | addition of racemate (IV) | addition of water | heating |
| initial charging of the ethanol/water mixture | addition of racemate (IV) | addition of diaryltartaric acid (IIIa or b) | heating | |
| initial charging of the ethanol/water mixture | addition of diaryltartaric acid (IIIa or b) | addition of racemate (IV) | heating | |
| initial charging of ethanol | addition of racemate (IV) | addition of water | addition of diaryltartaric acid (IIIa or b) | heating |
| initial charging of water | addition of racemate (IV) | addition of ethanol | addition of diaryltartaric acid (IIIa or b) | heating |
| initial charging of ethanol | addition of diaryltartaric acid (IIIa or b) | addition of water | addition of racemate (IV) | heating |

TABLE 2-continued

| 1. Step | 2. Step | 3. Step | 4. Step | 5. Step |
|---|---|---|---|---|
| initial charging of water | addition of diaryltartaric acid (IIIa or b) | addition of ethanol | addition of racemate (IV) | heating |

Depending on the type of plant in the pilot plant, or in the production, one variant or the other may be advantageous.

In the next step, the diastereomeric salt is treated with a base, and the solvent is removed. The solvent is removed by methods known to the person skilled in the art, for example by distillative removal. For preparation of the chiral compounds (IVa) and (IVb), the diastereomeric salt of the general formula (Va), (Vb), (Vc) or (Vd) has to be treated with a base; distillative removal of the organic solvent precipitates the target molecule (IVa) or (IVb) out of the solution, which is isolated—for example by filtering-off and washing on the filter—and the respective tartaric ester of formula (IIIa) or (IIIb) remains in solution in the form of a salt.

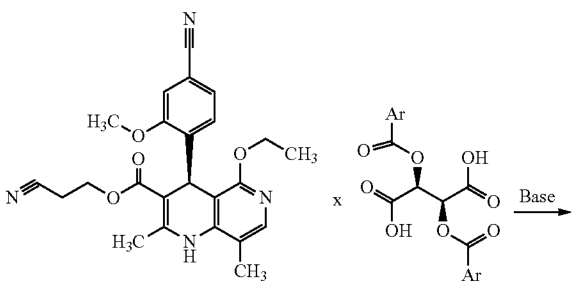

(Va)

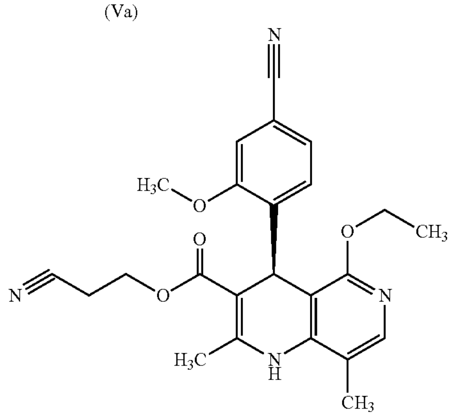

(IVa)

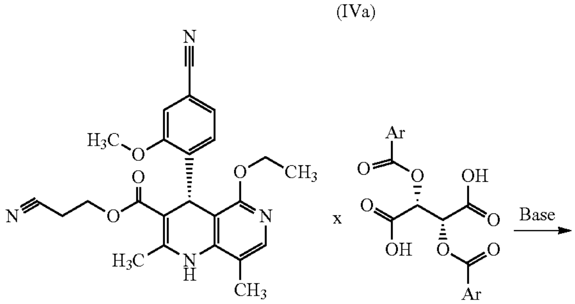

(Vb)

-continued

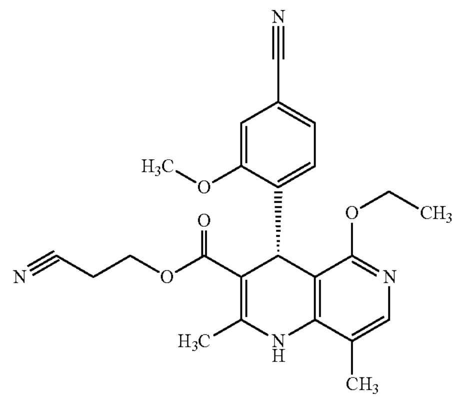

(IVb)

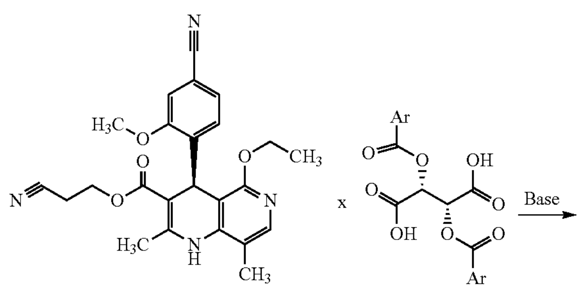

(Vc)

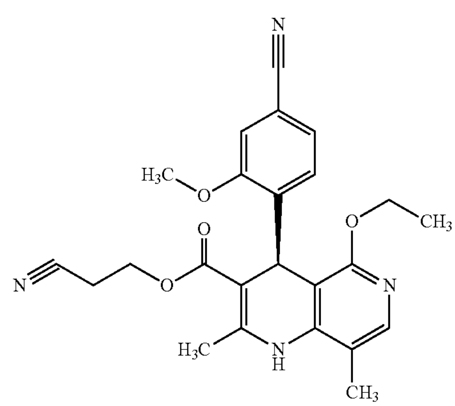

(IVa)

-continued

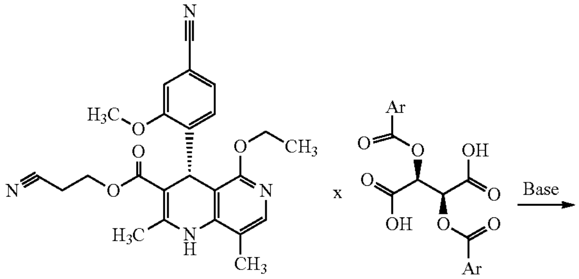

(Vd)

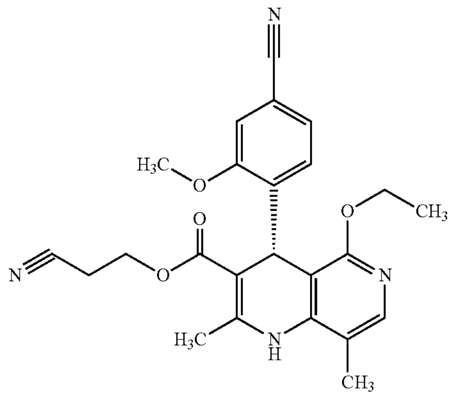

(IVb)

Suitable bases in the context of the present invention are inorganic and organic bases. In the case of inorganic bases, it is possible to use ammonia, aqueous sodium hydroxide solution, lithium hydroxide, potassium hydroxide, ammonium carbonate, sodium carbonate, potassium carbonate, lithium carbonate, ammonium hydrogencarbonate, sodium hydrogencarbonate, potassium hydrogencarbonate, sodium phosphate, potassium phosphate, ammonium phosphate. However, preference is given to using sodium hydroxide, sodium phosphate or potassium phosphate. Particular preference is given to using sodium phosphate or potassium phosphate. It is important to emphasize that the inorganic bases may be used either in anhydrous form or in the form of their hydrates; for example, sodium phosphate (anhydrous) and sodium phosphate hydrate may be used successfully. The organic base used may be aliphatic or aromatic bases, for example triethylamine, imidazole, N-methylimidazole, Hunig's base, pyridine, DBU.

The target compound (IVa) or (IVb) is released in mixtures of water water-miscible organic solvents such as ethanol, isopropanol, ethane-1,2-diol, methoxyethanol, methanol or acetone, preference being given to ethanol. The solvents may also be used in the commercial denatured form, such as the denaturing agents used in the case of ethanol, for example toluene, methyl ethyl ketone, thiophene, hexane; preference is given to using spirits which, in the context of the application, consist of ethanol that may optionally have been denatured with toluene or methyl ethyl ketone, which brings great advantages for reasons of cost. It has been found to be advantageous to use mixtures of water and ethanol, with the mixing ratio (v/v) in the range of ethanol:water=1:6 to 1:3. But preference is given to using a mixture of ethanol:water=1:3. The mixture may have been prepared beforehand, or else produced in situ after a pot has been charged with all the components. This mixture may be used in an amount 7 to 20 times that of the diastereomeric salt (IVa or IVb or IVc or IVd) used, i.e., for example, 1 kg in 7 l to 20 l of this mixture. Preference is given to using 8 to 15 times the amount of this mixture, more preferably 9 to 11 times the amount of this mixture, most preferably 10 times the amount of this mixture. The target compound (IVa) or (IVb) is released by initially charging the diastereomeric salt (Va or Vb or Vc or Vd) in a solvent mixture at 0° C. to 60° C., preferably 0° C. to 50° C., followed by addition of the organic or inorganic base (either in solid form or as a solution, preferably in water) to establish a pH to 6.9 to 8.0, preferably a pH of 7.0 to 7.5, more preferably pH 7.1. Suitable bases in the context of the present invention are inorganic and organic bases. In the case of inorganic bases, it is possible to use ammonia, aqueous sodium hydroxide solution, lithium hydroxide, potassium hydroxide, ammonium carbonate, sodium carbonate, potassium carbonate, lithium carbonate, ammonium hydrogencarbonate, sodium hydrogencarbonate, potassium hydrogencarbonate, sodium phosphate, potassium phosphate, ammonium phosphate. However, preference is given to using sodium hydroxide, sodium phosphate or potassium phosphate. Particular preference is given to using sodium phosphate or potassium phosphate. It is important to emphasize that the inorganic bases may be used either in anhydrous form or in the form of their hydrates; for example, sodium phosphate (anhydrous) and sodium phosphate hydrate may be used successfully. The organic base used may be aliphatic or aromatic bases, for example triethylamine, imidazole, N-methylimidazole, Hünig's base, pyridine, DBU.

The base can be added either very quickly (within a few minutes) or else very slowly (within a few hours), for example within 5 minutes up to 3 hours. Faster addition is preferred in any case. Preference is given to metered addition within 5 min to 1 hour. This purpose may be served by a pH meter installed in the reactor, with which the adjustment is controlled and the base is gradually metered in. It is alternatively possible to add a fixed amount of base (in solid form or dissolved in a solvent) at the start, which, based on experience, ensures that the desired pH range is preferentially attained. In production, such a procedure is most preferred. It has been found to be advantageous to continue stirring after the pH has been established, again at 0° C.-50° C., preferably 20° C.-50° C., preferably 0° C.-20° C. The period of continued stirring may be 1 to 10 hours, preferably 2-5 hours, more preferably 3-4 hours.

The isolation is carried out by methods known to the person skilled in the art, for example by filtration or using a centrifuge. The filter cake obtained in this manner can be washed once or more than once with a solvent or solvent mixture. This is followed by drying under reduced pressure, preferably <100 mbar, at elevated temperature (50-80° C., preferably 50° C.). In some cases, the use of a carrier gas has been found to be advantageous.

As a particularly preferred process, especially for implementation on an industrial scale, di-p-tolyl-D-tartaric acid (IIIa') is used, which may be used either in anhydrous form or in hydrate form:

-continued
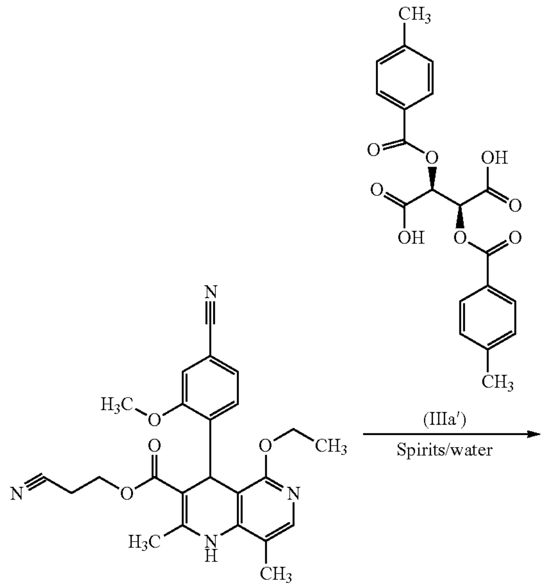
racemic (IV)
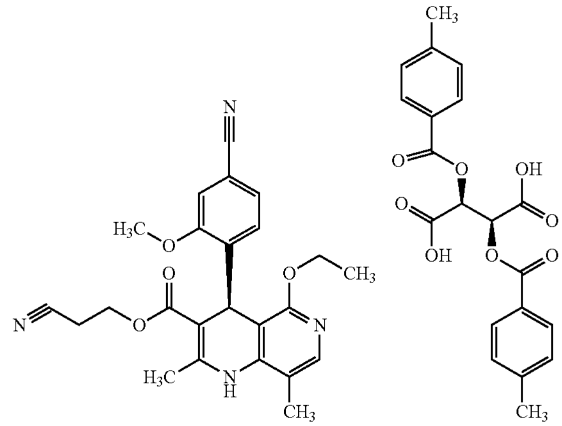
(IVa')
The optical resolution is preferably carried out in a spirits/water mixture. The subsequent release of (IVa)
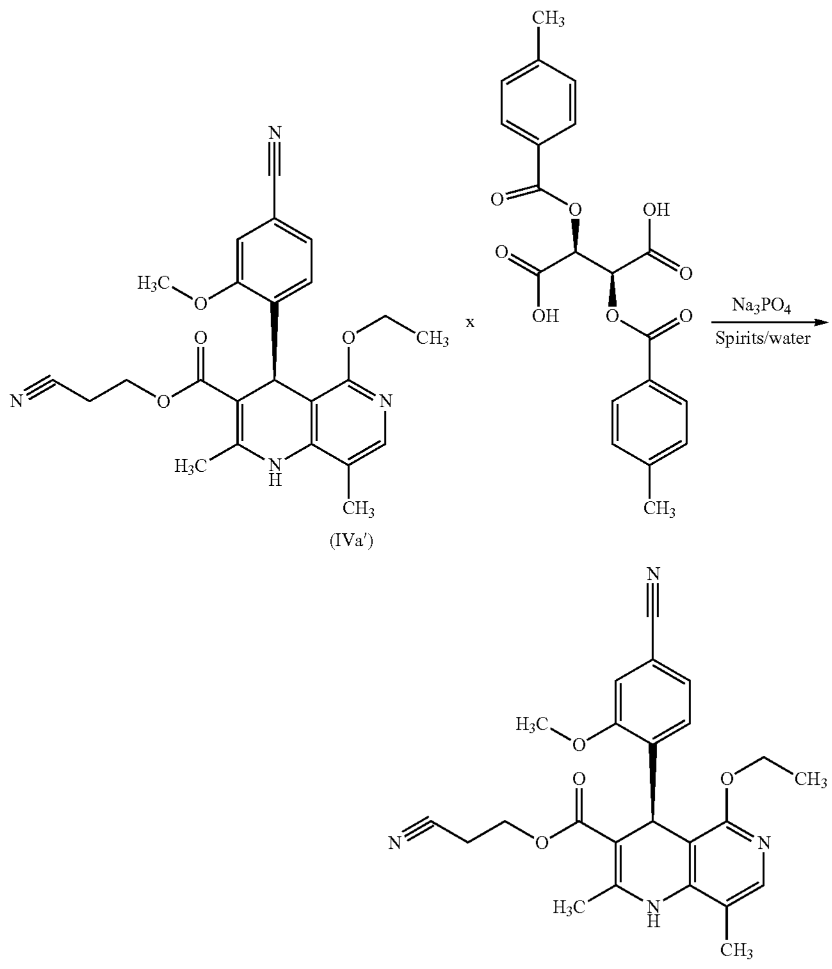
(IVa')
(IVa)

is preferably effected in a spirits/water mixture using sodium phosphate as base.

It is also possible to isolate the target enantiomer from the mother liquor. First of all, the appropriate diastereomeric salt (Va), (Vb), (Vc) or (Vd) is prepared here either from (IVa) or (IVb), then isolated by filtration, and then the pH of the mother liquor comprising the respective antipode is then adjusted to pH>7, preferably pH 7.1-8, most preferably pH 7.1, by addition of a base, for example ammonia, sodium hydroxide solution, lithium hydroxide, potassium hydroxide, ammonium carbonate, sodium carbonate, potassium carbonate, lithium carbonate, ammonium hydrogencarbonate, sodium hydrogencarbonate, potassium hydrogencarbonate, sodium phosphate, potassium phosphate, ammonium phosphate, preferably sodium hydroxide, sodium phosphate and potassium phosphate, more preferably sodium phosphate and potassium phosphate. Subsequently, the organic solvent—preferably ethanol—is distilled off, either at atmospheric pressure or, more gently, under reduced pressure. This precipitates the corresponding antipode. The product is filtered off, washed with water or water/solvent mixtures and dried. An appropriate final crystallization from spirits as described, for example, in Example 1c affords the compounds (IVa) and (IVb) in correspondingly pure form.

The further conversion to finerenone (Ia), or the antipode (Ib), is conducted as follows:

Proceeding from the cyanoethyl ether (IVa or IVb), the acid (VIIa or VIIb) is obtained by alkaline hydrolysis and subsequent acidic workup:

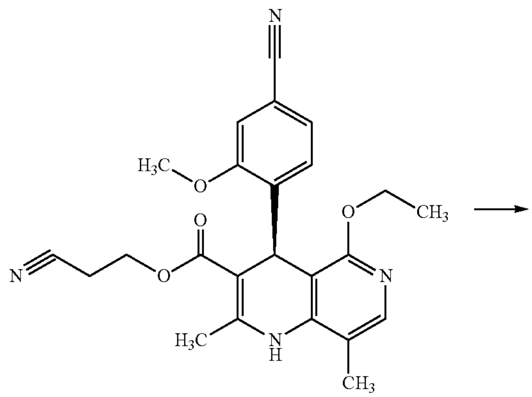

(IVa)

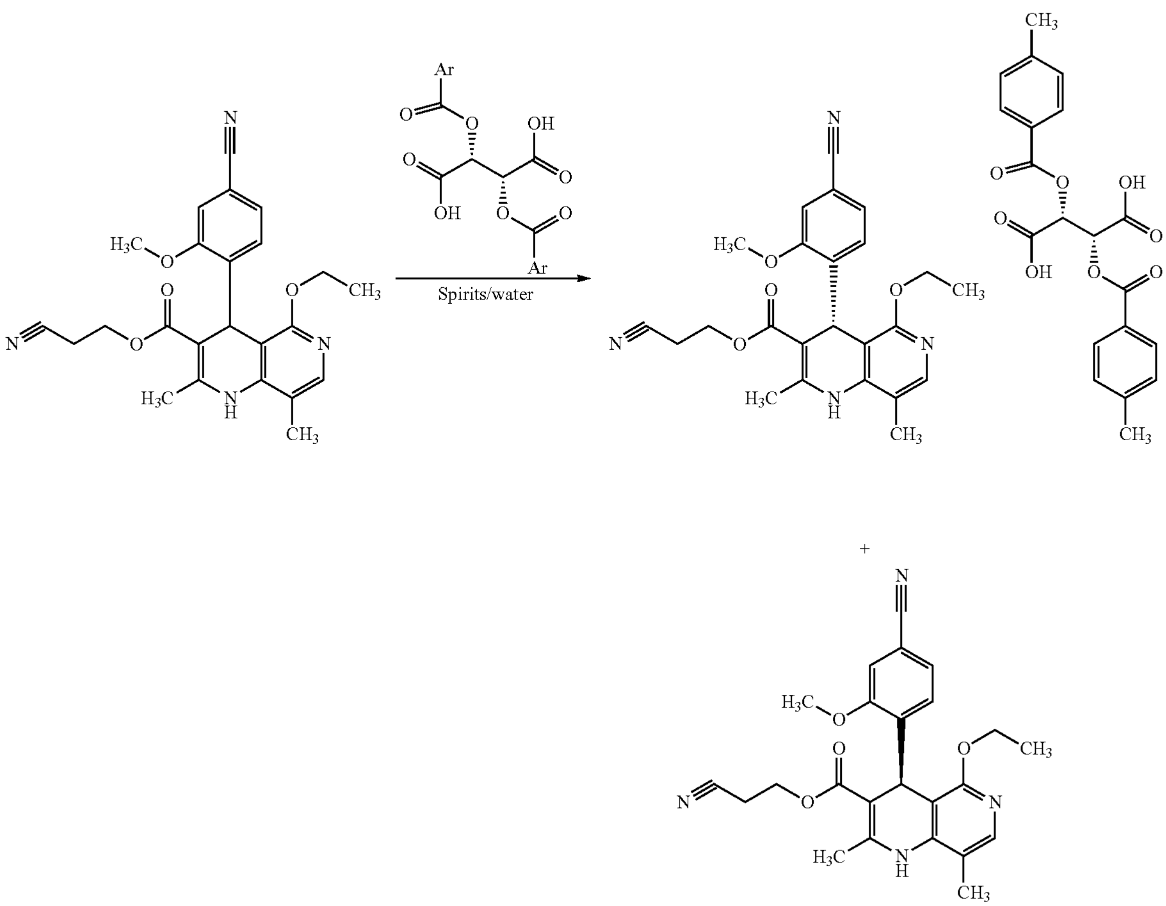

(IVa) in mother liquor

-continued

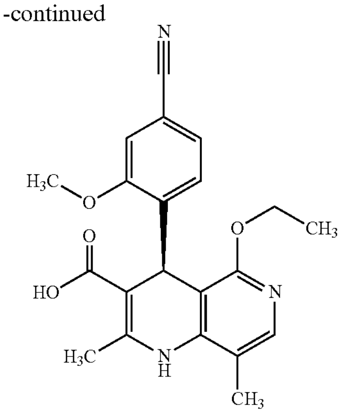

(VIIa)

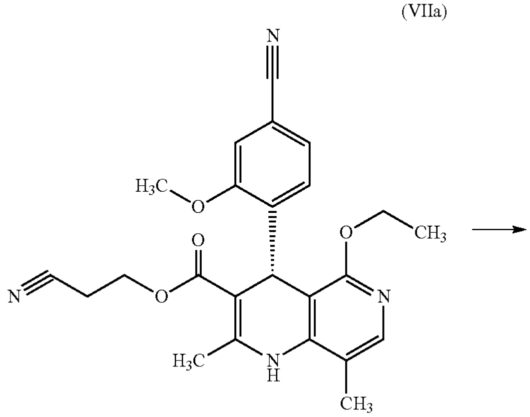

(IVb)

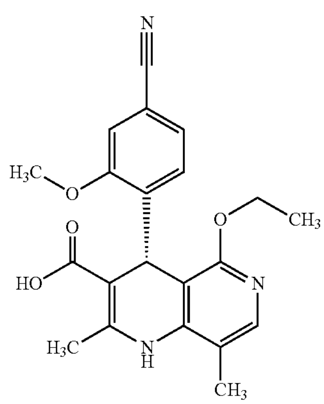

(VIIb)

It has been found that the reaction can be run very easily in relatively concentrated form in mixtures of THF/water. For this purpose, preference is given to working in a mixture of THF/water 2:1 (9 times the amount), metering in the aqueous sodium hydroxide solution at 0° C.-5° C., then stirring the mixture at 0° C.-5° C. for 1-2 hours. It is also possible to use potassium hydroxide solution, but preference is given to sodium hydroxide solution. Workup is effected by extracting with MTBE (methyl tert-butyl ether) and ethyl acetate or else toluene only, and isolation by adjusting the pH to 7 with a mineral acid such as hydrochloric acid, sulfuric acid or phosphoric acid, but preferably hydrochloric acid. It is then possible to add saturated ammonium salt solution of the corresponding acid, but preferably ammonium chloride solution, with quantitative crystallization of the product. After isolation, the product is washed with water and with ethyl acetate or with acetonitrile or with acetone, but preferably with acetonitrile, and dried under vacuum at 40° C.-50° C. The yield is virtually quantitative (99%).

The subsequent conversion of the acid to the amide (I or Ia) is described as follows: It has been found that, in a conversion of the acid (VIIa or VIIb) in tetrahydrofuran (THF), the amide (I or Ia) crystallizes directly out of the solution and can be obtained in high yield and purity. For this purpose, the carboxylic acid (VIIa or VIIb) is reacted with 1.1 to 1.6 equivalents, preferably 1.3-1.4 equivalents, of 1,1'-carbodiimidazole (CDI) under 4-(dimethylamino) pyridine (DMAP) catalysis (5-15 mol %, preferably mol %/in some cases it has been found that the reaction can also be conducted without addition of DMAP) in THE at temperatures between 20-50° C. (the preferred approach has been found to be first to start at 20° C., then stir at that temperature 1 to 2 hours and then continue stirring at 50° C. for 2 to 3 hours) to give the imidazolide. After the activation has ended, 3-8 equivalents, preferably 4.5 equivalents, of hexamethyldisilazane are added and the mixture is heated for 16-24 hours, but preferably for 16 hours, under reflux. The disilylamide compound formed here can optionally be isolated. However, it has been found to be more advantageous to continue in a one-pot reaction. After the reaction has ended, therefore, the mixture is cooled to 0° C.-3° C. and water or a mixture of water/THF is metered in. An advantageous amount of water has been found to be 0.5 to 0.7 times the amount of the reactants, and a particularly advantageous amount to be 0.52 times the amount of water. The water can be added directly or as a mixture with about one to two volume equivalents of THF. After quenching has ended, the mixture is heated to reflux for a total of 1-3 hours, preferably 1 hour. The mixture is cooled to 0° C. and stirred at that temperature for a further 1-5 hours, preferably 3 hours. Subsequently, the product is isolated by filtration or centrifugation. The product is washed with THE and water and dried under vacuum at elevated temperature (30° C. to 100° C., preferably at 40° C. to 70° C.). The yields are very high and are >93% of theory. The purity is generally >99% (HPLC, 100% method). The compound (VIIa or VIIb) can also be obtained directly by reacting with ammonia gas in an autoclave (about 25 to 30 bar). For this purpose, the preactivation described above is carried out and the reaction mixture is then heated under pressure under gaseous ammonia. On completion of the reaction, it is cooled and the product filtered off. The yields and purities thus achieved are comparable.

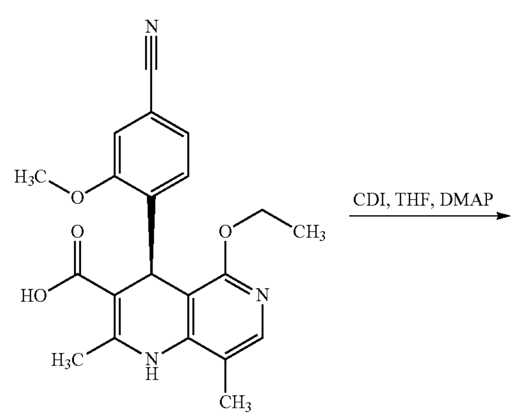

(VIIa)

-continued

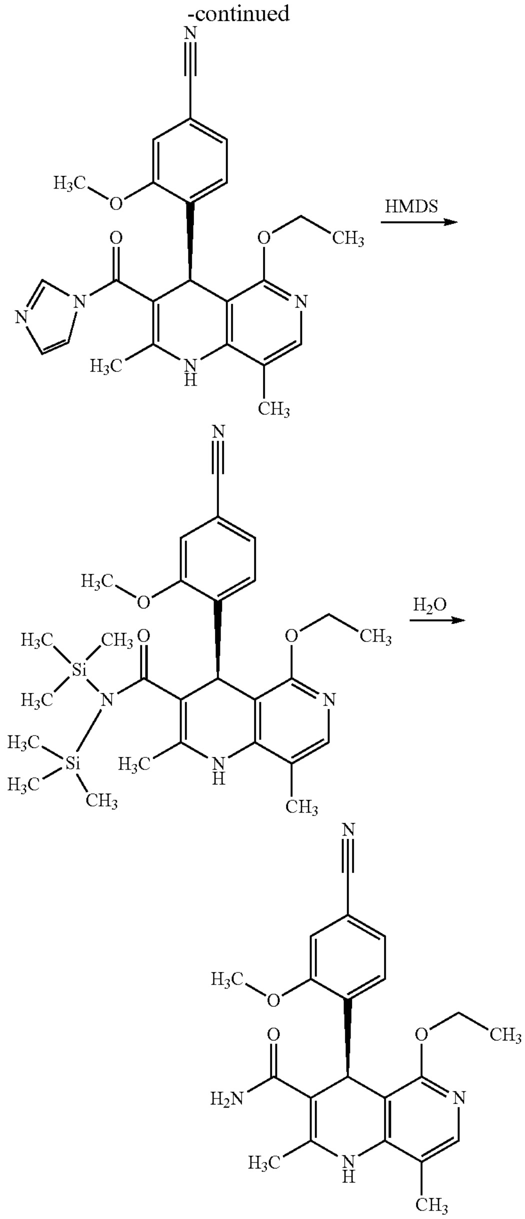

(Ia)

Final crystallization method (establishment of the final modification Mod A): For this purpose, (I) (or Ia), for GMP-related reasons, is first dissolved in ethanol and subjected to a particle filtration, and then the solvent is distilled off, either under reduced pressure or at standard temperature, preference being given to using toluene-denatured ethanol. The mixture is concentrated to about 3 to 5 times the volume of (I) (or Ia); the product crystallizes out. The mixture is cooled to 0° C. and the crystals then isolated and dried at 40° C.-50° C. under reduced pressure. The yields are generally >90% of theory. The chemical purity achieved is >99.8% and the content ~100% correspond to the criteria for commercial products according to ICH guidelines. Residual solvent, in the case of ethanol, is <0.02%. The optical purity is >>99% e.e.

The present invention therefore also relates to a process for preparing (4S)-4-(4-cyano-2-methoxyphenyl)-5-ethoxy-2,8-dimethyl-1,4-dihydro-1,6-naphthyridine-3-carboxamide of the formula (Ia)

(Ia)

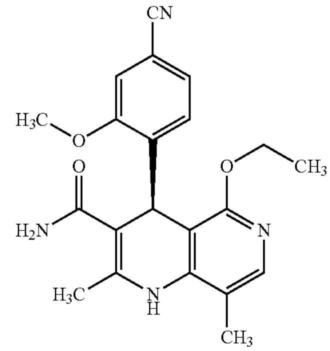

characterized in that enantiomerically pure cyanoethanol ester 2-cyanoethyl (4S)-4-(4-cyano-2-methoxyphenyl)-5-ethoxy-2,8-dimethyl-1,4-dihydro-1,6-naphthyridine-3-carboxylate of the formula (IVa)

(IVa)

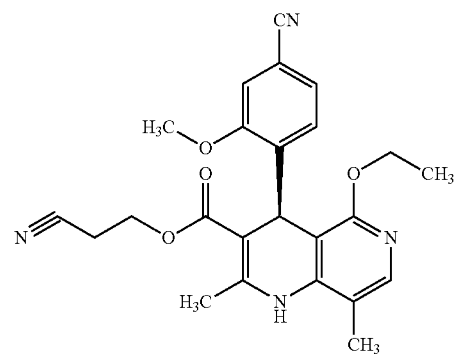

is hydrolysed in a THF/water mixture (2:1) with sodium hydroxide solution to give the compound of the formula (VIIa)

(VIIa)

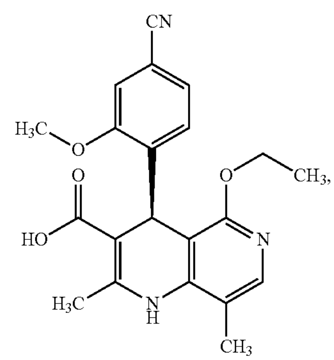

and the latter is then reacted in THF as solvent firstly with 1,1-carbodiimidazole and catalytic amounts of 4-(dimethylamino)pyridine, hexamethyldisilazane is added and then the mixture is heated under reflux for 16-24 hours, and then a THF/water mixture is added.

There follows a description of further embodiments of the invention:

The present invention relates to a process for preparing 2-cyanoethyl (4S)-4-(4-cyano-2-methoxyphenyl)-5-ethoxy-2,8-dimethyl-1,4-dihydro-1,6-naphthyridine-3-carboxylate of the formula (IVa)

(IVa)

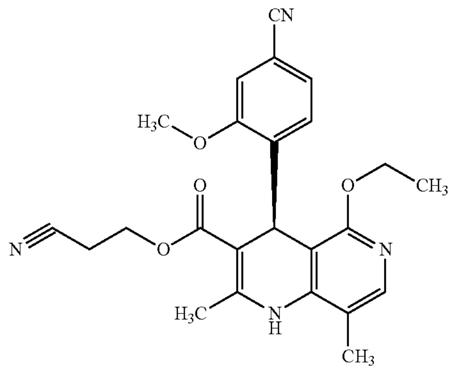

by optical resolution of racemic 2-cyanoethyl (4S)-4-(4-cyano-2-methoxyphenyl)-5-ethoxy-2,8-dimethyl-1,4-dihydro-1,6-naphthyridine-3-carboxylate of the formula (IV)

(IV)

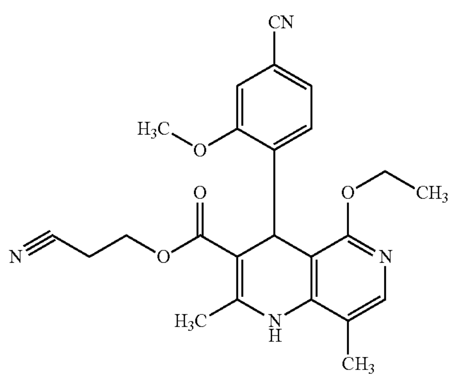

using a chiral substituted tartaric ester of the formula (IIIa)

(IIIa)

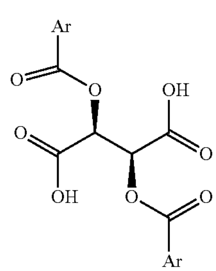

where Ar is unsubstituted or substituted aryl or heteroaryl.

Preference is given to a process for preparing 2-cyanoethyl (4S)-4-(4-cyano-2-methoxyphenyl)-5-ethoxy-2,8-dimethyl-1,4-dihydro-1,6-naphthyridine-3-carboxylate of the formula (IVa)

(IVa)

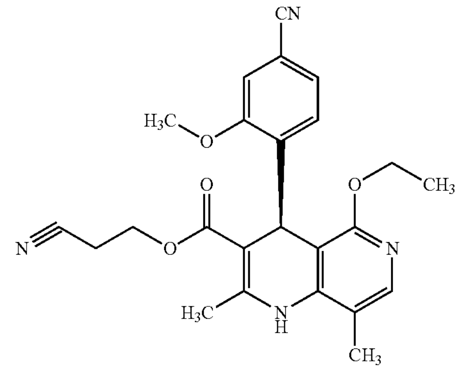

by optical resolution of racemic 2-cyanoethyl (4S)-4-(4-cyano-2-methoxyphenyl)-5-ethoxy-2,8-dimethyl-1,4-dihydro-1,6-naphthyridine-3-carboxylate of the formula (IV)

(IV)

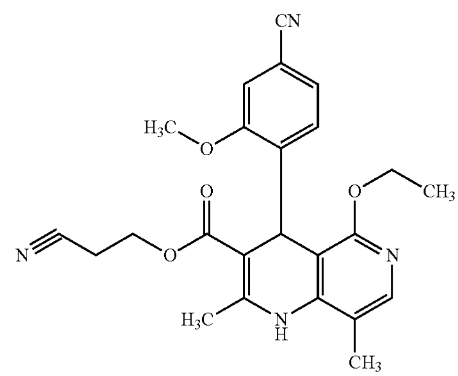

using a chiral substituted tartaric ester of the formula (IIIa)

(IIIa)

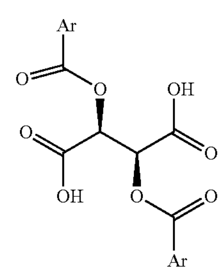

where Ar is

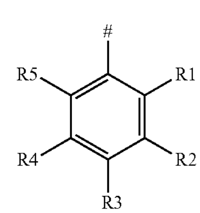

where #represents the site of attachment, where R1, R2, R3, R4, R5 are each a hydrogen atom or an alkyl radical, for example methyl, ethyl, propyl, or a halogen atom, for example fluorine, chlorine, bromine or iodine, or an ether group, for example O-methyl, O-ethyl, O-phenyl, or a nitro group, or a cyano group, or a CF3 group, or an amide group, for example —NHCOR in which R may be methyl, ethyl or phenyl, or —NRCOR in which R has the meaning given above or CONHR— in which R has the meaning given above or CONRR' group in which R' has the same meaning as R as defined above, or cyclic amides such as 3-oxomorpholin-4-yl, 2-oxopiperidin-1-yl, which may in turn be substituted. The substitution patterns may differ widely; for instance, up to 5 different substituents are theoretically possible, but preference is generally given to the monosubstituted Ar radicals. Ar may alternatively be a substituted heteroaromatic radical such as, preferably, pyridine or pyrazine. Ar may alternatively be a polycyclic aromatic hydrocarbon, for example a substituted naphthalene, anthracene or quinoline.

Preference is given to a process for preparing 2-cyanoethyl (4S)-4-(4-cyano-2-methoxyphenyl)-5-ethoxy-2,8-dimethyl-1,4-dihydro-1,6-naphthyridine-3-carboxylate of the formula (IVa) where Ar is one of the formulae

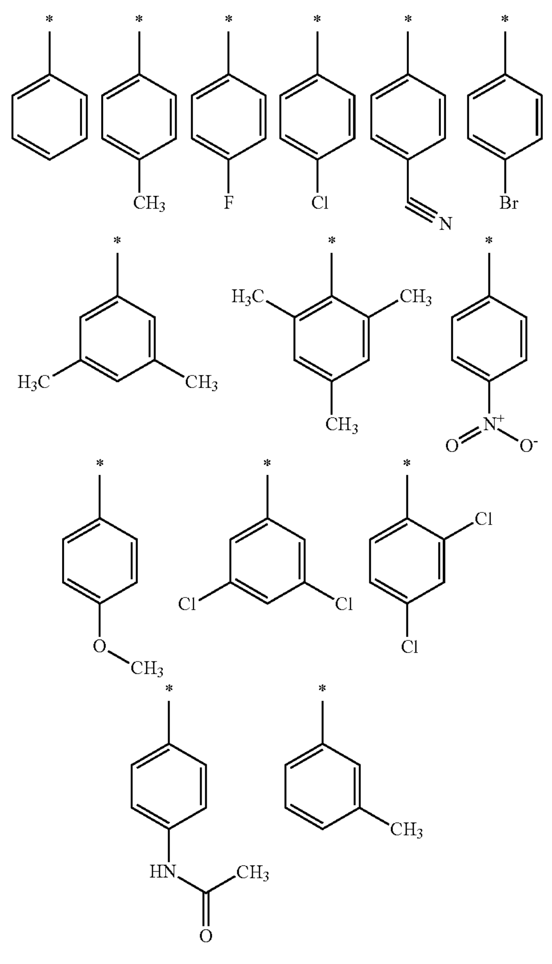

in which * represents the site of attachment.

Particular preference is given to a process for preparing 2-cyanoethyl (4S)-4-(4-cyano-2-methoxyphenyl)-5-ethoxy-2,8-dimethyl-1,4-dihydro-1,6-naphthyridine-3-carboxylate of the formula (IVa)

where

Ar is one of the formulae

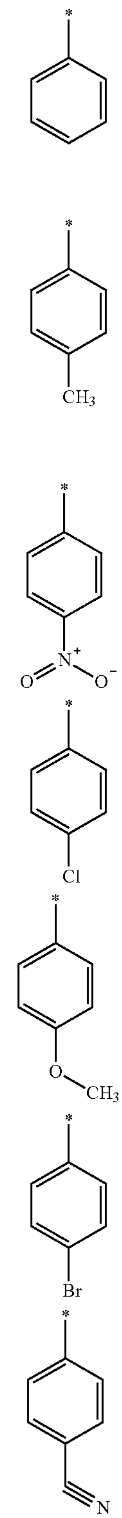

-continued

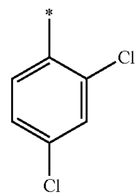

in which * represents the site of attachment.

Especial preference is given to a process for preparing 2-cyanoethyl (4S)-4-(4-cyano-2-methoxyphenyl)-5-ethoxy-2,8-dimethyl-1,4-dihydro-1,6-naphthyridine-3-carboxylate of the formula (IVa)

where

Ar is one of the formulae

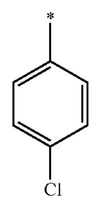

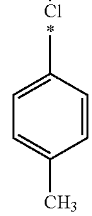

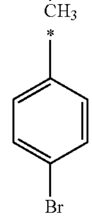

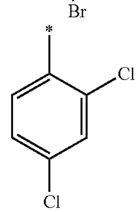

in which * represents the site of attachment.

Especial preference is given to a process for preparing 2-cyanoethyl (4S)-4-(4-cyano-2-methoxyphenyl)-5-ethoxy-2,8-dimethyl-1,4-dihydro-1,6-naphthyridine-3-carboxylate of the formula (IVa)

where

Ar is one of the formulae

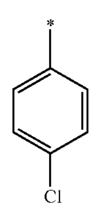

-continued

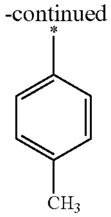

in which * represents the site of attachment.

Very particular preference is given to a process for preparing 2-cyanoethyl (4S)-4-(4-cyano-2-methoxyphenyl)-5-ethoxy-2,8-dimethyl-1,4-dihydro-1,6-naphthyridine-3-carboxylate of the formula (IVa)

where

Ar is

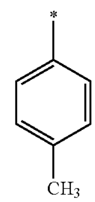 [SMILES: *c1ccc(C)cc1]

in which * represents the site of attachment.

The present invention also relates to a process for preparing (4S)-4-(4-cyano-2-methoxyphenyl)-5-ethoxy-2,8-dimethyl-1,4-dihydro-1,6-naphthyridine-3-carboxamide of the formula (Ia)

(Ia)

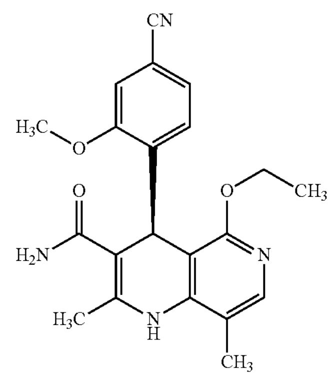

characterized in that racemic cyanoethanol ester of the formula (IV)

(IV)

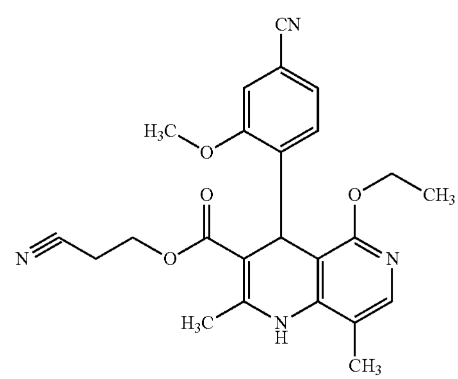

is converted using a chiral substituted tartaric ester of the formula (IIIa)

(IIIa)

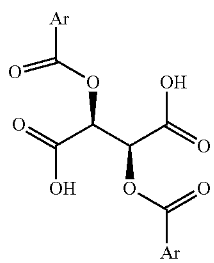

where Ar is unsubstituted or substituted aryl or heteroaryl to enantiomeric cyanoethanol ester 2-cyanoethyl (4S)-4-(4-cyano-2-methoxyphenyl)-5-ethoxy-2,8-dimethyl-1,4-dihydro-1,6-naphthyridine-3-carboxylate of the formula (IVa)

(IVa)

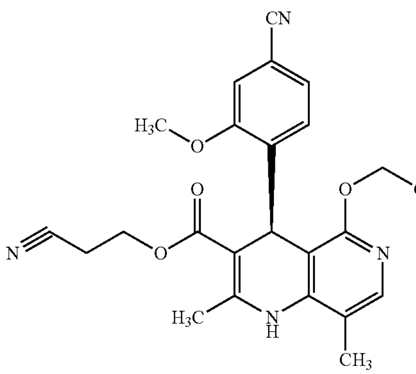

and the latter is hydrolysed in a THF/water mixture (2:1) with sodium hydroxide solution to give the compound of the formula (VIIa)

(VIIa)

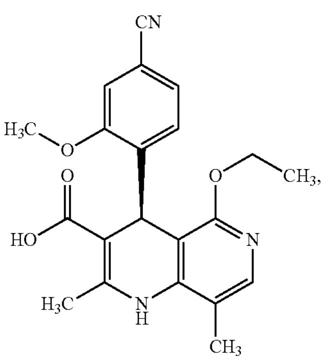

and the latter is then reacted in THE as solvent firstly with 1,1-carbodiimidazole and catalytic amounts of 4-(dimethylamino)pyridine, hexamethyldisilazane is added and then the mixture is heated under reflux for 16-24 hours, and then a THF/water mixture is added.

Preference is given to a process for preparing (4S)-4-(4-cyano-2-methoxyphenyl)-5-ethoxy-2,8-dimethyl-1,4-dihydro-1,6-naphthyridine-3-carboxamide of the formula (Ia)

(Ia)

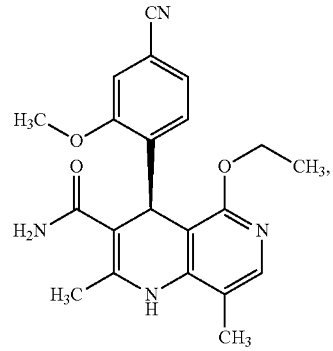

characterized in that racemic cyanoethanol ester of the formula (IV)

(IV)

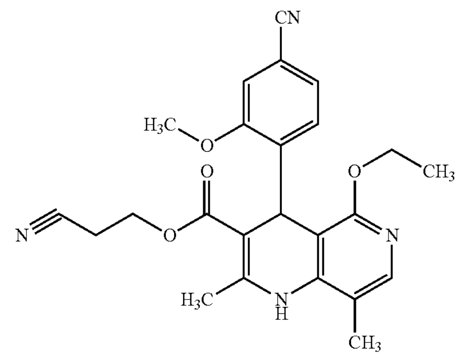

using a chiral substituted tartaric ester of the formula (IIIa)

(IIIa)

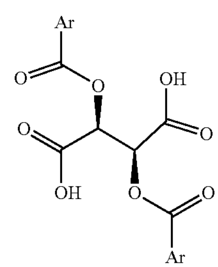

where Ar is

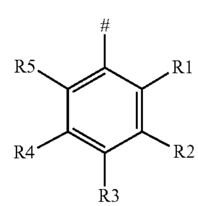

where #represents the site of attachment, where R1, R2, R3, R4, R5 are each a hydrogen atom or an alkyl radical, for example methyl, ethyl, propyl, or a halogen atom, for example fluorine, chlorine, bromine or iodine, or an ether group, for example O-methyl, O-ethyl, O-phenyl, or a nitro group, or a cyano group, or a CF3 group, or an amide group, for example —NHCOR in which R may be methyl, ethyl or phenyl, or —NRCOR in which R has the meaning given above or CONHR— in which R has the meaning given above or CONRR' group in which R' has the same meaning as R as defined above, or cyclic amides such as 3-oxomorpholin-4-yl, 2-oxopiperidin-1-yl, which may in turn be substituted. The substitution patterns may differ widely; for instance, up to 5 different substituents are theoretically possible, but preference is generally given to the monosubstituted Ar radicals. Ar may alternatively be a substituted heteroaromatic radical such as, preferably, pyridine or pyrazine. Ar may alternatively be a polycyclic aromatic hydrocarbon, for example a substituted naphthalene, anthracene or quinoline.

to enantiomeric cyanoethanol ester 2-cyanoethyl (4S)-4-(4-cyano-2-methoxyphenyl)-5-ethoxy-2,8-dimethyl-1,4-dihydro-1,6-naphthyridine-3-carboxylate of the formula (IVa)

(IVa)

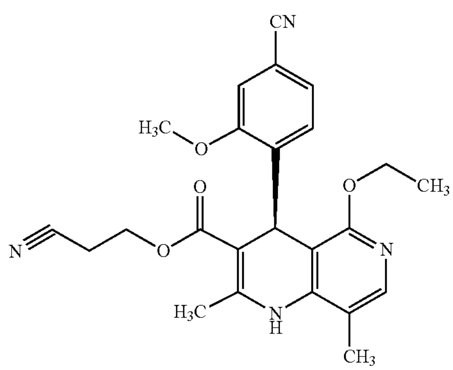

and the latter is hydrolysed in a THF/water mixture (2:1) with sodium hydroxide solution to give the compound of the formula (VIIa)

(VIIa)

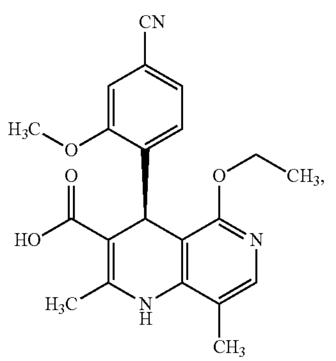

and the latter is then reacted in THF as solvent firstly with 1,1-carbodiimidazole and catalytic amounts of 4-(dimethylamino)pyridine, hexamethyldisilazane is added and then the mixture is heated under reflux for 16-24 hours, and then a THF/water mixture is added.

Preference is given to a process for preparing (4S)-4-(4-cyano-2-methoxyphenyl)-5-ethoxy-2,8-dimethyl-1,4-dihydro-1,6-naphthyridine-3-carboxamide of the formula (Ia)

where, in formula (III),

Ar is one of the formulae

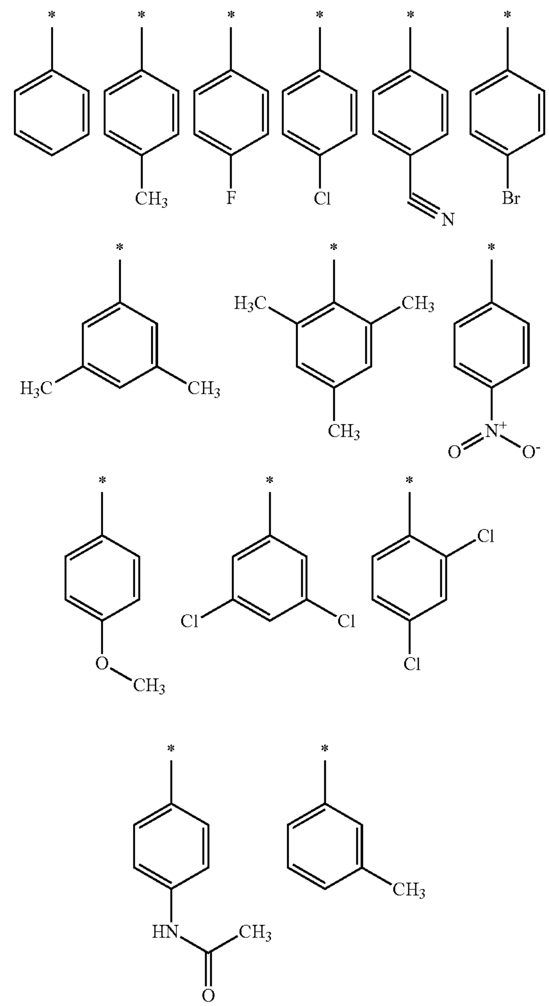

in which * represents the site of attachment.

Particular preference is given to a process for preparing (4S)-4-(4-cyano-2-methoxyphenyl)-5-ethoxy-2,8-dimethyl-1,4-dihydro-1,6-naphthyridine-3-carboxamide of the formula (Ia) where, in formula (III), Ar is one of the formulae

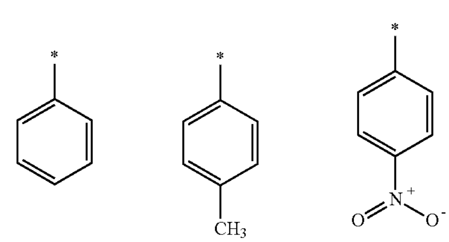

-continued

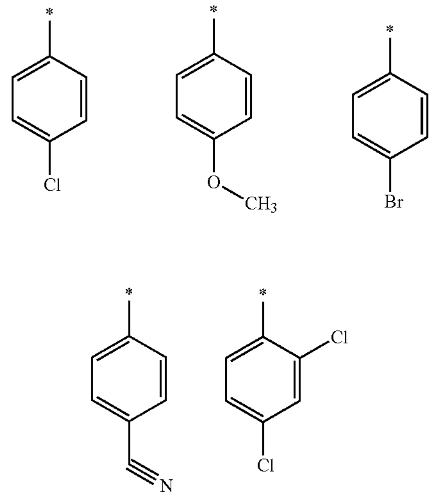

in which * represents the site of attachment.

Especial preference is given to a process for preparing (4S)-4-(4-cyano-2-methoxyphenyl)-5-ethoxy-2,8-dimethyl-1,4-dihydro-1,6-naphthyridine-3-carboxamide of the formula (Ia)

where, in formula (III),

Ar is one of the formulae

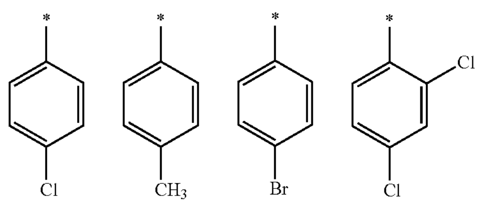

in which * represents the site of attachment.

Especial preference is given to a process for preparing (4S)-4-(4-cyano-2-methoxyphenyl)-5-ethoxy-2,8-dimethyl-1,4-dihydro-1,6-naphthyridine-3-carboxamide of the formula (Ia)

where, in formula (III),

Ar is one of the formulae

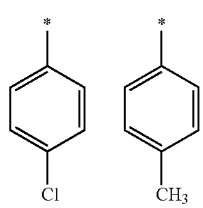

in which * represents the site of attachment.

Very particular preference is given to a process for preparing (4S)-4-(4-cyano-2-methoxyphenyl)-5-ethoxy-2,8-dimethyl-1,4-dihydro-1,6-naphthyridine-3-carboxamide of the formula (Ia)

(Ia)

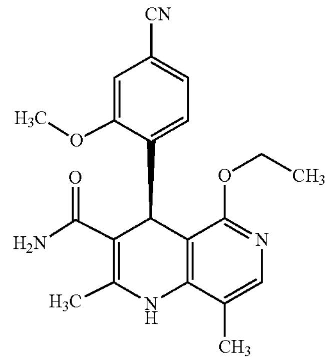

characterized in that racemic cyanoethanol ester of the formula (IV)

(IV)

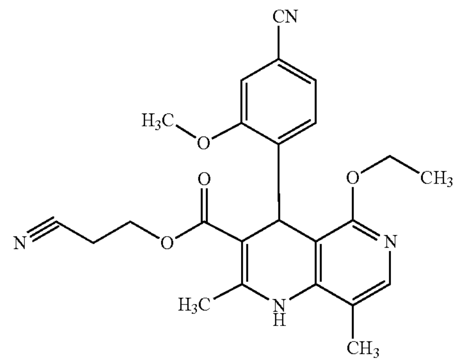

is converted using a chiral substituted tartaric ester of the formula (IIIa)

(IIIa)

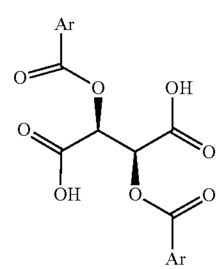

where

Ar is

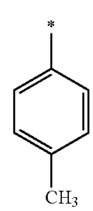 [SMILES: *c1ccc(C)cc1]

in which * represents the site of attachment to enantiomeric cyanoethanol ester 2-cyanoethyl (4S)-4-(4-cyano-2-methoxyphenyl)-5-ethoxy-2,8-dimethyl-1,4-dihydro-1,6-naphthyridine-3-carboxylate of the formula (IVa)

(IVa)

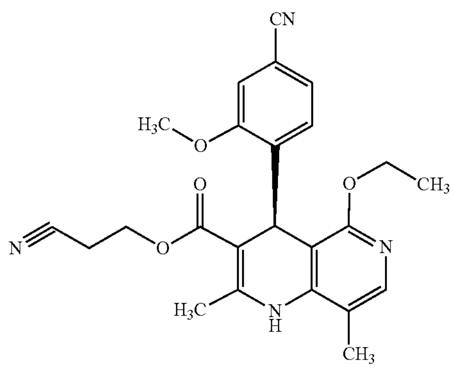

and the latter is hydrolysed in a THF/water mixture (2:1) with sodium hydroxide solution to give the compound of the formula (VIIa)

(VIIa)

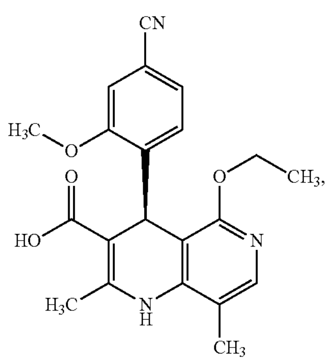

and the latter is then reacted in THF as solvent firstly with 1,1-carbodiimidazole and catalytic amounts of 4-(dimethylamino)pyridine, hexamethyldisilazane is added and then the mixture is heated under reflux for 16-24 hours, and then a THF/water mixture is added.

Paragraphs 1. to 14.

The following paragraphs 1. to 14. constitute further embodiments of the invention:

1. Process for preparing 2-cyanoethyl (4S)-4-(4-cyano-2-methoxyphenyl)-5-ethoxy-2,8-dimethyl-1,4-dihydro-1,6-naphthyridine-3-carboxylate of the formula (IVa)

(IVa)

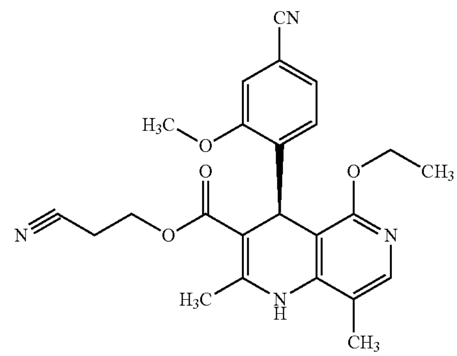

by optical resolution of racemic 2-cyanoethyl (4S)-4-(4-cyano-2-methoxyphenyl)-5-ethoxy-2,8-dimethyl-1,4-dihydro-1,6-naphthyridine-3-carboxylate of the formula (IV)

(IV)

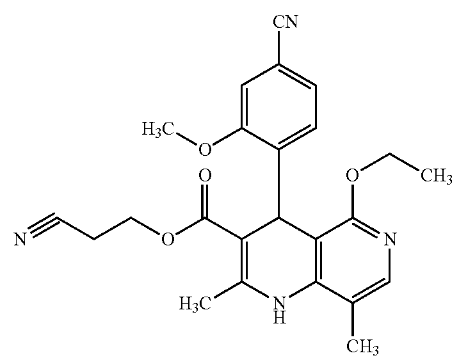

using a chiral substituted tartaric ester of the formula (IIIa)

(IIIa)

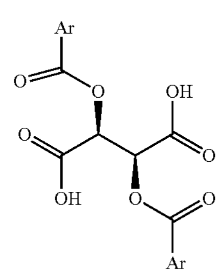

where Ar is unsubstituted or substituted aryl or heteroaryl.

2. Process according to paragraph 1, characterized in that the optical resolution is conducted in an ethanol/water mixture.

3. Process according to either of paragraphs 1 and 2, characterized in that the optical resolution is effected at a temperature in the range from 20° C. to 50° C.

4. Process according to any of paragraphs 1 to 3, characterized in that the optical resolution is effected at a temperature of 30° C. to 50° C.
5. Process according to any of paragraphs 1 to 4, characterized in that (+) di-p-tolyl-D-tartaric acid (IIIa')

(IIIa')

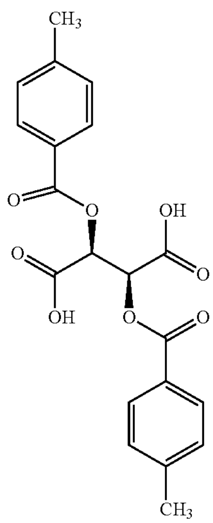

is used for optical resolution.
6. Process according to any of paragraphs 1 to 5, characterized in that the precipitated diastereomeric salt (Va), (Vb), (Vc) and/or (Vd) is isolated.
7. Process according to any of paragraphs 1 to 6, characterized in that the diastereomeric salt is treated with a base and the solvent is removed.
8. Process according to any of paragraphs 1 to 7, characterized in that the base used is potassium hydroxide, potassium phosphate or sodium phosphate.
9. Process according to any of paragraphs 1 to 8, wherein the racemate (IV)

(IV)

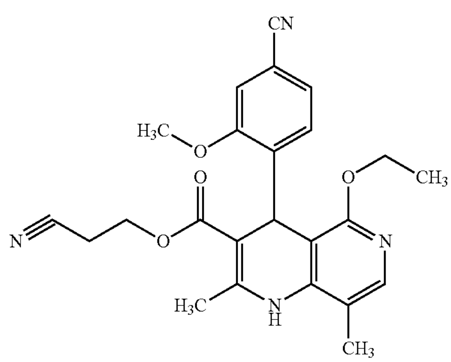

is reacted with di-p-tolyl-D-tartaric acid of the formula (IIIa')

(IIIa')

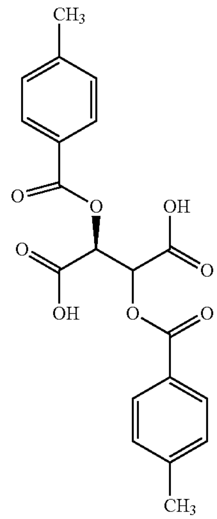

in a spirits/water mixture to give the diastereomeric salt (Va)

(Va)

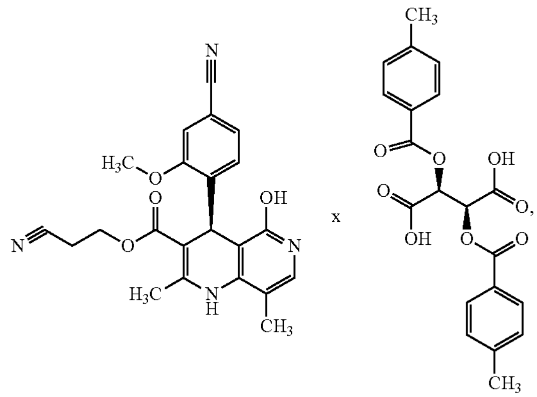

and then cyanoethanol ester (IVa)

(IVa)

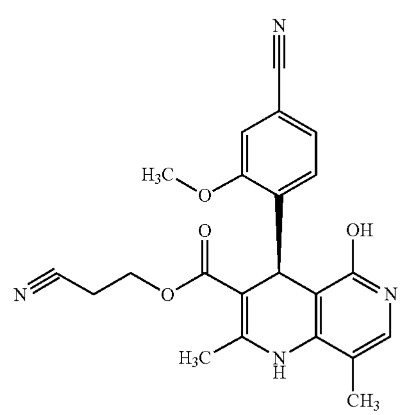

is released using sodium phosphate, likewise in a spirits/water mixture.

10. Process for preparing (4S)-4-(4-cyano-2-methoxyphenyl)-5-ethoxy-2,8-dimethyl-1,4-dihydro-1,6-naphthyridine-3-carboxamide of the formula (Ia)

(Ia)

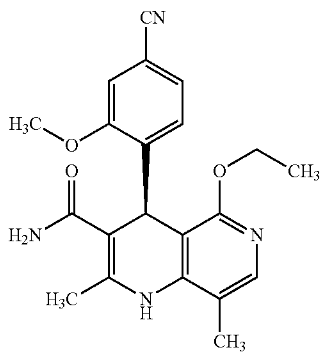

characterized in that of racemic 2-cyanoethyl (4S)-4-(4-cyano-2-methoxyphenyl)-5-ethoxy-2,8-dimethyl-1,4-dihydro-1,6-naphthyridine-3-carboxylate of the formula (IV)

(IV)

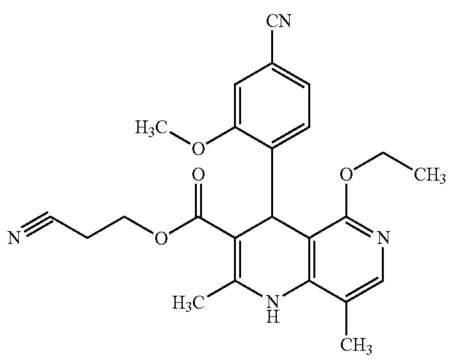

is converted using a chiral substituted tartaric ester of the formula (IIIa)

(IIIa)

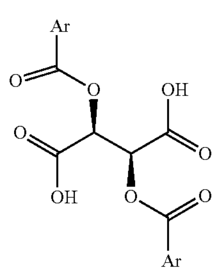

where Ar is unsubstituted or substituted aryl or heteroaryl to enantiomeric cyanoethanol ester 2-cyanoethyl (4S)-4-(4-cyano-2-methoxyphenyl)-5-ethoxy-2,8-dimethyl-1,4-dihydro-1,6-naphthyridine-3-carboxylate of the formula (IVa)

(IVa)

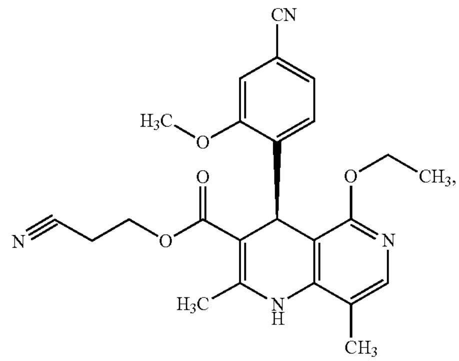

and the latter is hydrolysed in a THF/water mixture (2:1) with sodium hydroxide solution to give the compound of the formula (VIIa)

(VIIa)

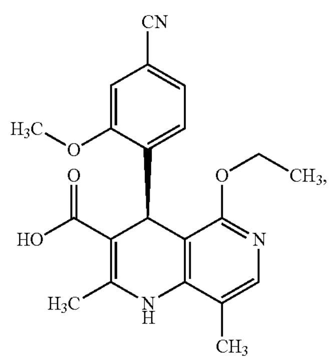

and the compound of the formula (VIIa) is then reacted in THE as solvent firstly with 1,1-carbodiimidazole and catalytic amounts of 4-(dimethylamino)pyridine, hexamethyldisilazane is added and then the mixture is heated under reflux for 16-24 hours, and then a THF/water mixture is added.

11. Process according to paragraph 10 for preparing (4S)-4-(4-cyano-2-methoxyphenyl)-5-ethoxy-2,8-dimethyl-1,4-dihydro-1,6-naphthyridine-3-carboxamide of the formula (Ia)

(Ia)

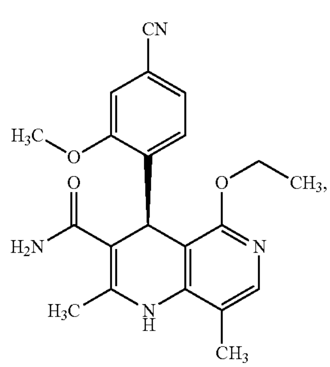

characterized in that racemic 2-cyanoethyl (4S)-4-(4-cyano-2-methoxyphenyl)-5-ethoxy-2,8-dimethyl-1,4-dihydro-1,6-naphthyridine-3-carboxylate of the formula (IV)

(IV)

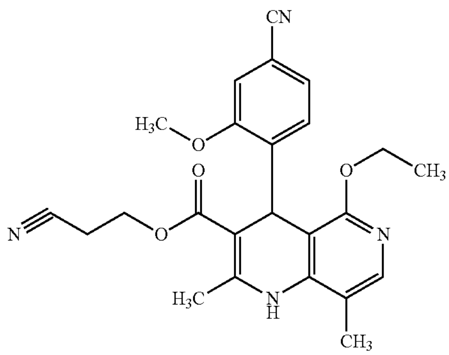

is converted using a chiral substituted tartaric ester of the formula (IIIa')

(IIIa')

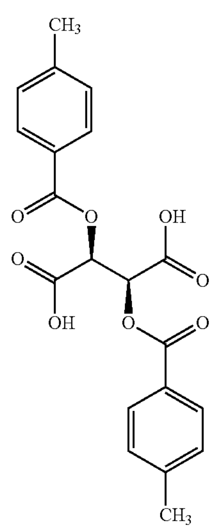

to enantiomeric cyanoethanol ester 2-cyanoethyl (4S)-4-(4-cyano-2-methoxyphenyl)-5-ethoxy-2,8-dimethyl-1,4-dihydro-1,6-naphthyridine-3-carboxylate of the formula (IVa)

(IVa)

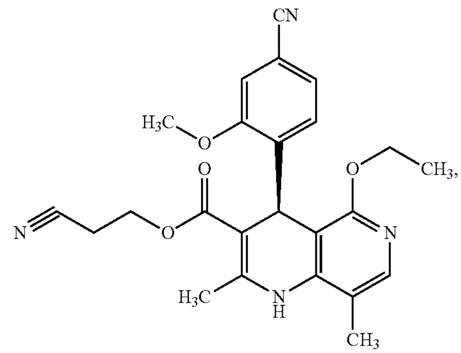

and the latter is hydrolysed in a THF/water mixture (2:1) with sodium hydroxide solution to give the compound of the formula (VIIa)

(VIIa)

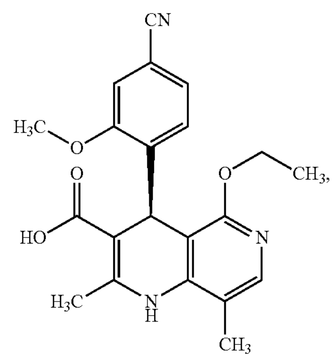

and the compound of the formula (VIIa) is then reacted in THE as solvent firstly with 1,1-carbodiimidazole and catalytic amounts of 4-(dimethylamino)pyridine, hexamethyldisilazane is added and then the mixture is heated under reflux for 16-24 hours, and then a THF/water mixture is added.

12. Diastereomeric salts of the formula (Va)

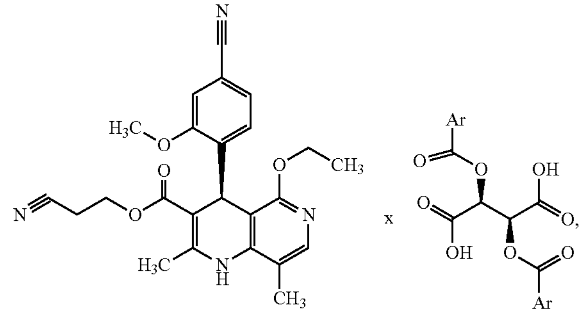

-continued (Vb)

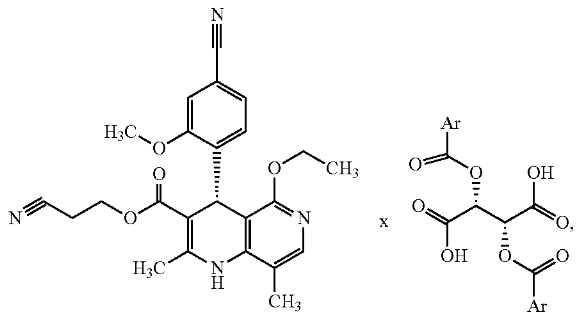

(Vc)

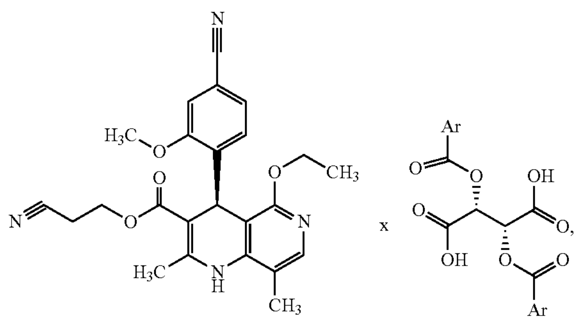

or (Vd)

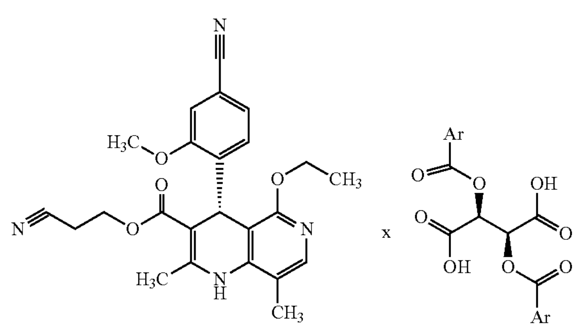

in which Ar is an unsubstituted or substituted aryl or heteroaryl and has the meaning given above.

13. Diastereomeric salt according to paragraph 12, characterized in that Ar is

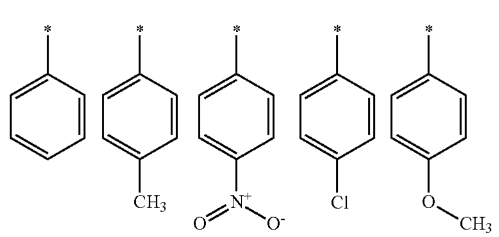

-continued

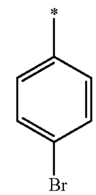

or

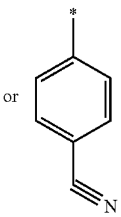

in which * represents the site of attachment.

14. Diastereomeric salt according to paragraph 12 or 13, characterized in that Ar is

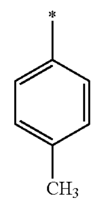

in which * represents the site of attachment.

Paragraphs (1) to (68)

Further embodiments of the invention are also described in the following paragraphs (1) to (68):

(1) Diastereomeric salt of the formula (Va)

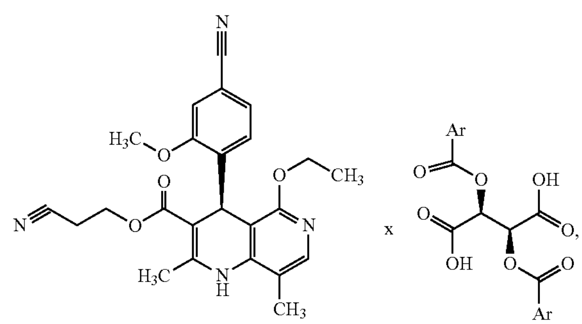

(Vb)

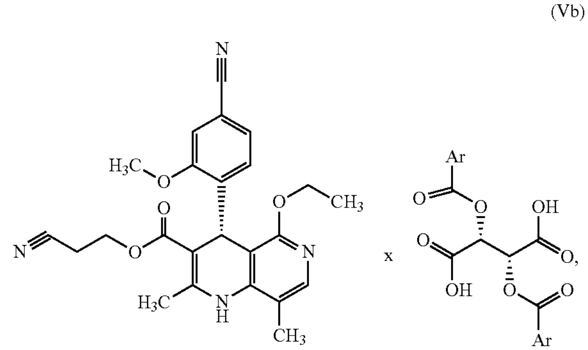

-continued (Vc)

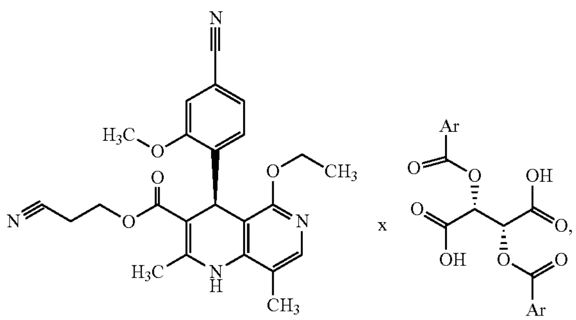

or (Vd)

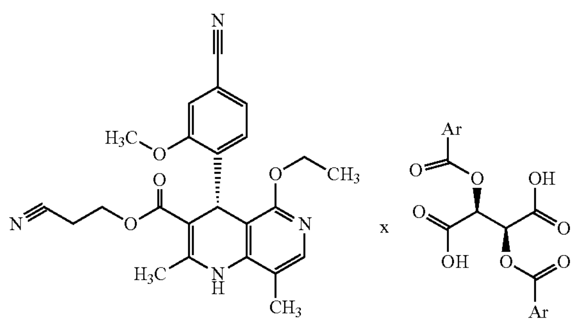

in which Ar is unsubstituted or substituted aryl or heteroaryl.

(2) Diastereomeric salt according to paragraph (1), wherein

Ar is a heteroaryl group selected from the group consisting of thienyl, furanyl, pyrrolyl, oxazolyl, thiazolyl, imidazolyl, pyrazolyl, isoxazolyl, isothiazolyl, oxadiazolyl, triazolyl, thiadiazolyl or tetrazolyl; or a six-membered heteroaryl group, for example pyridinyl, pyridazinyl, pyrimidinyl, pyrazinyl or triazinyl; or a tricyclic heteroaryl group, for example carbazolyl, acridinyl or phenazinyl; or a 9-membered heteroaryl group, for example benzofuranyl, benzothienyl, benzoxazolyl, benzisoxazolyl, benzimidazolyl, benzothiazolyl, benzotriazolyl, indazolyl, indolyl, isoindolyl, indolizinyl or purinyl; or a 10-membered heteroaryl group, for example quinolinyl, quinazolinyl, isoquinolinyl, cinnolinyl, phthalazinyl, quinoxalinyl and pteridinyl, or Ar is

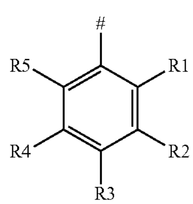

where #represents the site of attachment, where R1, R2, R3, R4, R5 are each a hydrogen atom or an alkyl radical, for example methyl, ethyl, propyl, or a halogen atom, for example fluorine, chlorine, bromine or iodine, or an ether group, for example O-methyl, O-ethyl, 0-phenyl, or a nitro group, or a cyano group, or a CF3 group, or an amide group, for example —NHCOR in which R may be methyl, ethyl or phenyl, or —NRCOR in which R has the meaning given above or CONHR— in which R has the meaning given above or CONRR' group in which R' has the same meaning as R as defined above, or cyclic amides such as 3-oxomorpholin-4-yl, 2-oxopiperidin-1-yl, which may in turn be substituted;

or

Ar is a substituted heteroaromatic radical such as, preferably, pyridine or pyrazine;

or

Ar is a polycyclic aromatic hydrocarbon, for example a substituted naphthalene, anthracene or quinoline.

(3) Diastereomeric salt according to paragraph (1) or (2), wherein

Ar is one of the formulae

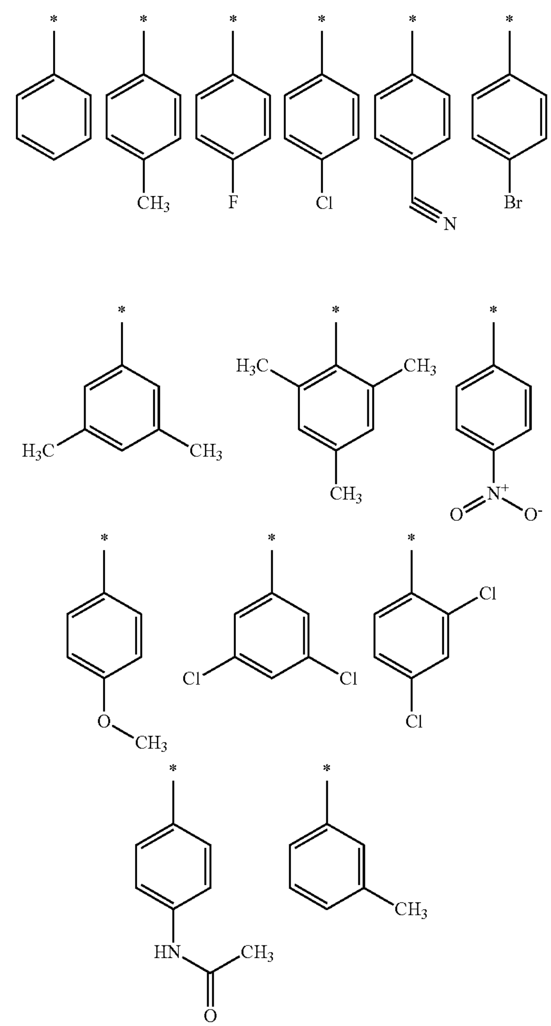

in which * represents the site of attachment.

(4) Diastereomeric salt according to any of paragraphs 1 to 3, wherein

Ar is one of the formulae

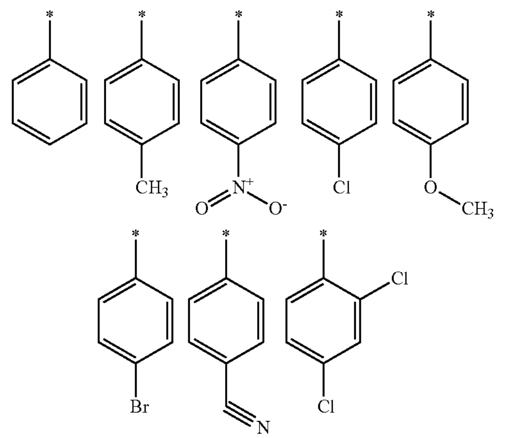

in which * represents the site of attachment.

(5) Diastereomeric salt according to any of paragraphs 1 to 4, wherein

Ar is one of the formulae

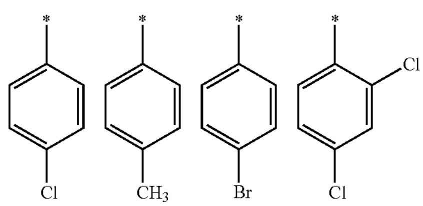

in which * represents the site of attachment.

(6) Diastereomeric salt according to any of paragraphs 1 to 5, wherein

Ar is one of the formulae

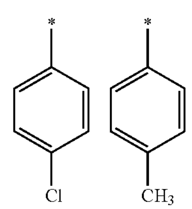

in which * represents the site of attachment.

(7) Diastereomeric salt according to any of paragraphs 1 to 6, wherein

Ar is

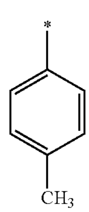 [SMILES: *c1ccc(C)cc1]

in which * represents the site of attachment.

(8) Process for preparing the diastereomeric salt (Va), (Vb), (Vc) and/or (Vd) according to any of paragraphs (1) to (7), comprising the step of (i) optical resolution of racemic 2-cyanoethyl (4S)-4-(4-cyano-2-methoxyphenyl)-5-ethoxy-2,8-dimethyl-1,4-dihydro-1,6-naphthyridine-3-carboxylate of the formula (IV)

(IV)

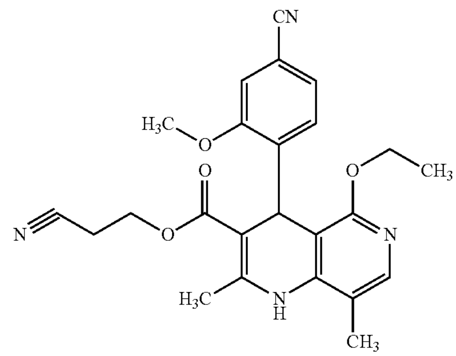

with a chiral substituted tartaric ester of the formula (IIIa) or (IIIb)

(IIIa)

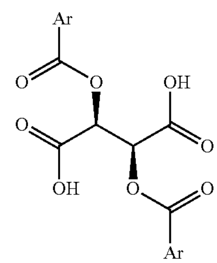

or (IIIb)

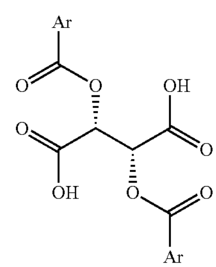

where Ar is unsubstituted or substituted aryl or heteroaryl.

(9) Process according to paragraph (8), wherein Ar is as defined in any of paragraphs (2), (3), (4), (5), (6) and (7).

(10) Process according to paragraph (8) or (9), wherein the optical resolution in step (i) is effected in an organic solvent or insolvent mixtures consisting of water and water-miscible organic solvents.

(11) Process according to one of paragraph (10), wherein the organic solvent is selected from ethanol, methanol, isopropanol, 1-propanol, ethyl acetate, isobutanol, dichloromethane, 1-pentanol, acetone and spirits.

(12) Process according to paragraph (10), wherein the solvent mixture is selected from ethyl acetate/methanol 90:10; methanol/water 80:20; ethanol/water 90:10; ethanol/water 85:15; ethanol/water 80:20; ethanol/water 75:25; ethanol/water 70:30; dichloromethane; 1-propanol/water 80:20; 1-pentanol; 1-pentanol/water 90:10; isopropanol; isopropanol/water 80:20; isobutanol/water 90:10; isobutanol/water 80:20; cyclohexanol/water 90:10; benzyl alcohol/water 90:10; ethylene glycol; and ethylene glycol/water 80:20, with the mixing ratios being reported in volume per volume (v/v).

(13) Process according to paragraph (10) or (12), wherein the solvent mixture is selected from ethanol/water, where the mixing ratio (v/v) is in the ethanol:water range of 1:1 to 6:1.

(14) Process according to any of paragraphs (10), (12) and (13), wherein the solvent mixture is selected from ethanol/water, where the mixing ratio (v/v) is in the ethanol:water range of 6:1 to 3:1.

(15) Process according to any of paragraphs (10), (12), (13) and (14), wherein the solvent mixture is selected from ethanol/water, where the mixing ratio (v/v) is in the ethanol:water range of 3:1.

(16) Process according to any of claims (8) to (15), wherein the solvent is used in a solvent mixture in a 10- to 60-fold excess, preferably 10- to 50-fold excess, where the excess (in litres) is based on the racemate (IV) (in kilograms).

(17) Process according to any of paragraphs (8) to (16), wherein the optical resolution in step (i) is conducted in an ethanol/water mixture.

(18) Process according to any of paragraphs (8) to (17), wherein the optical resolution in step (i) is conducted at a temperature in the range from 20° C. to 50° C.

(19) Process according to any of paragraphs (8) to (18), wherein the optical resolution in step (i) is effected at a temperature in the range from 30° C. to 50° C.

(20) Process according to any of paragraphs (8) to (19), wherein (+) di-p-tolyl-D-tartaric acid (IIIa')

(IIIa')

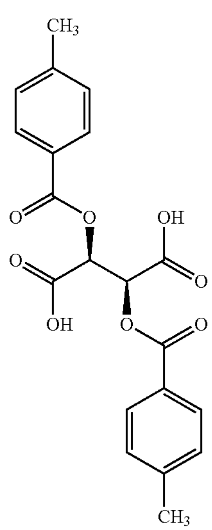

is used for optical resolution in step (i).

(21) Process according to any of paragraphs (8) to (20), further comprising step (ii):

(ii) isolating the precipitated diastereomeric salt (Va), (Vb), (Vc) and/or (Vd), where step (ii) follows step (i).

(22) Process according to any of paragraphs (8) to (21) for preparing the diastereomeric salt (Va) and/or (Vd), wherein, in step (i), the chiral substituted tartaric ester of the formula (IIIa)

(IIIa)

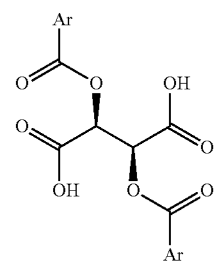

is used and wherein Ar is as defined in any of paragraphs (1), (2), (3), (4), (5), (6) and (7).

(23) Process according to any of paragraphs (8) to (21) for preparing the diastereomeric salt (Vb) and/or (Vc), wherein, in step (i), the chiral substituted tartaric ester of the formula (IIIb)

(IIIb)

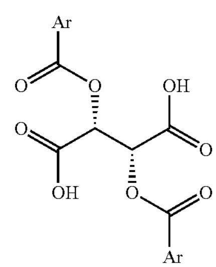

is used and wherein Ar is as defined in any of paragraphs (1), (2), (3), (4), (5), (6) and (7).

(24) Process according to any of paragraphs (8) to (23), wherein, in step (i), 0.5 to 2.0 equivalents of the tartaric ester (IIIa) or (IIIb) are used for the optical resolution.

(25) Process according to any of paragraphs (8) to (24), wherein, in step (i), 0.7 to 1.5 equivalents of the tartaric ester (IIIa) or (IIIb) are used for the optical resolution.

(26) Process according to any of paragraphs (8) to (25), wherein, in step (i), 0.7 to 1.4 equivalents of the tartaric ester (IIIa) or (IIIb) are used for the optical resolution.

(27) Process according to any of paragraphs (8) to (26), wherein, in step (i), 0.70 to 1.2 equivalents of the tartaric ester (IIIa) or (IIIb) are used for the optical resolution.

(28) Process for preparing 2-cyanoethyl (4S)-4-(4-cyano-2-methoxyphenyl)-5-ethoxy-2,8-dimethyl-1,4-dihydro-1,6-naphthyridine-3-carboxylate of the formula (IVa)

(IVa)

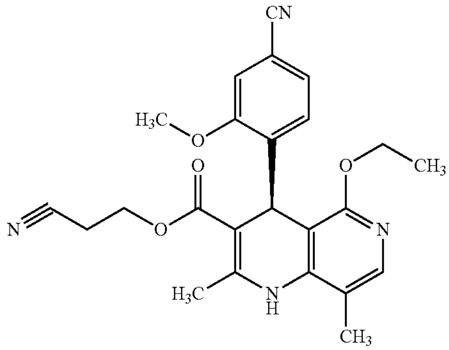

comprising steps (i) and (iii):

(i) optical resolution of racemic 2-cyanoethyl (4S)-4-(4-cyano-2-methoxyphenyl)-5-ethoxy-2,8-dimethyl-1,4-dihydro-1,6-naphthyridine-3-carboxylate of the formula (IV)

(IV)

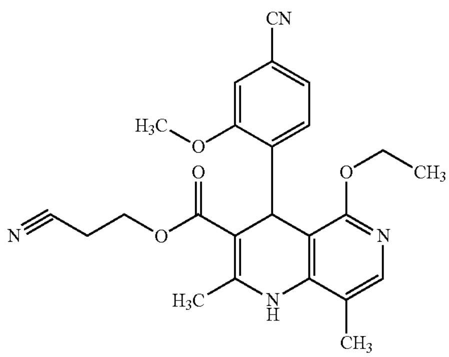

with a chiral substituted tartaric ester of the formula (IIIa) or (IIIb)

(IIIa)

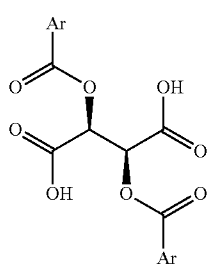

or (IIIb)

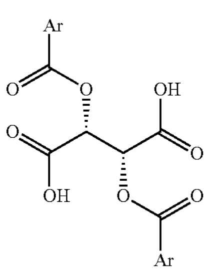

to obtain one or more of the diastereomeric salts (Va), (Vb), (Vc) and/or (Vd)

where Ar is unsubstituted or substituted aryl or heteroaryl, and (iii) converting the diastereomeric salt obtained in step (i) to the compound of formula (IVa).

(29) Process according to paragraph (28), wherein Ar is as defined according to any of paragraphs (2) to (7).

(30) Process according to paragraph (28) or (29), wherein step (i) is as defined according to any of paragraphs (8) to (27).

(31) Process according to any of paragraphs (28) to (30), further comprising step (ii):

(ii) isolating the precipitated diastereomeric salt (Va), (Vb), (Vc) and/or (Vd), wherein step (ii) optionally follows step (i) and precedes step (iii).

(32) Process according to any of paragraphs (28) to (30), wherein step (ii) is as defined according to any of paragraphs (21) to (27).

(33) Process according to any of paragraphs (28) to (32), comprising step (iii):

(iii) treating the diastereomeric salt (Va), (Vb), (Vc) and/or (Vd) obtained in step (i) with a base.

(34) Process according to any of paragraphs (28) to (33), wherein, in step (iii), the base is an organic or inorganic base.

(35) Process according to any of paragraphs (28) to (34), wherein, in step (iii), the base is an inorganic base and is selected from ammonia, sodium hydroxide solution, lithium hydroxide, potassium hydroxide, ammonium carbonate, sodium carbonate, potassium carbonate, lithium carbonate, ammonium hydrogencarbonate, sodium hydrogencarbonate, potassium hydrogencarbonate, sodium phosphate, potassium phosphate, ammonium phosphate, sodium hydroxide and mixtures thereof.

(36) Process according to any of paragraphs (28) to (34), wherein, in step (iii), the base is an organic base and is selected from aliphatic and aromatic bases.

(37) Process according to any of paragraphs (28) to (34) and (36), wherein, in step (iii), the base is an organic base and is selected from triethylamine, imidazole, N-methylimidazole, Hünig's base, pyridine, DBU and mixtures thereof.

(38) Process according to any of paragraphs (28) to (35), wherein, in step (iii), the base is selected from potassium hydroxide, potassium phosphate, sodium phosphate and mixtures thereof.

(39) Process according to any of paragraphs Process according to any of paragraphs (28) to (38), wherein a solvent is used in step (iii).

(40) Process according to any of paragraphs Process according to any of paragraphs (28) (39), wherein the solvent is selected from water, water-miscible organic solvents, ethanol, isopropanol, ethane-1,2-diol, methoxyethanol, methanol, acetone, spirit and mixtures thereof.

(41) Process according to any of paragraphs Process according to any of paragraphs (28) to (40), wherein the solvent is selected from mixtures of water and ethanol, where the mixing ratio (v/v) is in the ethanol:water range of 1:6 to 1:3.

(42) Process according to any of paragraphs Process according to any of paragraphs (28) to (41), wherein the solvent is selected from mixtures of water and ethanol, where the mixing ratio (v/v) is in the ethanol:water range of 1:3, where the volume is based on the total volume of the solvent.

(43) Process according to any of paragraphs (28) to (42), wherein the amount of solvent mixture used in step (iii) is 7 to 20 times the amount of the diastereomeric salt (IVa) or (IVb) or (IVc) or (IVd) used.

(44) Process according to any of paragraphs (28) to (43), wherein the amount of solvent mixture used in step (iii) is 9 to 11 times the amount of the diastereomeric salt (IVa) or (IVb) or (IVc) or (IVd) used.

(45) Process according to any of paragraphs (28) to (44), wherein the amount of solvent mixture used in step (iii) is 10 times the amount of the diastereomeric salt (IVa) or (IVb) or (IVc) or (IVd) used.

(46) Process according to any of paragraphs (28) to (45), wherein the solvent or solvent mixture in step (ii) is initially charged at a temperature of 0° C. to 60° C., preferably 0° C. to 50° C., then adjusted to a pH of 6.9 to 8.0, preferably a pH of 7.0 to 7.5, more preferably pH 7.1, by adding the organic or inorganic base.

(47) Process according to any of paragraphs (28) to (46), further comprising step (iv):

(iv) removing the solvent, wherein step (iv) optionally follows step (iii).

(48) Process according to any of paragraphs (28) to (47), wherein the racemate (IV)

(IV)

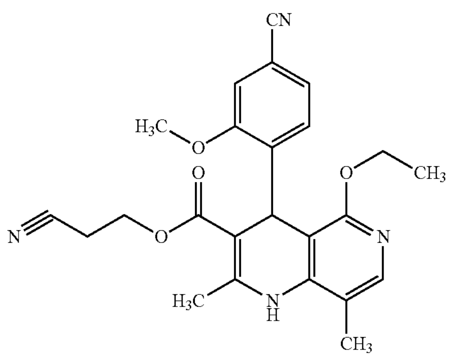

in step (i) is reacted with di-p-tolyl-D-tartaric acid of the formula (IIIa')

(IIIa')

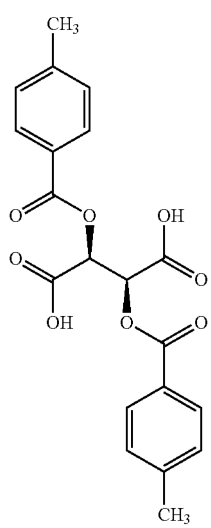

in a spirits/water mixture to give the diastereomeric salt (Va)

(Va)

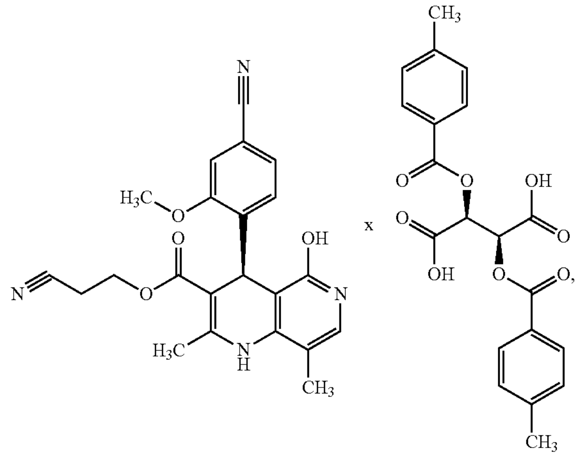

and then, in step (iii), cyanoethanol ester (IVa)

(IVa)

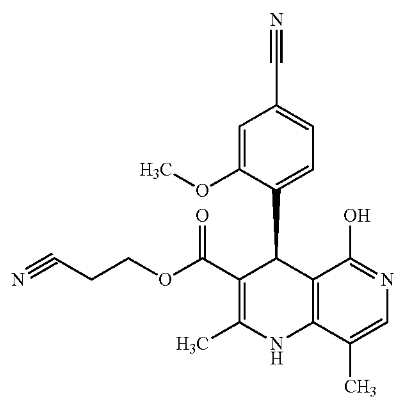

is released using sodium phosphate, likewise in a spirits/water mixture.

(49) Process for preparing (4S)-4-(4-cyano-2-methoxyphenyl)-5-ethoxy-2,8-dimethyl-1,4-dihydro-1,6-naphthyridine-3-carboxamide of the formula (Ia), comprising the steps (i), (iii), (v) and (vi)

(i) optical resolution of racemic 2-cyanoethyl (4S)-4-(4-cyano-2-methoxyphenyl)-5-ethoxy-2,8-dimethyl-1,4-dihydro-1,6-naphthyridine-3-carboxylate of the formula (IV)

(IV)

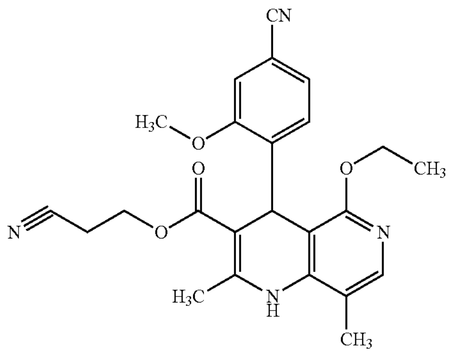

with a chiral substituted tartaric ester of the formula (IIIa) or (IIIb)

(IIIa)

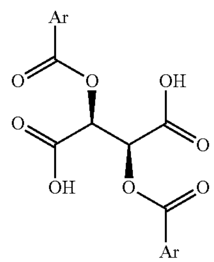

or (IIIb)

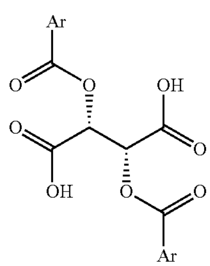

to obtain one or more of the diastereomeric salts (Va), (Vb), (Vc) and/or (Vd) where Ar is unsubstituted or substituted aryl or heteroaryl, (iii) converting the diastereomeric salt obtained in step (i) to the compound of formula (IVa).

(IVa)

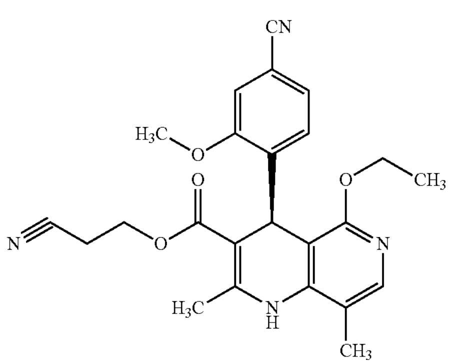

(v) hydrolysing the compound of formula (IVa) with sodium hydroxide solution in a THF/water mixture (2:1) to give the compound of the formula (VIIa)

(VIIa)

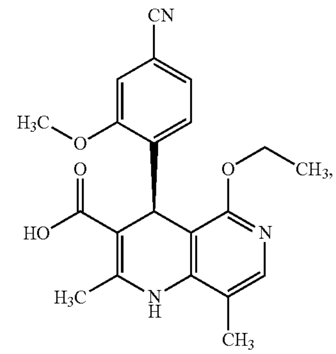

(vi) reacting the compound of the formula (VIIa), in THE as solvent, firstly with 1,1-carbodiimidazole and catalytic amounts of 4-(dimethylamino)pyridine, adding hexamethyldisilazane and then heating the mixture under reflux for 16-24 hours, and then adding a THF/water mixture, so as to obtain the compound of formula (Ia).

(50) Process according to paragraph (49), wherein Ar is as defined according to any one of paragraphs (2) to (7).

(51) Process according to paragraph (49) or (50), wherein step (i) is as defined according to any of paragraphs (8) to (48).

(52) Process according to any of paragraphs (49) to (51), wherein step (iii) is as defined according to any of paragraphs (28) to (48).

(53) Process according to any of paragraphs (49) to (52), wherein the process further comprises step (ii) according to any of the preceding paragraphs (8) to (48).

(54) Process according to any of paragraphs (49) to (53), wherein the process further comprises step (iv) according to any of the preceding paragraphs (8) to (48).

(55) Use of one or more diastereomeric salts (Va), (Vb), (Vc) and/or (Vd) in a process for preparing the compound of formula (IVa) or (IVb).

(56) Use of one or more diastereomeric salts (Va), (Vb), (Vc) and/or (Vd) in a process for preparing the compound of formula (IVa) or (IVb) according to any of the preceding paragraphs (8) to (54).

(57) Use of one or more diastereomeric salts (Va), (Vb), (Vc) and/or (Vd) in a process for preparing the compound of formula (VIIa).

(58) Use of one or more diastereomeric salts (Va), (Vb), (Vc) and/or (Vd) in a process for preparing the compound of formula (VIIa) according to any of the preceding paragraphs (8) to (54).

(59) Use of one or more diastereomeric salts (Va), (Vb), (Vc) and/or (Vd) in a process for preparing the compound of formula (Ia).

(60) Use of one or more diastereomeric salts (Va), (Vb), (Vc) and/or (Vd) in a process for preparing the compound of formula (Ia) according to any of the preceding paragraphs (8) to (54).

(61) Use of a chiral substituted tartaric ester of the formula (IIIa) or (IIIb) for preparation of one of the diastereomeric salts (Va), (Vb), (Vc) and/or (Vd) according to any of paragraphs (1) to (7).

(62) Use of a chiral substituted tartaric ester of the formula (IIIa') for preparation of one of the diastereomeric salts (Va), (Vb), (Vc) and/or (Vd) according to any of paragraphs (1) to (7).

(63) Use of a chiral substituted tartaric ester of the formula (IIIa) or (IIIb) for preparation of one of the compounds of formula (IVa).

(64) Use of a chiral substituted tartaric ester of the formula (IIIa') for preparation of one of the compounds of formula (IVa).

(65) Use of a chiral substituted tartaric ester of the formula (IIIa) or (IIIb) for preparation of one of the compounds of formula (VIIa).

(66) Use of a chiral substituted tartaric ester of the formula (IIIa') for preparation of one of the compounds of formula (VIIa).

(67) Use of a chiral substituted tartaric ester of the formula (IIIa) or (IIIb) for preparation of one of the compounds of formula (Ia).

(68) Use of a chiral substituted tartaric ester of the formula (IIIa') for preparation of one of the compounds of formula (Ia).

EXPERIMENTAL

| Abbreviations and acronyms | |
|---|---|
| EtOH | ethanol |
| DMSO | dimethyl sulfoxide |
| of th. | of theory (in yield) |
| HPLC | high-pressure, high-performance liquid chromatography |
| 1H-NMR | 1H nuclear magnetic resonance spectrometry |
| IT | internal temperature |
| MS | mass spectrometry |
| RT | room temperature |
| RRT | relative retention time |
| TFA | trifluoroacetic acid |
| TI | internal temperature |
| TM | jacket temperature |
| XRPD | X-ray powder diffraction (powder diffractometer) |
| Spirits | ethanol denatured with 2% toluene |
| h | hour |
| vol | volume |

Examples

Table 3 below shows the structures of the compounds recovered in HPLC. The assignment of the retention times in HPLC is shown below.

TABLE 3

(I)

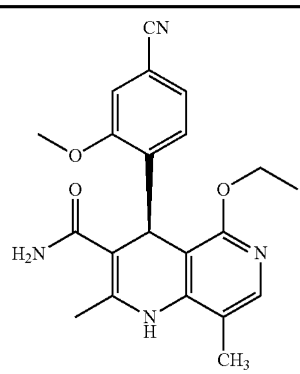

Finerenone

TABLE 3-continued impurity A

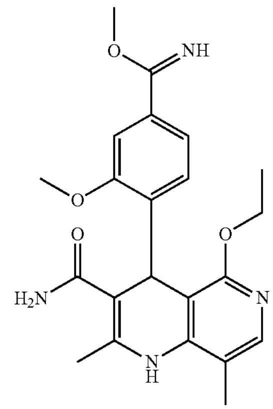 [SMILES: CCOc1ncc(C)c2c1C(c1ccc(C(=N)OC)cc1OC)C(C(N)=O)=C(C)N2]

impurity B

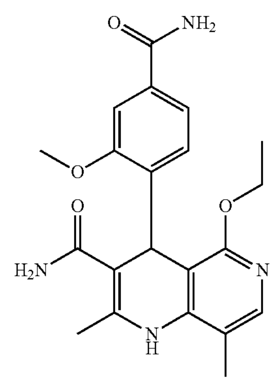 [SMILES: CCOc1ncc(C)c2c1C(c1ccc(C(N)=O)cc1OC)C(C(N)=O)=C(C)N2]

(unknown structure, always significantly less than 0.1%)

impurity C impurity D

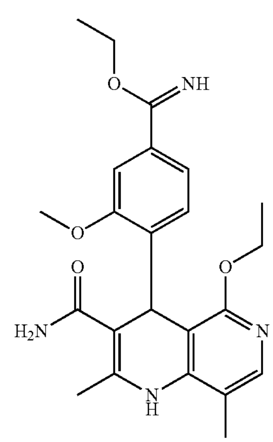 [SMILES: CCOC(=N)c1ccc(C2C(C(N)=O)=C(C)Nc3c(C)cnc(OCC)c32)c(OC)c1]

TABLE 3-continued impurity E

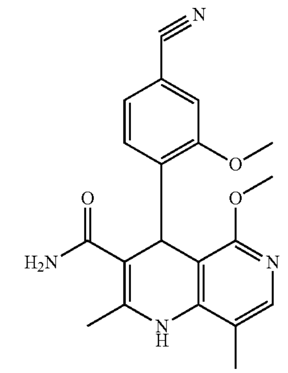 [SMILES: COc1cc(C#N)ccc1C1C(C(N)=O)=C(C)Nc2c(C)cnc(OC)c21]

impurity G

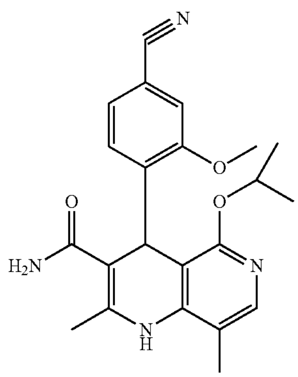 [SMILES: COc1cc(C#N)ccc1C1C(C(N)=O)=C(C)Nc2c(C)cnc(OC(C)C)c21]

impurity F

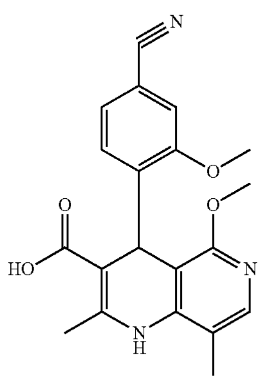 [SMILES: COc1cc(C#N)ccc1C1C(C(=O)O)=C(C)Nc2c(C)cnc(OC)c21]

impurity I

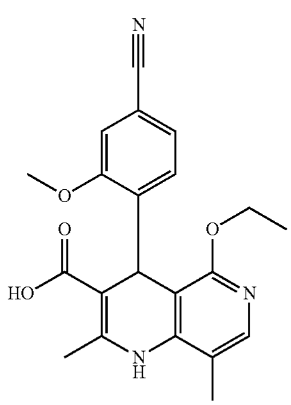 [SMILES: CCOc1ncc(C)c2c1C(c1ccc(C#N)cc1OC)C(C(=O)O)=C(C)N2]

TABLE 3-continued impurity J

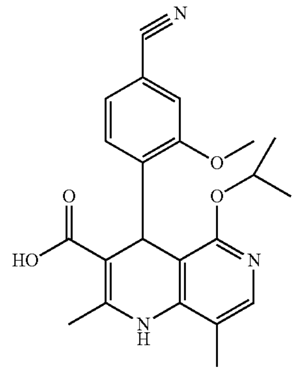 [SMILES: COc1cc(C#N)ccc1C1C(C(=O)O)=C(C)Nc2c(C)cnc(OC(C)C)c21]

impurity K

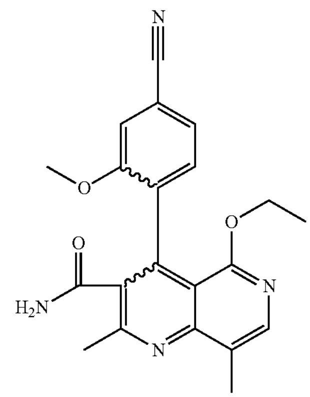 [SMILES: CCOc1ncc(C)c2nc(C)c(C(N)=O)c(-c3ccc(C#N)cc3OC)c12]

Analytical method for checking the content of impurities and the enantiomeric purity at the stage of crude finerenone (I)

Content and Organic Impurities

| | RT (min) | RRT |
|---|---|---|
| Finerenone (I) | 6.2 | 1.00 |
| impurity A | 3.3 | 0.53 |
| impurity B | 3.7 | 0.60 |
| impurity C | 3.9 | 0.62 |
| impurity D | 4.4 | 0.70 |
| impurity E | 5.5 | 0.89 |
| impurity F | 5.6 | 0.91 |
| impurity G | 6.8 | 1.10 |
| impurity H | 7.6 | 1.23 |
| impurity K | 10.4 | 1.68 |

Instrument: ultrahigh-performance liquid chromatograph (having a pressure range of up to 1200 bar with temperature-controlled column oven and UV detector)

Column:

| | | |
|---|---|---|
| YMC | Triart | C8 |

length: 100 mm; internal diameter: 3.0 mm; particle size: 1.9 μm

Max pressure: 1000 bar

Conditions: 20° C.; 0.50 ml/min; 1.7 μl (10° C.); 252 nm/6 nm and 230 nm/6 nm for the evaluation of DB-tartaric acid Eluent: A: 0.1% TFA in water; B: acetonitrile Gradient:

| time (min) | A (%) | B (%) |
|---|---|---|
| 0.0 | 90.0 | 10.0 |
| 15.0 | 35.0 | 65.0 |
| 16.0 | 20.0 | 80.0 |
| 20.0 | 20.0 | 80.0 |

Enantiomeric Purity:
Method A

| | RT (min) | RRT |
|---|---|---|
| Finerenone (I) | about 11 | 1.00 |
| (Ia) | about 9 | 0.82 |

Instrument: high-performance liquid chromatograph with temperature-controlled column oven and UV detector
Column: Chiralpak IA
length: 250 mm, internal diameter: 4.6 mm, particle size: 5.0 μm
Max pressure: 300 bar
Conditions: 40° C.; 0.8 ml/min; 5 μl (20° C.); 255 nm/6 nm
Eluent: A: acetonitrile; B: methyl tert-butyl ether (MTBE)
Isocratic: A (%) 90: B (%) 10

Enantiomeric Purity
Method B

| | RT(min) | RRT |
|---|---|---|
| Finerenone (I) | 5.7 | 1.00 |
| Enantiomer (Ia) | 6.8 | 1.19 |

Instrument/detector: high-performance liquid chromatograph with temperature-controlled column oven, UV detector
and data evaluation system
Measurement wavelength: 252 nm
Oven temperature: 40° C.
Column: Chiralpak IC
length: 150 mm, internal diameter: 4.6 mm, particle size: 3 μm Mobile Phase:
A: 50% buffer 20 mM $NH_4OAc$ pH 9
B: 50% acetonitrile
Flow rate: 1 ml/min.
Elution time: 8 min.
Equilibration: unnecessary, isocratic
Sample solvent: eluent
Sample solution: about 0.5 mg/ml of the substance racemate, dissolved in sample solvent Comparative solution: A comparative solution analogous to the sample solution is prepared
Injection volume: 10 μl The measured values stated in the examples below for enantiomer determination were all determined by Method B. Some values, especially those of the batches prepared in the pilot plant, were reanalysed with Method A for comparison, and gave comparable results.

The HPLC analysis data given in the examples which follow with respect to purity and content of the end product pure finerenone (I) refer only to impurities present in the product in an amount of >0.05%. This is essentially impurity E. All other impurities shown in the table listed above are generally <0.05%. The structure of such impurities was determined by isolation from enriched mother liquors.

HPLC Conditions/Methods
Method (C)
YMC Hydrosphere C18
150*4.6 mm, 3.0 μm
25° C., 1 ml/min, 270 nm, 4 nm
0 min: 70% TFA 0.1%*; 30% acetonitrile
17 min: 20% TFA 0.1%; 80% acetonitrile
18 min: 70% TFA 0.1%; 30% acetonitrile
*: TFA in water Method (D)
YMC Hydrosphere C18
150*4.6 mm, 3.0 μm
25° C., 1 ml/min, 255 nm, 6 nm
0 min: 90% TFA 0.1%; 10% acetonitrile
20 min: 10% TFA 0.1%; 90% acetonitrile
18 min: 10% TFA 0.1%; 90% acetonitrile Method (E)
Nucleodur Gravity C18
150*2 mm, 3.0 μm
35° C., 0.22 ml/min, 255 nm, 6 nm
Solution A: 0.58 g of ammonium hydrogenphosphate and 0.66 g of ammonium dihydrogenphosphate in 1 l of water (ammonium phosphate buffer pH 7.2)
Solution B: acetonitrile
0 min: 30% B; 70% A
15 min: 80% B; 20% A
25 min: 80% B; 20% A Method (F)
Implementation Instructions

| Enantiomeric purity | RT(min) | RRT |
|---|---|---|
| Enantiomer IVa | 3.8 | 1.00 |
| Enantiomer IVb | 4.8 | 1.26 |

Instrument/detector: high-performance liquid chromatograph with temperature-controlled column oven, UV detector
and data evaluation system
Measurement wavelength: 253 nm, range: 6 nm
Oven temperature: 40° C.
Column: Chiralpak AD-H
length: 250 mm, internal diameter: 4.6 mm, particle size: 5 μm
Mobile phase: A: heptane
B: isopropanol+0.1% DEA (diethylamine)
Gradient programme: Time [min]
Flow rate:

| | Eluent A [%] | Eluent B [%] |
|---|---|---|
| Start 2 [ml/min] | 80 | 20 |

Elution time: 8 min.

Example 1a

Preparation of the diastereomeric salt (Va) of 2-cyanoethyl (4S)-4-(4-cyano-2-methoxyphenyl)-5-ethoxy-2,8-dimethyl-1,4-dihydro-1,6-naphthyridine-3-carboxylate with (+) Di-p-tolyl-D-tartaric acid 4 g (9.249 mmol) of racemic 2-cyanoethyl (4S, 4R)-4-(4-cyano-2-methoxyphenyl)-5-ethoxy-2,8-dimethyl-1,4-dihydro-1,6-naphthyridine-3-carboxylate (IV) and 3.573 g (9.249 mmol) of (+)-di-p-tolyl-D-tartaric acid were suspended in a mixture of 150 ml of ethanol and 50 ml of water and heated to 30° C. (forming a solution). The mixture was stirred at room temperature overnight, and the precipitate crystals were filtered off and washed twice with 5 ml of a mixture of ethanol/water 3:1. The product was dried under reduced pressure at room temperature.

Yield: 4.0 g (105.6% of theory) of a colourless crystalline powder.

Analytical Results:

Enantiomeric purity (e.e %): 65% e.e. (Method F)

An amount of the diastereomeric salt enriched in this way was purified further as follows:

3.80 g of the diastereomeric salt prepared was suspended in 76 ml of a mixture of ethanol/water 3:1, and the mixture was stirred at 50° C. for 2 h and at room temperature overnight. The precipitated crystals were filtered off and washed twice with 5 ml of a mixture of ethanol/water 3:1. The product is dried under reduced pressure at room temperature.

Yield: 3.0 g (79.3% of theory) of a colourless crystalline powder

Analytical Results:

Enantiomeric purity (e.e. %): 97% e.e. (Method F)

MS (EIpos): m/z=433 $[M+H]^+$ $^1$H-NMR (400 MHz, DMSO-$d_6$): δ=1.11 (t, J=7.03 Hz, 1H), 2.03-2.45 (m, 5H), 2.63-2.90 (m, 1H), 3.77 (s, 1H), 3.96-4.24 (m, 1H), 5.18-5.44 (m, 1H), 5.63-6.07 (m, 1H), 7.09-7.52 (m, 2H), 7.53-7.74 (m, 1H), 7.81-8.13 (m, 1H), 8.26-8.57 (m, 1H), 12.82-15.60 (m, 1H).

Example 1b

Preparation of 2-cyanoethyl (4S)-4-(4-cyano-2-methoxyphenyl)-5-ethoxy-2,8-dimethyl-1,4-dihydro-1,6-naphthyridine-3-carboxylate (IVa)

To 3 g (3.66 mmol) of the title compound from Example 1a was suspended in 30 ml of a mixture of water/ethanol 3:1, and the mixture was cooled to 0° C. Then a 20% aqueous sodium phosphate solution was metered in gradually (over the course of 1 hour) and the pH was adjusted to pH 7.1. The mixture was left to stir at that temperature for a further 4 hours. The precipitated solids were filtered off and washed twice with 10 ml of a mixture (0° C.) of water/ethanol 3:1. The product was dried under reduced pressure at 40° C.

Yield: 1.51 g (95.4% of theory) of a colourless crystalline powder

Analytical Results:

Enantiomeric purity (e.e. %): 97% e.e.

MS (EIpos): m/z=433 $[M+H]^+$ $^1$H-NMR (300 MHz, DMSO-$d_6$): δ=1.11 (t, 3H), 2.16 (s, 3H), 2.42 (s, 3H), 2.78 (m, 2H), 3.77 (s, 3H), 4.01-4.13 (m, 4H), 5.37 (s, 1H), 7.25 (d, 1H), 7.28-7.33 (m, 2H), 7.60 (s, 1H), 8.35 (s, 1H).

Example 2a

Preparation of the diastereomeric salt (Va) of 2-cyanoethyl (4S)-4-(4-cyano-2-methoxyphenyl)-5-ethoxy-2,8-dimethyl-1,4-dihydro-1,6-naphthyridine-3-carboxylate with (+) Di-p-tolyl-D-tartaric acid 900.0 g (2.08 mol) of racemic 2-cyanoethyl (4S, 4R)-4-(4-cyano-2-methoxyphenyl)-5-ethoxy-2,8-dimethyl-1,4-dihydro-1,6-naphthyridine-3-carboxylate (IV) and 803.6 g (2.08 mmol) of (+)-di-p-tolyl-D-tartaric acid were suspended in a mixture of 15 l of a mixture of ethanol/water 3:1 and heated to 30° C. (forming a solution). The mixture was stirred at room temperature overnight, and the precipitated crystals were filtered off and washed twice with 1000 ml of a mixture of ethanol/water 3:1. The product was dried under reduced pressure at room temperature.

Yield: 873.5 g (102.6% of theory) of a colourless crystalline powder.

Analytical Results:

Enantiomeric purity (e.e. %): 73% e.e. (Method F)

An amount of the diastereomeric salt enriched in this way was purified further as follows:

870 g of the diastereomeric salt prepared was suspended in 10 l of a mixture of ethanol/water 3:1, and the mixture was stirred at 50° C. for 2 h and at room temperature overnight. The precipitated crystals were filtered off and washed twice with 1000 ml of a mixture of ethanol/water 3:1. The product was dried under reduced pressure at 40° C.

Yield: 679.4 g (78.6% of theory) of a colourless crystalline powder

Analytical Results:

Enantiomeric purity (e.e. %): 98% e.e. (Method F)

Example 2b

Preparation of 2-cyanoethyl (4S)-4-(4-cyano-2-methoxyphenyl)-5-ethoxy-2,8-dimethyl-1,4-dihydro-1,6-naphthyridine-3-carboxylate (IVa)

To 600 g (732.7 mmol) of the title compound from Example 2a was suspended in 6 l of a mixture of water/ethanol 3:1, and the mixture was cooled to 0° C. Then a 30% aqueous sodium phosphate solution was metered in gradually (over the course of 1 hour) and the pH was adjusted to pH 7.1. The mixture was left to stir at that temperature for a further 4 hours. The precipitated solids were filtered off and washed twice with 1000 ml of a mixture (0° C.) of water/ethanol 3:1. The product was dried under reduced pressure at 40° C.

Yield: 301.0 g (95.1% of theory) of a colourless crystalline powder

Analytical Results:

Enantiomeric purity (e.e. %): 98% e.e.

MS (EIpos): m/z=433 $[M+H]^+$ $^1$H-NMR (300 MHz, DMSO-$d_6$): δ=1.11 (t, 3H), 2.16 (s, 3H), 2.42 (s, 3H), 2.78 (m, 2H), 3.77 (s, 3H), 4.01-4.13 (m, 4H), 5.37 (s, 1H), 7.25 (d, 1H), 7.28-7.33 (m, 2H), 7.60 (s, 1H), 8.35 (s, 1H).

Example 2c

(4S)-4-(4-Cyano-2-methoxyphenyl)-5-ethoxy-2,8-dimethyl-1,4-dihydro-1,6-naphthyridine-3-carboxylic acid (VIIa)

200 g (4.624 mol) of 2-cyanoethyl 4-(4-cyano-2-methoxyphenyl)-5-ethoxy-2,8-dimethyl-1,4-dihydro-1,6-naphthyridine-3-carboxylate (IVa) was dissolved in a mixture of 1.2 l of THF and 600 ml of water and cooled to 0° C. To this solution was added dropwise, at 0° C. over the course of 15 minutes, a sodium hydroxide solution (prepared from 82 g of 45% aqueous sodium hydroxide (924.8 mmol) and 423 ml of water), and the mixture was stirred at 0° C. for a further 1.5 hours. The mixture was extracted twice with 480 ml each time of methyl tert-butyl ether and once with 480 ml of ethyl acetate. The aqueous solution at 0° C. was adjusted to pH 7 with dilute hydrochloric acid (prepared from 37.1 g of 37% HCl and 151 ml of water). The solution was allowed to warm up to 20° C., and an aqueous solution of 205 g of ammonium chloride in 554 ml of water was added. The solution was stirred at 20° C. for 1 hour, and the product was filtered off and washed twice with 150 ml each time of water and once with 400 ml of acetonitrile. The product was dried at 40° C. under vacuum under entraining gas.

Yield: 165.51 g (94.3% of theory) of an almost colourless powder (very slight yellow tint).

HPLC Method E: RT: about 6.8 min.

MS (EIpos): m/z=380 $[M+H]^+$ $^1$H-NMR (300 MHz, DMSO-$d_6$): δ=1.14 (t, 3H), 2.14 (s, 3H), 2.37 (s, 3H), 3.73 (s, 3H), 4.04 (m, 2H), 5.33 (s, 1H), 7.26 (m, 2H), 7.32 (s, 1H), 7.57 (s, 1H), 8.16 (s, 1H), 11.43 (br. s, 1H).

Example 2d (4S)-4-(4-Cyano-2-methoxyphenyl)-5-ethoxy-2,8-dimethyl-1,4-dihydro-1,6-naphthyridine-3-carboxamide (I)

To an initial charge of 160 g (422 mmol) of 4-(4-cyano-2-methoxyphenyl)-5-ethoxy-2,8-dimethyl-1,4-dihydro-1,6-naphthyridine-3-carboxylic acid (VIIa) and 95.8 g (591 mol) of 1,1-carbodiimidazole in 800 ml of THF was added 5.1 g (0.0417 mol) of DMAP at 20° C. The mixture was stirred at 20° C. for one hour (evolution of gas!) and then heated to 50° C. for 2.5 hours. 297.3 g (1.842 mmol) of hexamethyldisilazane was added to this solution, which was boiled under reflux for 22 hours. A further 180 ml of THF was added and the mixture was cooled to 5° C. A mixture of 117 ml of THF and 83.5 g of water was added over 3 hours such that the temperature remained between 5 and 20° C. The mixture was subsequently boiled under reflux for one hour, then cooled via a gradient (3 hours) to 0° C. and stirred at this temperature for one hour. The product was filtered off and washed twice with 200 ml each time of THE and twice with 320 ml each time of water. The product was dried at 70° C. under vacuum under entraining gas.

Yield: 150 g (94% of theory) of an almost colourless powder (very slight yellow tint).

HPLC method D: RT about 6.7 min.

MS (EIpos): m/z=379 [M+H]+

1H-NMR (300 MHz, DMSO-d6): δ=1.05 (t, 3H), 2.12 (s, 3H), 2.18 (s, 3H), 3.82 (s, 3H), 3.99-4.07 (m, 2H), 5.37 (s, 1H), 6.60-6.84 (m, 2H), 7.14 (d, 1H), 7.28 (dd, 1H), 7.37 (d, 1H), 7.55 (s, 1H), 7.69 (s, 1H).

Example 2e

Preparation of Pure Product (I=Finerenone)

139.20 g of the crude product (I) prepared in Example 2d was suspended in 2796 ml of ethanol (denatured with toluene) and then heated to reflux. On heating, the product went into solution. Stirring was continued at this temperature for one hour. The solution was filtered off through a heated pressure filter (T=75° C.) and the pressure filter was then rinsed with 36 ml of ethanol (denatured with toluene). The solvent was then distilled off until about four times the final volume (with respect to substance used: 139.2 g×4~561 ml) had been attained (about 2304 ml was distilled off). The mixture was then cooled to internal temperature 23° C. (over about 1.5 to 2 hours). The mixture was then stirred at internal temperature 3° C. for 2 hours. The product was filtered off and rinsed once with 100 ml of ethanol (denatured with toluene). Wet yield: 145.60 g. The wet product was dried at 50° C. over the weekend (>48 h) under reduced pressure (<100 mbar). Yield: 133.7 g (96.0% of theory) of a colourless crystalline powder, fine needle-like crystals.

Analytical Results:

| | |
|---|---|
| Finerenone (I) | Purity: 99.86 area (HPLC); Content: 99.5% by weight |
| Enantiomeric excess | 100% e.e. |
| Largest secondary component impurity E | 0.07% |
| Residual solvents: | |
| EtOH | 0.05% |
| toluene | 0.00% |
| water (Karl Fischer) | 0.00% |

MS (EIpos): m/z=379 $[M+H]^+$ $^1$H-NMR (400 MHz, DMSO-$d_6$): δ=1.05 (t, 3H), 2.12 (s, 3H), 2.18 (s, 3H), 3.82 (s, 3H), 3.99-4.07 (m, 2H), 5.37 (s, 1H), 6.60-6.84 (m (broad signal)), 2H), 7.14 (d, 1H), 7.28 (dd, 1H), 7.37 (d, 1H), 7.55 (s, 1H), 7.69 (s, 1H) and small signals of the DMSO solvent and water at δ=2.5-2.6 and a very small peak at δ=3.38 (not assignable)

Modification: Mod A (as defined in WO2016/016287 A1)

Example 3a

Preparation of the diastereomeric salt (Va) of 2-cyanoethyl (4S)-4-(4-cyano-2-methoxyphenyl)-5-ethoxy-2,8-dimethyl-1,4-dihydro-1,6-naphthyridine-3-carboxylate with (+) Di-p-tolyl-D-tartaric acid 1000 g (2.31 mol) of racemic 2-cyanoethyl (4S, 4R)-4-(4-cyano-2-methoxyphenyl)-5-ethoxy-2,8-dimethyl-1,4-dihydro-1,6-naphthyridine-3-carboxylate (IV) and 695.5 g (1.80 mol) of (+)-di-p-tolyl-D-tartaric acid were suspended in a mixture of 15 l of a mixture of ethanol/water 3:1 and heated to 30° C. (forming a solution). The mixture was stirred at room temperature overnight, and the precipitate crystals were filtered off and washed twice with 1000 ml of a mixture of ethanol/water 3:1. The product was dried under reduced pressure at room temperature.

Yield: 950.5 g (100.5% of theory) of a colourless crystalline powder.

Analytical Results:

Enantiomeric purity (e.e. %): 78% e.e. (Method F)

An amount of the diastereomeric salt enriched in this way was purified further as follows:

950 g of the diastereomeric salt prepared was suspended in 10 l of a mixture of ethanol/water 3:1, and the mixture was stirred at 50° C. for 2 h and at room temperature overnight. The precipitated crystals were filtered off and washed twice with 1000 ml of a mixture of ethanol/water 3:1. The product was dried under reduced pressure at 40° C.

Yield: 781.3 g (82.6% of theory) of a colourless crystalline powder

Analytical Results:

Enantiomeric purity (e.e. %): 99% e.e. (Method F)

Example 3b

Preparation of 2-cyanoethyl (4S)-4-(4-cyano-2-methoxyphenyl)-5-ethoxy-2,8-dimethyl-1,4-dihydro-1,6-naphthyridine-3-carboxylate (IVa)

To 600 g (732.7 mmol) of the title compound from Example 3a was suspended in 6 l of a mixture of water/ ethanol 3:1, and the mixture was cooled to 0° C. Then a 20% aqueous sodium carbonate solution was metered in gradually (over the course of 1 hour) and the pH was adjusted to pH 7.1. The mixture was left to stir at that temperature for a further 4 hours. The precipitated solids were filtered off and washed twice with 1000 ml of a mixture (0° C.) of water/ethanol 3:1. The product was dried under reduced pressure at 40° C.

Yield: 308.0 g (97.2% of theory) of a colourless crystalline powder

Analytical Results:

Enantiomeric purity (e.e. %): 99% e.e.

In an analogous manner (as described in Examples 2c-2e), this prepared intermediate (IVa) was converted to the final stage (finerenone (Ia), pure):

Analytical Results:

| | |
|---|---|
| Finerenone (Ia) | Purity: 99.83 area (HPLC); Content: 99.3% by weight |
| Enantiomeric excess | 100% e.e. |
| Largest secondary component impurity E | 0.08% |
| Residual solvents: | |
| EtOH | 0.05% |
| toluene | 0.00% |
| water (Karl Fischer) | 0.00% |

Modification: Mod A (as defined in WO2016/016287 A1)

Example 4

Examples of Various Tartaric Acid Derivatives and Further Solvents

Example 4a

Preparation of the diastereomeric salt (Va) of 2-cyanoethyl (4S)-4-(4-cyano-2-methoxyphenyl)-5-ethoxy-2,8-dimethyl-1,4-dihydro-1,6-naphthyridine-3-carboxylate with (−)-di-O,O'-p-tolyl-L-tartaric acid 1.00 g of racemate (IV) was suspended together with 1.3 g (1.5 eq.) of (−)-di-O,O'-p-tolyl-L-tartaric acid in 50 ml of a mixture of ethanol/water 3:1, stirred and left to stand. After some time, the diastereomeric salt precipitated out. This was filtered off and dried (980 mg, 100% of theory), and the enantiomeric excess was measured. The measurement gave an enantiomeric excess of 73.28% e.e. in favour of (IVb).

Example 4b

Preparation of the diastereomeric salt (Va) of 2-cyanoethyl (4S)-4-(4-cyano-2-methoxyphenyl)-5-ethoxy-2,8-dimethyl-1,4-dihydro-1,6-naphthyridine-3-carboxylate with (−)-di-O,O'-p-tolyl-L-tartaric acid 100 mg of racemate (IV) was suspended with (−)-di-O,O'-p-tolyl-L-tartaric acid in a mixture of ethanol/water 3:1 and stirred at 40° C. for 3 hours and then left to stand at 20° C. for 16 hours. After some time, the diastereomeric salt precipitated out. This was filtered off and dried, and the enantiomeric excess (EE) was measured. The measurements gave enantiomeric excesses in favour of (IVb). The following table summarizes the results:

| (−)-di-O,O'-p-tolyl-L-tartaric acid Equiv. | Amount [mg] | Solvent | Amount [ml] | EE value |
|---|---|---|---|---|
| 1.1 | 98 | ethanol/water 75:25 | 4 | 62.34 |
| 1.1 | 98 | ethanol/water 75:25 | 5 | 82.8 |
| 1.2 | 107 | ethanol/water 75:25 | 4 | 74.26 |
| 1.2 | 107 | ethanol/water 75:25 | 5 | 80.7 |
| 1.3 | 116 | ethanol/water 75:25 | 4 | 78.22 |
| 1.3 | 116 | ethanol/water 75:25 | 5 | 81.52 |
| 1.4 | 125 | ethanol/water 75:25 | 4 | 80.28 |
| 1.4 | 125 | ethanol/water 75:25 | 5 | 83.84 |
| 1.5 | 134 | ethanol/water 75:25 | 4 | 75.7 |
| 1.5 | 134 | ethanol/water 75:25 | 5 | 80.34 |
| 2 | 179 | ethanol/water 75:25 | 4 | 77.84 |
| 2 | 179 | ethanol/water 75:25 | 5 | 60.06 |

Example 4c

Preparation of the diastereomeric salt (Va) of 2-cyanoethyl (4S)-4-(4-cyano-2-methoxyphenyl)-5-ethoxy-2,8-dimethyl-1,4-dihydro-1,6-naphthyridine-3-carboxylate with (−)-di-O,O'-p-tolyl-L-tartaric acid In a series of experiments, 100 mg of racemate (IV) was suspended with (−)-di-O,O'-p-tolyl-L-tartaric acid in a mixture of ethanol/water and stirred at 50° C. for 3 hours and then left to stand at 20° C. for 16 hours. After some time, the diastereomeric salt precipitated out. This was filtered off and dried, and the enantiomeric excess was measured. The measurements gave enantiomeric excesses in favour of (IVb). The following table summarizes the results:

| (−)-di-O,O'-p-tolyl-L-tartaric acid Equiv. | Amount [mg] | Solvent | Amount [ml] | EE value |
|---|---|---|---|---|
| 0.8 | 71 | ethanol/water 70:30 | 2 | 69.7 |
| 0.8 | 71 | ethanol/water 70:30 | 4 | 86.6 |
| 1.05 | 94 | ethanol/water 75:25 | 2 | 72.6 |
| 1.05 | 94 | ethanol/water 75:25 | 4 | 88.5 |
| 1.05 | 94 | ethanol/water 75:25 | 6 | 76.4 |
| 1.05 | 94 | ethanol/water 70:30 | 2 | 68.4 |
| 1.05 | 94 | ethanol/water 70:30 | 4 | 84.9 |
| 1.05 | 94 | ethanol/water 70:30 | 6 | 85.3 |
| 1.2 | 107 | ethanol/water 75:25 | 2 | 76.4 |
| 1.2 | 107 | ethanol/water 75:25 | 4 | 87.8 |
| 1.2 | 107 | ethanol/water 75:25 | 6 | 88.9 |
| 1.2 | 107 | ethanol/water 70:30 | 4 | 81.6 |
| 1.2 | 107 | ethanol/water 70:30 | 6 | 86.4 |

Example 4c

Preparation of the diastereomeric salts (Va) of 2-cyanoethyl (4S)-4-(4-cyano-2-methoxyphenyl)-5-ethoxy-2,8-dimethyl-1,4-dihydro-1,6-naphthyridine-3-carboxylate by use of different tartaric acid derivatives 100 mg of racemate (IV) was suspended with a tartaric acid derivative in a mixture in 4 ml of solvent and stirred at 50° C. for 3 hours and then left to stand at 20° C. for 16 hours. After some time, the diastereomeric salt precipitated out. This was filtered off and dried, and the enantiomeric excess and also the $^1$H-NMR and mass by mass spectrometer were measured. The measurements gave enantiomeric excesses in favour of (IVa). The following table summarizes the results:

| Reagent | (eq) | Amount (mg) | Solvent | EE value |
|---|---|---|---|---|
| (−)-di-O,O'-p-chlorobenzoyl-D-tartaric acid | 1.05 | 103 | ethanol/water (70:30) | 77.26 |
| MS (EIpos): m/z = 433 [M + H]$^+$ | | | | |
| $^1$H-NMR (400 MHz, DMSO-$d_6$): δ = 0.93-1.35 (m, 2 H), 1.88-2.34 (m, 2 H), 3.63-3.87 (m, 2 H), 3.94-4.32 (m, 2 H), 5.12-5.48 (m, 1 H), 5.69-6.06 (m, 1 H), 7.06-7.43 (m, 2 H), 7.53-7.85 (m, 3 H), 7.91-8.81 (m, 3 H), 12.68-15.10 (m, 1 H) | | | | |
| (−)-di-O,O'-p-bromobenzoyl-D-tartaric acid | 1.05 | 125 | ethanol/water (70:30) | 71.64 |
| MS (EIpos): m/z = 433 [M + H]$^+$ | | | | |
| $^1$H-NMR (400 MHz, DMSO-$d_6$): δ = 0.89-1.33 (m, 1 H), 2.03-2.45 (m, 2 H), 2.60-3.01 (m, 1 H), 3.77 (s, 1 H), 3.86-4.26 (m, 1 H), 5.36 (s, 1 H), 5.86 (s, 1 H), 7.04-7.41 (m, 1 H), 7.60 (s, 1 H), 7.73-8.04 (m, 3 H), 8.26-8.52 (m, 1 H), 12.80-14.97 (m, 1 H) | | | | |
| (+)-di-O,O'-(2,4-dichlorobenzoyl)-D-tartaric acid | 1.05 | 120 | n-propanol/water (70:30) | 76.85 |
| MS (EIpos): m/z = 433 [M + H]$^+$ | | | | |
| $^1$H-NMR (400 MHz, DMSO-$d_6$): δ = 1.11 (t, J = 7.03 Hz, 1 H), 2.16 (s, 1 H), 2.42 (s, 1 H), 2.67-3.00 (m, 1 H), 3.77 (s, 1 H), 3.95-4.46 (m, 1 H), 5.36 (s, 1 H), 5.90 (s, 1 H), 7.22-7.38 (m, 1 H), 7.58-7.74 (m, 1 H), 7.82-7.93 (m, 1 H), 8.31-8.45 (m, 1 H), 13.37-15.42 (m, 1 H) | | | | |

Example 5a

Preparation of the diastereomeric salt (Va) of 2-cyanoethyl (4S)-4-(4-cyano-2-methoxyphenyl)-5-ethoxy-2,8-dimethyl-1,4-dihydro-1,6-naphthyridine-3-carboxylate with (−)-di-O,O'-p-chlorobenzoyl-D-tartaric acid 1000 g (2.31 mol) of racemic 2-cyanoethyl (4S, 4R)-4-(4-cyano-2-methoxyphenyl)-5-ethoxy-2,8-dimethyl-1,4-dihydro-1,6-naphthyridine-3-carboxylate (IV) and 854.38 g (2.0 mol) of (+)-di-O,O'-p-chlorobenzoyl-D-tartaric acid are suspended in a mixture of 30 l of a mixture of ethanol/water 7:3 and heated to 50° C. (forming a solution). The mixture is stirred at room temperature overnight, and the precipitate crystals are filtered off and washed twice with 1000 ml of a mixture of ethanol/water 7:1. The product was dried under reduced pressure at room temperature.

Yield: 1105.0 g (111.3% of theory) of a colourless crystalline powder

Analytical Results:

Enantiomeric purity (e.e. %): 79% e.e.

An amount of the diastereomeric salt enriched in this way was purified further as follows:

1104 g of the diastereomeric salt prepared was suspended in 10 l of a mixture of ethanol/water 7:1, and the mixture was stirred at 50° C. for 2 h and at room temperature overnight. The precipitated crystals were filtered off and washed twice with 1000 ml of a mixture of ethanol/water 3:1. The product was dried under reduced pressure at 40° C.

Yield: 812.7 g (81.8% of theory) of a colourless crystalline powder

Analytical Results:

Enantiomeric purity (e.e. %): 99% e.e.

Example 5b

Preparation of 2-cyanoethyl (4S)-4-(4-cyano-2-methoxyphenyl)-5-ethoxy-2,8-dimethyl-1,4-dihydro-1,6-naphthyridine-3-carboxylate (IVa)

To 600 g (697.95 mmol) of the title compound from Example 5a was suspended in 6 l of a mixture of water/ethanol 3:1, and the mixture was cooled to 0° C. Then a 20% aqueous sodium carbonate solution was metered in gradually (over the course of 1 hour) and the pH was adjusted to pH 7.1. The mixture was left to stir at that temperature for a further 4 hours. The precipitated solids were filtered off and washed twice with 1000 ml of a mixture (0° C.) of water/ethanol 3:1. The product was dried under reduced pressure at 40° C.

Yield: 285.8 g (94.7% of theory) of a colourless crystalline powder

Analytical Results:

Enantiomeric purity (e.e. %): 99% e.e.

In an analogous manner (as described in Examples 2c-2e), this prepared intermediate (IVa) was converted to the final stage (finerenone, pure):

Analytical results:

| | |
|---|---|
| Finerenone (I) | Purity: 99.87 area (HPLC); Content: 99.9% by weight |
| Enantiomeric excess | 100% e.e. |
| Largest secondary component impurity E | 0.04% |
| Residual solvents: | |
| EtOH | 0.05% |
| toluene | 0.00% |
| water (Karl Fischer) | 0.00% |

Modification: Mod A (as defined in WO2016/016287 A1).

The invention claimed is:

1. A diastereomeric salt of the formula (Va)

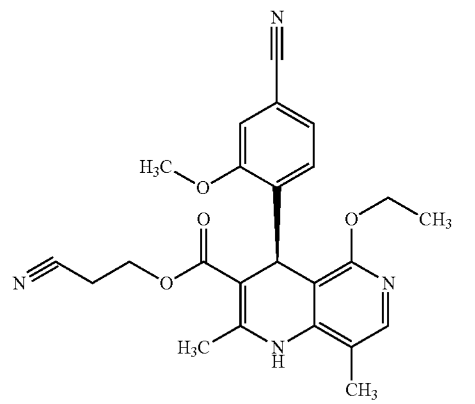

-continued
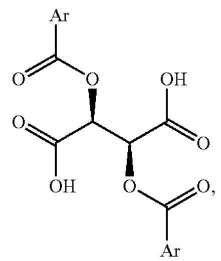
(Vb)
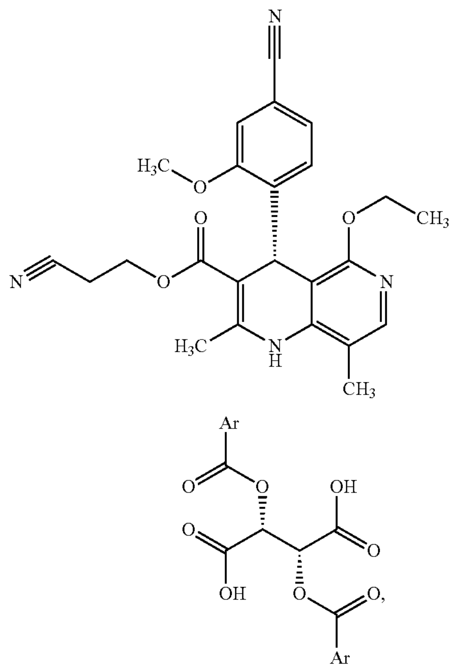
(Vc)
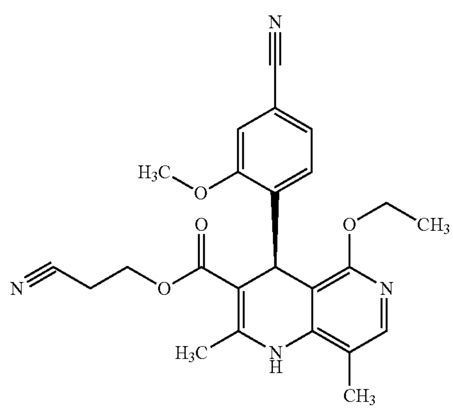
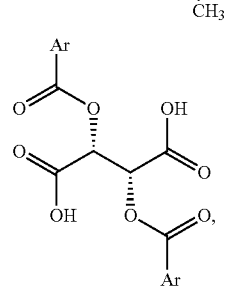
or
-continued
(Vd)
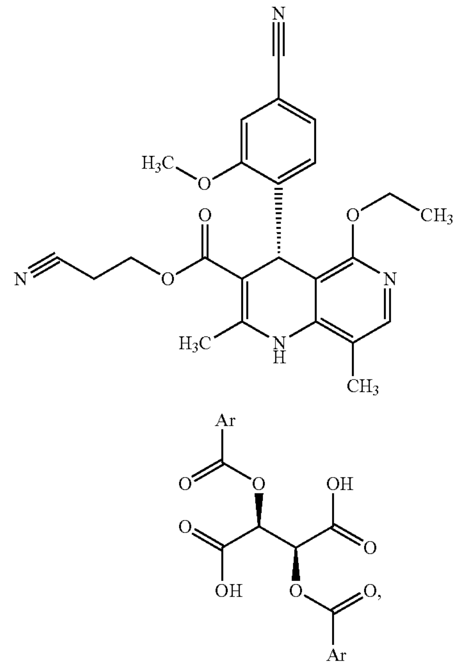
in which Ar is unsubstituted or substituted aryl or heteroaryl.
2. The diastereomeric salt according to claim 1, wherein Ar is one of the formulae
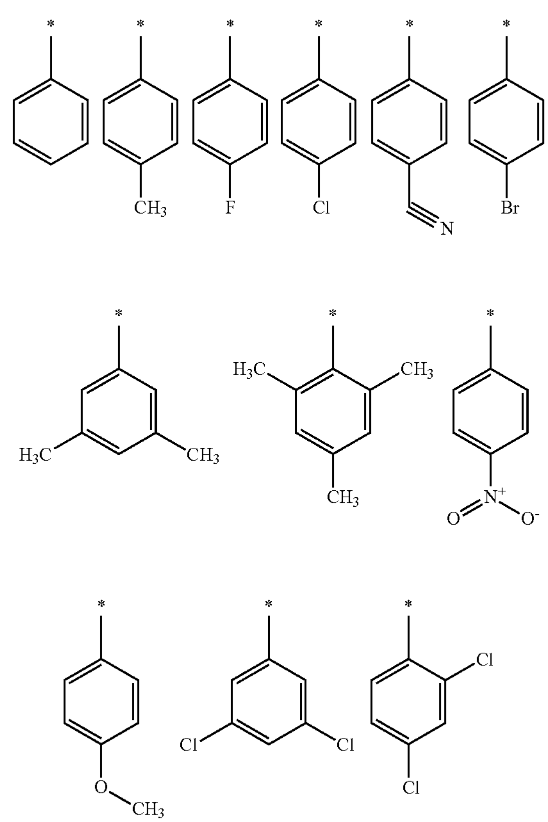

-continued

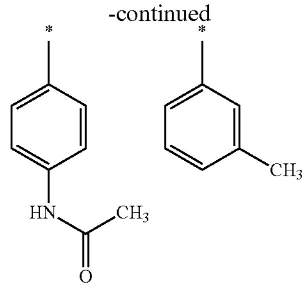

in which * represents the site of attachment.

3. The diastereomeric salt according to claim 1, wherein Ar is one of the formulae

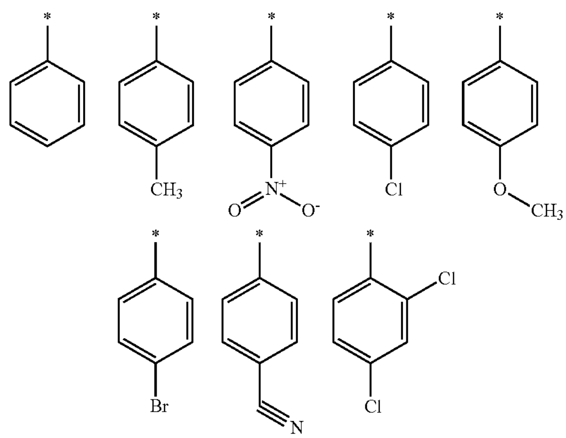

in which * represents the site of attachment.

4. The diastereomeric salt according to claim 1, wherein Ar is one of the formulae

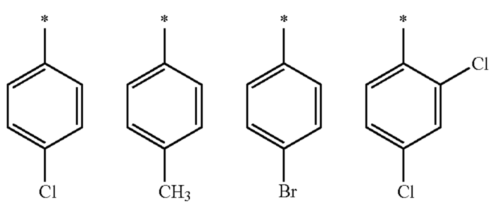

in which * represents the site of attachment.

5. The diastereomeric salt according to claim 1, wherein Ar is one of the formulae

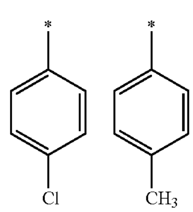

in which * represents the site of attachment.

6. The diastereomeric salt according to claim 1, wherein Ar is

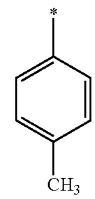 [SMILES: *c1ccc(C)cc1]

in which * represents the site of attachment.

7. A process for preparing the diastereomeric salt (Va), (Vb), (Vc) and/or (Vd) according to claim 1, comprising the step of (i) resolving by optical resolution racemic 2-cyanoethyl-4-(4-cyano-2-methoxyphenyl)-5-ethoxy-2,8-dimethyl-1,4-dihydro-1,6-naphthyridine-3-carboxylate of the formula (IV)

(IV)

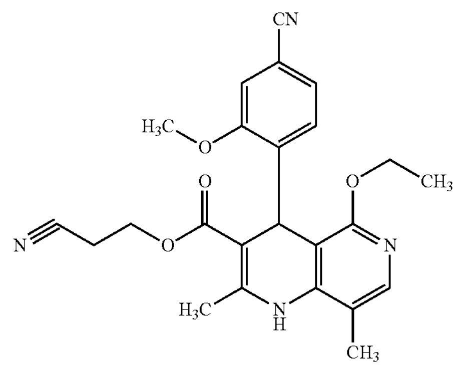

with a chiral substituted tartaric ester of the formula (IIIa) or (IIIb)

(IIIa)

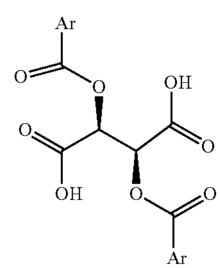

or (IIIb)

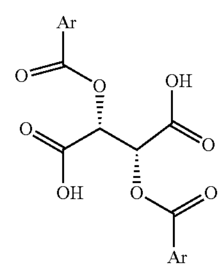

where Ar is unsubstituted or substituted aryl or heteroaryl.

8. The process according to claim 7, wherein the optical resolution in step (i) is effected at a temperature in the range of 20° C. to 50° C.

9. A process for preparing 2-cyanoethyl (4S)-4-(4-cyano-2-methoxyphenyl)-5-ethoxy-2,8-dimethyl-1,4-dihydro-1,6-naphthyridine-3-carboxylate of the formula (IVa)

(IVa)

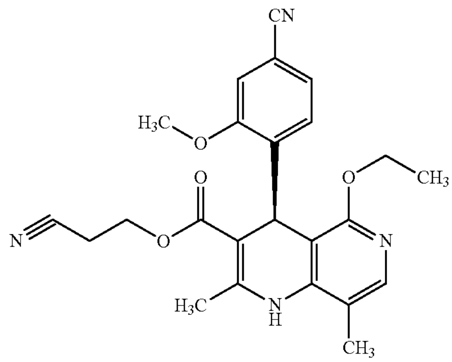

comprising steps (i) and (iii):

(i) resolving by optical resolution racemic 2-cyanoethyl-4-(4-cyano-2-methoxyphenyl)-5-ethoxy-2,8-dimethyl-1,4-dihydro-1,6-naphthyridine-3-carboxylate of the formula (IV)

(IV)

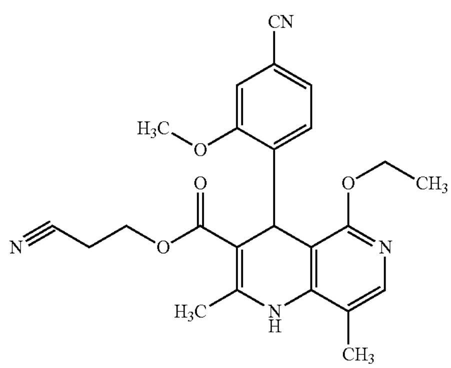

with a chiral substituted tartaric ester of the formula (IIIa) or (IIIb)

(IIIa)

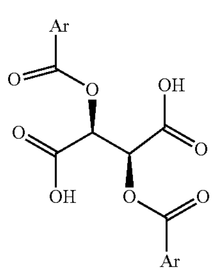

or

-continued (IIIb)

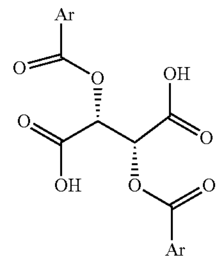

to obtain one or more of the diastereomeric salts (Va)

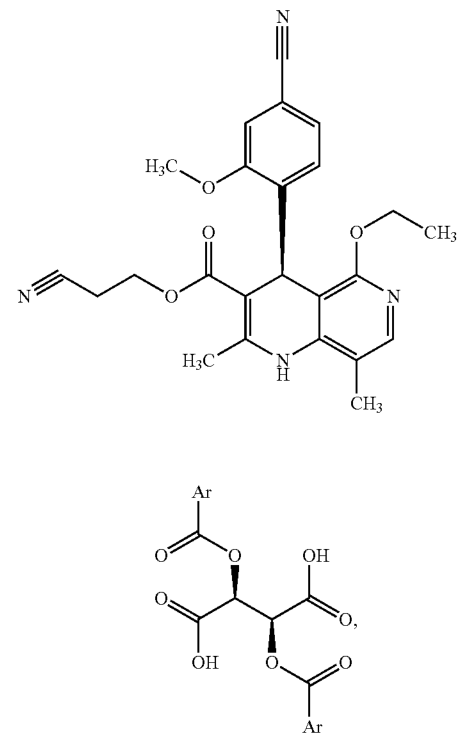

(Vb)

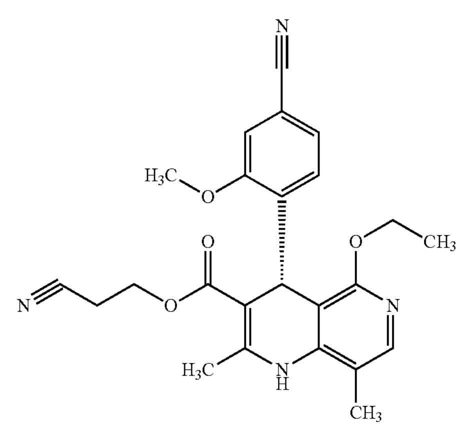

-continued

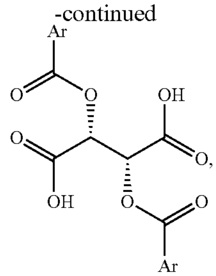

(Vc)

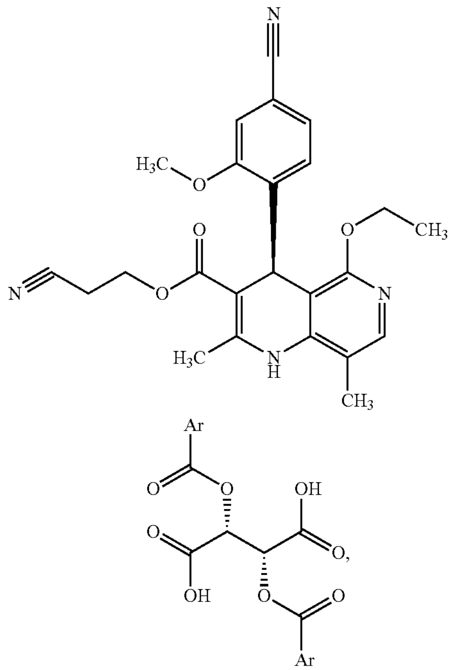

(Vd)

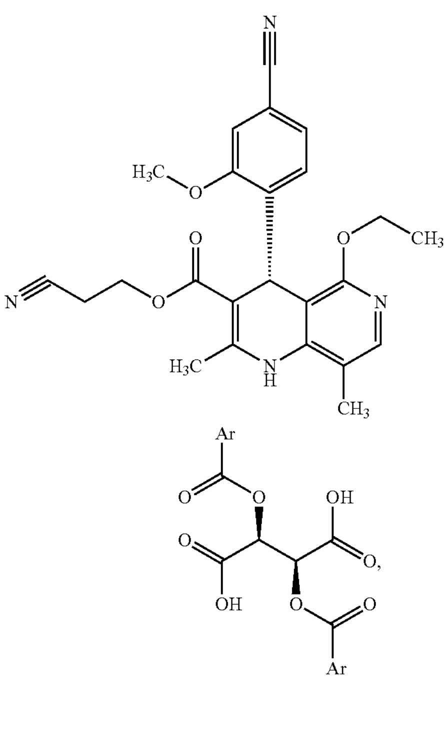
and/or where Ar is unsubstituted or substituted aryl or heteroaryl, and (iii) converting the diastereomeric salt obtained in step (i) to the compound of formula (IVa).

10. The process according to claim 9, comprising step (iii), wherein the step (iii) further comprises treating the diastereomeric salt (Va), (Vb), (Vc) and/or (Vd) obtained in step (i) with a base.

11. The process according to claim 10, wherein, in step (iii), the base is an inorganic base and is selected from ammonia, sodium hydroxide solution, lithium hydroxide, potassium hydroxide, ammonium carbonate, sodium carbonate, potassium carbonate, lithium carbonate, ammonium hydrogencarbonate, sodium hydrogencarbonate, potassium hydrogencarbonate, sodium phosphate, potassium phosphate, ammonium phosphate, and sodium hydroxide.

12. The process according to claim 10, wherein, in step (iii), the solvent or solvent mixture is held at a temperature of 0° C. to 60° C., then adjusted to a pH of 6.9 to 8.0, by adding the base.

13. The process according to claim 9, wherein the racemate (IV)

(IV)

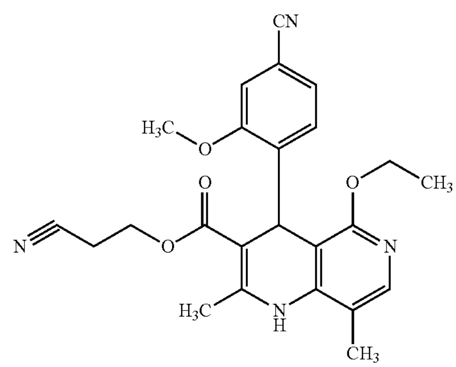

in step (i) is reacted with di-p-tolyl-D-tartaric acid of the formula (IIIa')

(IIIa')

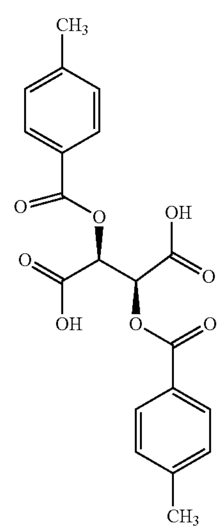

in a spirits/water mixture to give the diastereomeric salt (Va')

(Va')

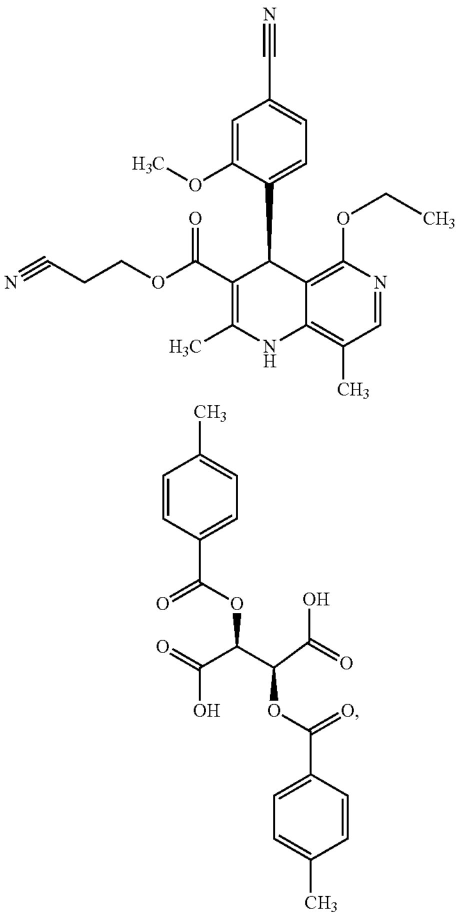

and then, in step (iii), cyanoethanol ester (IVa)

(IVa)

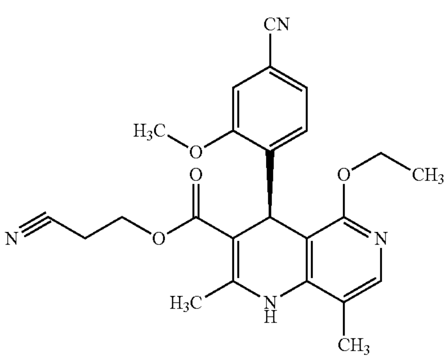

is released using sodium phosphate, likewise in a spirits/water mixture.

14. A process for preparing (4S)-4-(4-cyano-2-methoxyphenyl)-5-ethoxy-2,8-dimethyl-1,4-dihydro-1,6-naphthyridine-3-carboxamide of the formula (Ia), comprising steps (i), (iii), (v) and (vi):

(i) resolving by optical resolution racemic 2-cyanoethyl-4-(4-cyano-2-methoxyphenyl)-5-ethoxy-2,8-dimethyl-1,4-dihydro-1,6-naphthyridine-3-carboxylate of the formula (IV)

(IV)

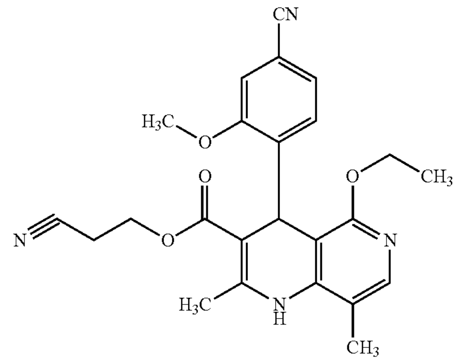

with a chiral substituted tartaric ester of the formula (IIIa) or (IIIb)

(IIIa)

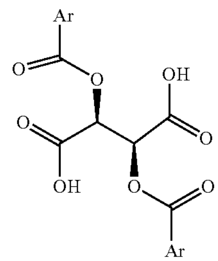

or (IIIb)

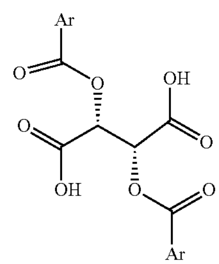

to obtain one or more of the diastereomeric salts (Va)

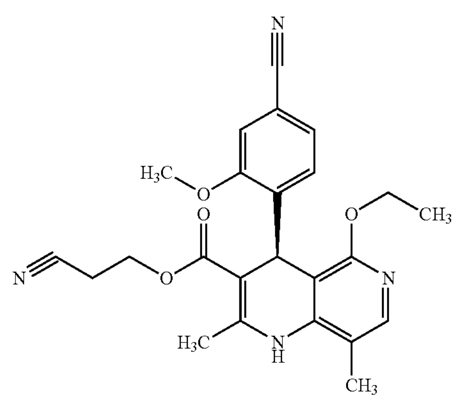

-continued
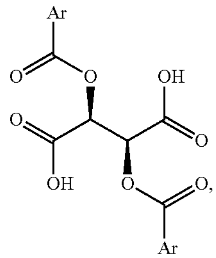
(Vb)
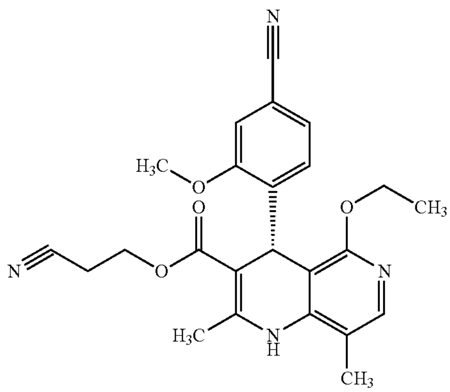
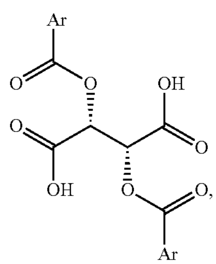
(Vc)
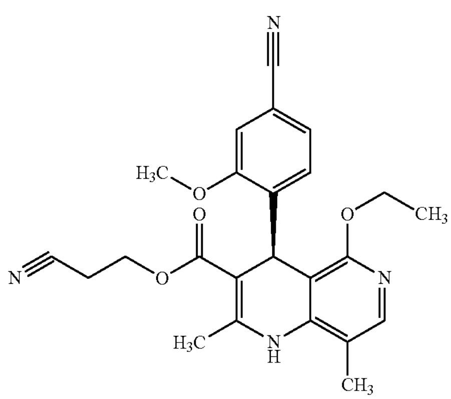
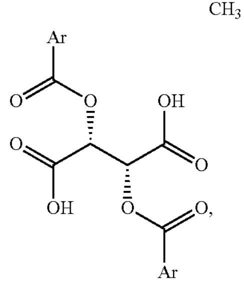
-continued
(Vd)
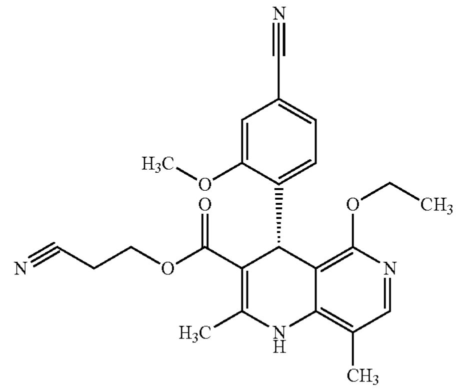
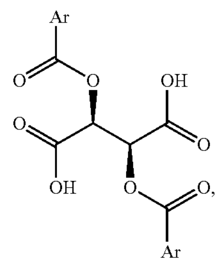
and/or
where Ar is unsubstituted or substituted aryl or heteroaryl,
(iii) converting the diastereomeric salt obtained in step (i) to the compound of formula (IVa)
(IVa)
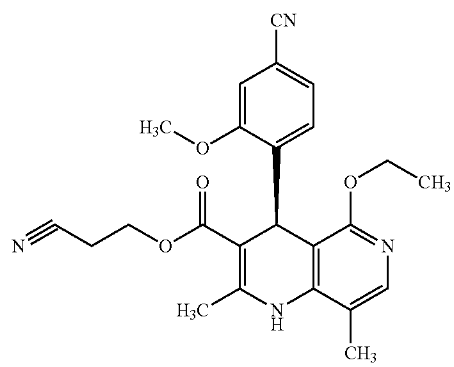
(v) hydrolysing the compound of formula (IVa) with sodium hydroxide solution in a THF/water mixture (2:1) to give the compound of the formula (VIIa)
(VIIa)
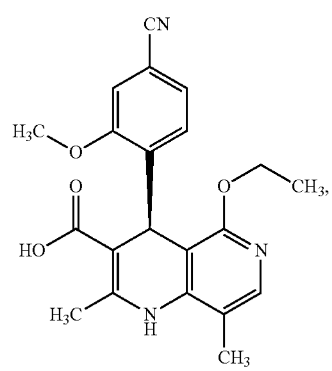

(vi) reacting the compound of the formula (VIIa), in THF as solvent, firstly with 1,1-carbodiimidazole and catalytic amounts of 4-(dimethylamino)pyridine, adding hexamethyldisilazane and then heating the mixture under reflux for 16-24 hours, and then adding a THF/water mixture, so as to obtain the compound of formula (Ia).

15. The process according to claim 12, wherein, in step (iii), the solvent or solvent mixture is held at a temperature of 0° C. to 60° C., then adjusted to a pH of 7.0 to 7.5, by adding the base.

16. The process according to claim 12, wherein, in step (iii), the solvent or solvent mixture is held at a temperature of 0° C. to 60° C., then adjusted to a pH of 7.1, by adding the base.

* * * * *